US007550140B2

(12) United States Patent
Bakker et al.

(10) Patent No.: US 7,550,140 B2
(45) Date of Patent: Jun. 23, 2009

(54) ANTIBODY TO THE HUMAN OX40 RECEPTOR

(75) Inventors: Alexander Berthold Hendrik Bakker, Hillegom (NL); Pauline Marie Louise Meester-Rood, Alkmaar (NL); Adrianus Quirinus Bakker, Abbekerk (NL)

(73) Assignee: Crucell Holland B.V., Leiden (NL)

( * ) Notice: Subject to any disclaimer, the term of this patent is extended or adjusted under 35 U.S.C. 154(b) by 577 days.

(21) Appl. No.: 10/517,941

(22) PCT Filed: Jun. 13, 2003

(86) PCT No.: PCT/EP03/06341

§ 371 (c)(1),
(2), (4) Date: Dec. 13, 2004

(87) PCT Pub. No.: WO03/106498

PCT Pub. Date: Dec. 24, 2003

(65) Prior Publication Data
US 2006/0281072 A1 Dec. 14, 2006

(30) Foreign Application Priority Data
Jun. 13, 2002 (NL) .................... PCT/NL02/00389

(51) Int. Cl.
*A61K 39/395* (2006.01)
*A61K 39/00* (2006.01)
*A61K 38/00* (2006.01)
*C12N 5/02* (2006.01)
*C12N 5/06* (2006.01)

(52) U.S. Cl. ............. 424/130.1; 424/139.1; 424/178.1; 514/12; 435/331

(58) Field of Classification Search ....................... None
See application file for complete search history.

(56) References Cited

U.S. PATENT DOCUMENTS

| 5,696,100 | A | 12/1997 | Holme et al. |
| 5,821,332 | A | 10/1998 | Godfrey et al. |
| 6,265,150 | B1 | 7/2001 | Terstappen et al. |
| 6,277,962 | B1 | 8/2001 | Godfrey et al. |
| 6,312,700 | B1 | 11/2001 | Weinberg |
| 2001/0044522 | A1 | 11/2001 | Godfrey et al. |

FOREIGN PATENT DOCUMENTS

| WO | WO 98/15833 | 4/1998 |
| WO | WO 99/42585 | 8/1999 |
| WO | WO 03/106498 | 12/2003 |
| WO | WO 95/12673 | 12/2003 |

OTHER PUBLICATIONS

Vajdos et al., Comprehensive Functional Maps of the Antigen-binding Site of an Anti-ErbB2 Antibody Obtained with Shotgun Scanning Mutagenesis. J. Mol. Biol., 320: 415-428, 2002.*
Beiboer et al., Guided selection of a pan-Carcinoma specific antibody reveals similar binding characteristics yet structural divergence between the original murine antibody and its human equivalent. J.Mol. Biol. 296, 833-849, 2000.*
MacCallum et al., Antibody-antigen Interactions: Contact Analysis an dBinding Site Topgraphy. J. Mol. Biol. 262: 732-745, 1996.*
Klimka et al., Human anti-CD30 Reccombinant antibodies guided phage antibody selection using cell panning. British J. Cancer., 83, 252-260, 2000.*
PCT International Search Report, PCT/EP2003/106498, dated Jan. 7, 2004.
Vaughan et al., "Human antibodies by design," Nature Biotechnology, Jun. 1998, pp. 535-539, vol. 16.
Weinberg et al., "Engagement of the OX-40 Receptor In Vivo Enhances Antitumor Immunity," Journal of Immunology, Feb. 15, 2000, pp. 2160-2169, vol. 164, No. 4.
Weinberg, A., "OX40: targeted immunotherapy - implications for tempering autoimmunity and enhancing vaccines," Trends in Immunology, Feb. 2002, pp. 102-109, vol. 23, No. 2.
PCT International Search Report, PCT/EP03/06341, dated Jan. 1, 2004.
PCT International Preliminary Examination Report, PCT/EP03/06341, dated Jul. 21, 2004.

* cited by examiner

*Primary Examiner*—Lorraine Spector
*Assistant Examiner*—Elly-Gerald Stoica
(74) *Attorney, Agent, or Firm*—TraskBritt

(57) ABSTRACT

The present invention provides binding molecules, such as human binding molecules, that bind to and stimulate the human OX40-receptor. The invention also provides nucleic acids encoding such binding molecules. Methods for producing such binding molecules are also provided by the present invention. The binding molecules and nucleic acids are useful in the stimulation of human T-cells and can be used to enhance antigen-specific immune responses.

8 Claims, 21 Drawing Sheets

Anti-human OX40R scFv SC02008

```
                NcoI
                -----
           M  A  E  V  Q  L  V  E  S  G  G  G  L  V  Q  P  G  G  S  L  R
143        CCATGGCTGAGGTGCAGCTGGTGGAGTCTGGGGGAGGCTTGGTCCAGCCTGGAGGGTCCCTGAG

L  S  C  A  A  S  G  F  T  F  S  N  Y  T  M  N  W  V  R  Q  A  P  G
214  ACTCTCCTGTGCAGCCTCTGGATTCACCTTTAGCAACTACACGATGAACTGGGTCCGCCAGGCGCCCGGGA

K  G  L  E  W  V  S  A  I  S  G  S  G  G  S  T  Y  Y  A  D  S  V  K  G
285  AGGGGCTGGAGTGGGTCTCAGCTATTAGTGGTAGTGGTGGTAGCACATACTACGCAGACTCCGTGAAGGGC

R  F  T  I  S  R  D  N  S  K  N  T  L  Y  L  Q  M  N  S  L  R  A  E  D
356      CGGTTCACCATCTCCAGAGACAATTCCAAGAACACGCTGTATCTGCAAATGAACAGCCTGAGAGCCGAGGA

T  A  V  Y  Y  C  A  K  D  R  Y  S  Q  V  H  Y  A  L  D  Y  W  G  Q
427      CACGGCCGTGTATTACTGTGCCAAAGACCGCTACTCCCAGGTGCACTACGCGTTGGATTACTGGGGCCAGG

G  T  L  V  T  V  L  E  G  T  G  G  S  G  G  T  G  S  G  T  G  T  S  E
498  GCACCCTGGTGACCGTGCTCGAGGGTACCGGAGGTTCCGGCGGAACCGGGTCTGGGACTGGTACGAGCGAG

L  D  I  Q  M  T  Q  S  P  D  S  L  P  V  T  P  G  E  P  A  S  I  S  C
569      CTCGACATCCAGATGACGCAGTCTCCAGACTCACTGCCCGTCACCCCTGGAGAGCCGGCCTCCATCTCCTG

R  S  S  Q  S  L  L  H  S  N  G  Y  N  Y  L  D  W  Y  L  Q  K  A  G
640      CAGGTCTAGTCAGAGCCTCCTGCATAGTAATGGATACAACTATTTGGATTGGTACCTGCAGAAGGCAGGGC

Q  S  P  Q  L  L  I  Y  L  G  S  N  R  A  S  G  V  P  D  R  F  S  G  S
711      AGTCTCCACAGCTCCTGATCTATTTGGGTTCTAATCGGGCCTCCGGGGTCCCTGACAGGTTCAGTGGCAGT

G  S  G  T  D  F  T  L  K  I  S  R  V  E  A  E  D  V  G  V  Y  Y  C  Q
782      GGATCAGGCACAGATTTTACACTGAAAATCAGCAGAGTGGAGGCTGAGGATGTTGGGGTTTATTACTGCCA

NotI
                                                              -----
         Q  Y  Y  N  H  P  T  T  F  G  Q  G  T  K  L  E  I  K  R  A  A
853      GCAGTACTACAACCACCCGACGACCTTCGGCCAGGGCACCAAACTGGAAATCAAACGCGCGGCCGC
```

Figure 5

Anti-human OX40R scFv SC02009

```
                                     NcoI
                                     ~~~~~~
                        M   A   E   V   Q   L   V   E   S   G   G   G   L
143                     CCATGGCTGAGGTGCAGCTGGTGGAGTCTGGGGGAGGCTTG

V   Q   P   G   G   S   L   R   L   S   C   A   A   S   G   F   T   F   S   G   Y   S   M   N
214     GTCCAGCCTGGGGGGTCCCTGAGACTCTCCTGTGCAGCCTCTGGATTCACCTTCAGCGGCTACTCTATGAA

W   V   R   Q   A   P   G   K   G   L   E   W   V   G   R   T   R   N   K   A   N   S   Y
285     CTGGGTCCGCCAGGCGCCCGGGAAGGGGCTGGAGTGGGTTGGCCGTACTAGAAACAAAGCTAACAGTTACA

T   T   E   Y   A   A   S   V   K   G   R   F   T   I   S   R   D   D   S   K   N   S   L   Y
356     CCACAGAATACGCCGCGTCTGTGAAAGGCAGATTCACCATCTCAAGAGATGATTCAAAGAACTCACTGTAT

L   Q   M   N   S   L   R   A   E   D   T   A   V   Y   Y   C   A   K   D   R   Y   V   N   T
427     CTGCAAATGAACAGTCTGAGAGCCGAGGACACAGCCGTGTATTACTGTGCCAAAGACCGCTACGTCAACAC

S   N   A   F   D   Y   W   G   Q   G   T   L   V   T   V   L   E   G   T   G   G   S   G
498     GTCGAACGCGTTCGATTACTGGGGCCAGGGCACCCTGGTGACCGTGCTCGAGGGTACCGGAGGTTCCGGCG

G   T   G   S   G   T   G   T   S   E   L   D   I   Q   M   T   Q   S   P   D   S   L   P   V
569     GAACCGGGTCTGGGACTGGTACGAGCGAGCTCGACATCCAGATGACACAGTCTCCAGACTCACTGCCCGTC

T   P   G   E   P   A   S   I   S   C   R   S   S   Q   S   L   L   H   S   N   G   Y   N   Y
640     ACCCCTGGAGAGCCGGCCTCCATCTCCTGCAGATCTAGTCAGAGCCTCCTGCATAGTAATGGATACAACTA

L   D   W   Y   L   Q   K   P   G   Q   S   P   Q   L   L   I   Y   L   G   S   N   R   A
711     TTTGGATTGGTACCTGCAGAAGCCAGGGCAGTCTCCACAGCTCCTGATCTATTTGGGTTCTAATCGGGCCT

S   G   V   P   D   R   F   S   G   S   G   S   G   T   D   F   T   L   K   I   S   R   V   E
782     CCGGGGTCCCTGACAGGTTCAGTGGCAGTGGATCAGGCACAGATTTTACACTGAAAATCAGCAGAGTGGAG

A   H   H   V   G   V   Y   Y   C   Q   Q   Y   P   L   G   P   P   T   F   G   Q   G   T   K
853     GCTCACCATGTTGGGGTTTATTACTGCCAGCAGTACCCGCTGGGCCCGCCCACCTTCGGCCAGGGCACCAA

NotI
                                     ~~~~~~~~
        L   E   I   K   R   A   A
924     ACTGGAAATCAAACGCGCGGCCGC
```

Figure 6

Anti-human OX40R scFv SC02010

```
                                                          NcoI
                                                          ~~~~~
                                                    M  A  E  V  Q  L  V
     72                                             CCATGGCTGAGGTGCAGCTGGTGG

E  S  G  G  G  L  I  Q  P  G  G  S  L  R  L  S  C  A  A  S  G  F  T  F
    143  AGTCTGGGGGAGGCTTGATCCAGCCTGGGGGGTCCCTGAGACTCTCCTGTGCAGCCTCTGGATTCACCTTC

S  G  Y  P  M  N  W  V  R  Q  A  P  G  K  G  L  E  W  V  A  V  I  S  Y
    214  AGCGGCTACCCTATGAACTGGGTCCGCCAGGCGCCCGGGAAGGGGCTGGAGTGGGTGGCAGTTATATCATA

D  G  S  N  K  Y  Y  A  D  S  V  K  G  R  F  T  I  S  R  D  N  S  K
    285  TGATGGAAGTAATAAATACTACGCAGACTCCGTGAAGGGCCGATTCACCATCTCCAGAGACAATTCCAAGA

N  T  L  Y  L  Q  M  N  S  L  R  A  E  D  T  A  V  Y  Y  C  A  R  D  M
                                                                             ─  ─
    356  ACACGCTGTATCTGCAAATGAACAGCCTGAGAGCTGAGGACACAGCCGTGTATTACTGTGCAAGAGACATG

S  G  F  H  E  F  D  Y  W  G  Q  G  T  L  V  T  V  L  E  G  T  G  G  S
         ─  ─  ─  ─  ─  ─  ─  ─
    427  TCCGGCTTCCACGAGTTCGATTACTGGGGCCAGGGCACCCTGGTGACCGTGCTCGAGGGTACCGGAGGTTC

G  G  T  G  S  G  T  G  T  S  E  L  T  Q  S  P  S  S  L  S  A  S  V
    498  CGGCGGAACCGGGTCTGGGACTGGTACGAGCGAGCTCACCCAGTCTCCATCCTCCCTGTCTGCATCTGTAG

G  D  R  V  T  I  T  C  R  A  S  Q  S  I  S  S  Y  L  N  W  Y  Q  Q  K
    569  GAGACAGAGTCACCATCACTTGCCGGGCAAGTCAGAGCATTAGCAGCTACTTAAATTGGTATCAGCAGAAA

P  G  K  A  P  K  L  L  I  Y  A  A  S  S  L  Q  S  G  V  P  S  R  F  S
    640  CCAGGGAAAGCCCCTAAGCTCCTGATCTATGCTGCATCCAGTTTGCAAAGTGGGGTCCCATCAAGGTTCAG

G  S  G  S  G  T  D  F  T  L  T  I  S  S  L  Q  P  E  D  F  A  T  Y
    711  TGGCAGTGGATCTGGGACAGATTTCACTCTCACCATCAGCAGTCTGCAACCTGAAGATTTTGCAACTTACT
                                                                          NotI
                                                                          ~~~~~
         Y  C  Q  Q  S  Y  S  T  P  P  T  F  G  Q  G  T  K  V  E  I  K  R  A  A
    782  ACTGTCAACAGAGTTACAGTACCCCTCCAACGTTCGGCCAAGGGACCAAGGTGGAGATCAAACGTGCGGCC

Anti-human OX40R scFv SC02011

```
                    NcoI
                    -------
             M  A  E  V  Q  L  V  E  S  G  G  V  V  Q  P  G  R
143          CCATGGCTGAGGTGCAGCTGGTGGAGTCTGGGGGAGGCGTGGTCCAGCCTGGGAGGT

S  L  R  L  S  C  A  A  S  G  F  T  F  S  D  Y  T  M  N  W  V  R  Q  A
214    CCCTGAGACTCTCCTGTGCAGCCTCTGGATTCACCTTCAGCGACTACACGATGAACTGGGTCCGCCAGGCG

P  G  K  G  L  E  W  V  S  S  I  S  G  G  S  T  Y  Y  A  D  S  R  K  G
285    CCCGGGAAGGGGCTGGAGTGGGTCTCATCCATTAGTGGTGGTAGCACATACTACGCAGACTCCAGGAAGGG

R  F  T  I  S  R  D  N  S  K  N  T  L  Y  L  Q  M  N  N  L  R  A  E
356    CAGATTCACCATCTCCAGAGACAATTCCAAGAACACGCTGTATCTTCAAATGAACAACCTGAGAGCTGAGG

D  T  A  V  Y  Y  C  A  R  D  R  Y  F  R  Q  Q  N  A  F  D  Y  W  G  Q
427    ACACGGCCGTGTATTACTGTGCAAGAGACCGCTACTTCAGGCAGCAGAACGCGTTCGATTACTGGGGCCAG

G  T  L  V  T  V  L  E  G  T  G  G  S  G  G  T  G  S  G  T  G  T  S  E
498    GGCACCCTGGTGACCGTGCTCGAGGGTACCGGAGGTTCCGGCGGAACCGGGTCTGGGACTGGTACGAGCGA

L  D  I  Q  M  T  Q  S  P  V  T  L  P  V  T  P  G  E  P  A  S  I  S
569    GCTCGACATCCAGATGACTCAGTCTCCAGTCACCCTGCCCGTCACCCCTGGAGAGCCGGCCTCCATCTCCT

C  R  S  S  Q  S  L  L  H  S  N  G  Y  N  Y  L  D  W  Y  L  Q  K  P  G
640    GCAGGTCTAGTCAGAGCCTCCTGCATAGTAATGGATACAACTATTTGGATTGGTACCTGCAGAAGCCAGGG

Q  S  P  Q  L  L  I  Y  L  G  S  N  R  A  S  G  V  P  D  R  F  S  G  S
711    CAGTCTCCACAGCTCCTGATCTATTTGGGTTCTAATCGGGCCTCCGGGGTCCCTGACAGGTTCAGTGGCAG

G  S  G  T  D  F  T  L  K  I  S  R  V  E  A  E  D  V  G  V  Y  Y  C
782    TGGATCAGGCACAGATTTTACACTGAAAATCAGCAGAGTGGAGGCTGAGGATGTTGGGGTTTATTACTGCC
                                                                        NotI
                                                                        --------
       Q  Q  Y  L  T  A  P  P  T  F  G  Q  G  T  K  L  E  I  K  R  A  A
853    AGCAGTACCTCACGGCCCCGCCCACCTTCGGCCAGGGCACCAAACTGGAAATCAAACGCGCGGCCGC
```

Figure 8

Anti-human OX40R scFv SC02012

```
                                                      NcoI
                                                      ------
                                        M  A  E  V  Q  L  V  E
72                                     CCATGGCTGAAGTGCAGCTGGTGGA

S  G  G  G  L  V  K  P  G  G  S  L  R  L  S  C  A  A  S  G  F  T  F  S
214     AAGCGGCGGCGGCCTGGTGAAGCCGGGTGGCAGCCTGCGCCTGAGCTGCGCCGCTAGCGGCTTCACCTTTA

N  D  S  M  N  W  M  R  Q  A  P  G  K  G  L  E  W  V  A  N  I  N  Q
214     GCAACGACTCGATGAACTGGATGCGCCAGGCCCCGGGCAAAGGCCTCGAATGGGTGGCCAATATCAATCAG

D  G  N  E  K  Y  Y  A  D  S  V  K  G  R  F  T  I  S  R  D  N  S  K  N
285     GATGGCAACGAAAAATATTACGCCGACTCTGTCAAAGGCCGCTTCACCATCAGTCGCGATAACTCCAAAAA

S  L  Y  L  Q  M  N  S  L  R  D  E  D  T  A  L  Y  Y  C  A  R  A  R
356     CTCCCTGTACCTGCAGATGAACAGCCTGCGCGACGAAGATACCGCCCTGTACTACTGCGCACGCGCCCGCG

A  A  G  T  I  F  D  Y  W  G  Q  G  T  L  V  T  V  L  E  G  T  G  G  S
427     CCGCCGGCACCATCTTCGATTACTGGGGCCAGGGCACCCTGGTGACCGTGCTCGAGGGTACCGGAGGTTCC

G  G  T  G  S  G  T  G  T  S  E  L  D  I  Q  M  T  Q  S  P  S  S  L  S
498     GGCGGAACCGGGTCTGGGACTGGTACGAGCGAGCTCGATATCCAGATGACCCAGAGCCCGAGTTCCCTGAG

A  S  V  G  D  R  V  T  I  T  C  R  A  S  Q  N  V  S  N  Y  L  T  W
569     CGCCTCCGTGGGCGACCGCGTGACCATCACCTGCCGCGCCAGCCAGAACGTCAGCAACTACCTGACCTGGT

Y  Q  Q  K  P  G  K  A  G  K  L  L  I  Y  A  A  S  S  L  Q  S  G  V  P
640     ACCAGCAGAAACCGGGCAAGGCTGGCAAACTGCTGATTTACGCCGCCAGCAGCCTCCAAAGCGGCGTGCCG

S  R  F  S  G  S  G  S  G  T  D  F  T  L  T  I  S  S  L  Q  P  E  D  F
711     TCTAGATTCAGTGGCTCCGGCTCCGGAACCGATTTTACCCTGACCATCAGCAGCCTGCAGCCGGAAGATTT

A  T  Y  Y  C  Q  Q  S  Y  F  N  P  A  T  F  G  Q  G  T  K  L  E  I
782     CGCTACCTACTATTGTCAGCAGTCCTACTTCAACCCGGCGACCTTCGGCCAGGGCACCAAACTGGAAATCA

NotI
                --------
            K  R  A  A
853     AACGCGCGGCCGC
```

Figure 9

Anti-human OX40R scFv SC02021

```
                              NcoI
                              ------
                              M  A  E  V  Q  L  V  E  S  G  G  G  L
143                           CCATGGCTGAGGTGCAGCTGGTGGAGTCTGGGGGAGGCTTG

V  Q  P  R  G  S  L  R  L  S  C  A  A  S  G  F  T  F  S  S  Y  A  M  N
214   GTACAGCCTAGGGGGTCCCTGAGACTCTCCTGTGCAGCCTCTGGATTCACCTTTAGCAGCTACGCGATGAA

W  V  R  Q  A  P  G  K  G  L  E  W  V  A  V  I  S  Y  D  G  S  N  K
285   CTGGGTCCGCCAGGCGCCCGGGAAGGGGCTGGAGTGGGTGGCAGTTATATCATATGATGGAAGCAATAAAT

Y  Y  A  D  S  V  K  G  R  F  T  I  S  R  D  N  S  K  N  T  L  Y  L  Q
356   ACTACGCAGACTCCGTGAAGGGCCGATTCACCATCTCCAGAGACAATTCCAAGAACACGCTGTATCTGCAA

M  N  S  L  R  A  E  D  T  A  V  Y  Y  C  A  K  D  R  Y  I  T  L  P  N
427   ATGAACAGCCTGAGAGCTGAGGACACAGCCGTGTATTACTGTGCCAAAGACCGCTACATCACGTTGCCGAA

A  L  D  Y  W  G  Q  G  T  L  V  T  V  L  E  G  T  G  G  S  G  G  T
498   CGCGTTGGATTACTGGGGCCAGGGCACCCTGGTGACCGTGCTCGAGGGTACCGGAGGTTCCGGCGGAACCG

G  S  G  T  G  T  S  E  L  D  I  Q  M  T  Q  S  P  V  S  L  P  V  T  P
569   GGTCTGGGACTGGTACGAGCGAGCTCGACATCCAGATGACCCAGTCTCCAGTCTCACTGCCCGTCACCCCT

G  E  P  A  S  I  S  C  R  S  S  Q  S  L  L  H  S  N  G  Y  N  Y  L  D
640   GGAGAGCCGGCCTCCATCTCCTGCAGGTCTAGTCAGAGCCTCCTGCATAGTAATGGATACAACTATTTGGA

W  Y  L  Q  K  P  G  Q  S  P  Q  L  L  I  Y  L  G  S  N  R  A  S  G
711   TTGGTACCTGCAGAAGCCAGGGCAGTCTCCACAGCTCCTGATCTATTTGGGTTCTAATCGGGCCTCCGGGG

V  P  D  R  F  S  G  S  G  S  G  T  D  F  T  L  K  I  S  R  V  E  A  E
782   TCCCTGACAGGTTCAGTGGCAGTGGATCAGGCACAGATTTTACACTGAAAATCAGCAGAGTGGAGGCTGAG

D  V  G  V  Y  Y  C  Q  Q  Y  K  S  N  P  P  T  F  G  Q  G  T  K  V  E
853   GATGTTGGGGTTTATTACTGCCAGCAGTACAAGTCGAACCCGCCCACCTTCGGCCAGGGCACCAAAGTGGA

NotI
                    --------
      I  K  R  A  A
924   AATCAAACGCGCGGCCGC
```

Figure 10

Anti-human OX40R scFv SC02022

```
                                                        NcoI
                                                        ~~~~~
                                       M  A  E  V  Q  L  V  E  S  G  G  G
72                                     CCATGGCCGAGGTGCAGCTGGTGGAGTCTGGGGGAGGC

L  V  H  P  G  G  S  L  R  L  S  C  A  G  S  G  F  T  F  S  S  Y  A  M
143    TTGGTACATCCTGGGGGGTCCCTGAGACTCTCCTGTGCAGGCTCTGGATTCACCTTCAGTAGCTATGCTAT

H  W  V  R  Q  A  P  G  K  G  L  E  W  V  S  A  I  G  T  G  G  G  T
214    GCACTGGGTTCGCCAGGCTCCAGGAAAAGGTCTGGAGTGGGTATCAGCTATTGGTACCGGTGGTGGCACAT

Y  Y  A  D  S  V  Q  G  R  F  T  I  S  R  D  N  A  K  N  S  L  Y  L  Q
285    ACTATGCAGACTCCGTGCAGGGCCGATTCACCATCTCCAGAGACAATGCCAAGAACTCCTTGTATCTTCAA

M  N  S  L  R  A  E  D  T  A  V  Y  Y  C  A  R  Y  D  E  P  L  T  I  Y
356    ATGAACAGCCTGAGAGCCGAGGACACGGCCGTGTATTACTGTGCAAGATACGACGAGCCGCTGACGATTTA

W  F  D  S  W  G  Q  G  T  L  V  T  V  S  S  G  G  G  G  S  G  G  G
427    CTGGTTTGACTCCTGGGGCCAAGGTACCCTGGTCACCGTCTCGAGTGGTGGAGGCGGTTCAGGCGGAGGTG

G  S  G  G  G  G  S  E  I  E  L  T  Q  S  P  A  T  L  S  L  S  P  G  E
498    GCTCTGGCGGTGGCGGATCGGAAATTGAGCTCACACAGTCTCCAGCCACCCTGTCTTTGTCTCCAGGGGAA

R  A  T  L  S  C  R  A  S  Q  S  V  S  S  Y  L  A  W  Y  Q  Q  K  P  G
569    AGAGCCACCCTCTCCTGCAGGGCCAGTCAGAGTGTTAGCAGCTACTTAGCCTGGTACCAACAGAAACCTGG

Q  A  P  R  L  L  I  Y  D  A  S  N  R  A  T  G  I  P  A  R  F  S  G
640    CCAGGCTCCCAGGCTCCTCATCTATGATGCATCCAACAGGGCCACTGGCATCCCAGCCAGGTTCAGTGGCA

S  G  S  G  T  D  F  T  L  T  I  S  S  L  E  P  E  D  F  A  V  Y  Y  C
711    GTGGGTCTGGGACAGACTTCACTCTCACCATCAGCAGCCTAGAGCCTGAAGATTTTGCAGTTTATTACTGT
                                                                          NotI
                                                                          ~~~~~
           Q  Q  R  S  N  W  P  P  A  F  G  G  G  T  K  V  E  I  K  R  A  A
782    CAGCAGCGTAGCAACTGGCCTCCGGCTTTCGGCGGAGGGACCAAGGTGGAGATCAAACGTGCGGCCGC
```

Figure 11

Anti-human OX40R scFv SC02023

```
                                                  NcoI
                                                  ~~~~~~
                                                  M  A  E  V  Q  L  V  E
72                                                CCATGGCCGAGGTGCAGCTGGTGGAG

S  G  G  G  L  V  H  P  G  G  S  L  R  L  S  C  A  G  S  G  F  T  F  S
143  TCTGGGGGAGGCTTGGTACATCCTGGGGGGTCCCTGAGACTCTCCTGTGCAGGCTCTGGATTCACCTTCAG

S  Y  A  M  H  W  V  R  Q  A  P  G  K  G  L  E  W  V  S  A  I  G  T
214  TAGCTATGCTATGCACTGGGTTCGCCAGGCTCCAGGAAAAGGTCTGGAGTGGGTATCAGCTATTGGTACTG

G  G  G  T  Y  Y  A  D  S  V  M  G  R  F  T  I  S  R  D  N  S  K  N  T
285  GTGGTGGCACATACTATGCAGACTCCGTGATGGGCCGGTTCACCATCTCCAGAGACAATTCCAAGAACACG

L  Y  L  Q  M  N  S  L  R  A  E  D  T  A  V  Y  Y  C  A  R  Y  D  N  V
356  CTGTATCTGCAAATGAACAGCCTGAGAGCCGAGGACACGGCCGTGTATTACTGTGCAAGATACGACAATGT

M  G  L  Y  W  F  D  Y  W  G  Q  G  T  L  V  T  V  S  S  G  G  G  G
427  GATGGGTCTTTACTGGTTTGACTACTGGGGCCAAGGTACCCTGGTCACCGTCTCGAGTGGTGGAGGCGGTT

S  G  G  G  G  S  G  G  G  G  S  E  I  E  L  T  Q  S  P  A  T  L  S  L
498  CAGGCGGAGGTGGCTCTGGCGGTGGCGGATCGGAAATTGAGCTCACACAGTCTCCAGCCACCCTGTCTTTG

S  P  G  E  R  A  T  L  S  C  R  A  S  Q  S  V  S  S  Y  L  A  W  Y  Q
569  TCTCCAGGGGAAAGAGCCACCCTCTCCTGCAGGGCCAGTCAGAGTGTTAGCAGCTACTTAGCCTGGTACCA

Q  K  P  G  Q  A  P  R  L  L  I  Y  D  A  S  N  R  A  T  G  I  P  A
640  ACAGAAACCTGGCCAGGCTCCCAGGCTCCTCATCTATGATGCATCCAACAGGGCCACTGGCATCCCAGCCA

R  F  S  G  S  G  S  G  T  D  F  T  L  T  I  S  S  L  E  P  E  D  F  A
711  GGTTCAGTGGCAGTGGGTCTGGGACAGACTTCACTCTCACCATCAGCAGCCTAGAGCCTGAAGATTTTGCA

V  Y  Y  C  Q  Q  R  S  N  W  P  P  A  F  G  G  G  T  K  V  E  I  K  R
782  GTTTATTACTGTCAGCAGCGTAGCAACTGGCCTCCGGCTTTCGGCGGAGGGACCAAGGTGGAGATCAAACG

NotI
     ~~~~~~~~~
     A  A
853  TGCGGCCGC
```

Figure 12

5' Cloning site of pPicZαB

```
                    KEK2
                  Cleavage
                    site
       XhoI                              EcoRI            SfiI
      ~~~~~~         ↓                   ~~~~~~      ~~~~~~~~~~~~~~
       S   L   E    K   R   E   A   E   A    G   I   H   V   A   Q   P   A
1151  TCTCTCGAGA AAAGAGAGGC TGAAGCTGCA GGAATTCACG TGGCCCAGCC GGCCG
      AGAGAGCTCT TTTCTCTCCG ACTTCGACGT CCTTAAGTGC ACCGGGTCGG CCGGC
```

5' Cloning site of pPicZFVH

```
                    KEK2
                  Cleavage
                    site
       XhoI         ↓    NcoI           EcoRI            SfiI
      ~~~~~~            ~~~~~           ~~~~~~      ~~~~~~~~~~~~~~
       S   L   E    K   R   A   M   E   A   A    G   I   H   V   A   Q   P   A
1151  TCTCTCGAGA AAAGAGCCATGGAAGCTGCA GGAATTCACG TGGCCCAGCC GGCCG
      AGAGAGCTCT TTTCTCGGTACCTTCGACGT CCTTAAGTGC ACCGGGTCGG CCGGC
``` synthetic hinge fragment

Cysteine residues available for disulphide bonding

```
                        Flexible upper
         ←              hinge region
        NotI           _____                  ↙      ↘
      ~~~~~~~~
         A   A   A   P   K   P   S   T   P   P   G   S   S   C   P   P   C
    1   GCGGCCGCGC CAAAGCCAAG TACCCCACCA GGTTCTTCAT GTCCACCATG
        CGCCGGCGCG GTTTCGGTTC ATGGGGTGGT CCAAGAAGTA CAGGTGGTAC Short linker         ClaI           XbaI
        _____        ~~~~~~         ~~~~~~
         P   G   S   G   G   A   P   I   D   S   G   F   L
    51  TCCAGGCTCT GGCGGTGCGC CAATCGATAG CGGCTTTCTA GA
        AGGTCCGAGA CCGCCACGCG GTTAGCTATC GCCGAAAGAT CT
```

Figure 13C

ANTIBODY TO THE HUMAN OX40 RECEPTOR

CROSS-REFERENCE TO RELATED APPLICATION

This is a national phase entry under 35 U.S.C. § 371 of International Patent Application No. PCT/EP03/06341, filed Jun. 13, 2003, published in English as International Patent Publication No. WO 03/106498 on Dec. 24, 2003, which claims the benefit under 35 U.S.C. § 119 of International Patent Application No. PCT/NL02/00389 filed Jun. 13, 2002.

STATEMENT ACCORDING TO 37 C.F.R. § 1.52(e)(5) SEQUENCE LISTING SUBMITTED ON COMPACT DISC

Pursuant to 37 C.F.R. § 1.52(e), a compact disc containing an electronic version of the SEQUENCE LISTING has been submitted, the contents of which are hereby incorporated by reference. A second compact disk is submitted and is an identical copy of the first compact disc. The discs are labeled "Replacement Copy 1"and "Replacement Copy 2,"respectively, and each disc contains one file entitled "0077 (0X40) Nov 11, 2005 version.ST25.txt"which is 90 KB and was created on Nov. 11, 2005 and has a recordation date of Nov. 16, 2005.

FIELD OF THE INVENTION

The present invention relates generally to the field of biotechnology and more specifically to the field of medicine, more in particular, to agonistic binding molecules capable of specifically binding to the human OX40-receptor. The binding molecules are useful in immunotherapy.

BACKGROUND

The OX40-receptor (OX40R) (also known as CD134, ACT-4, ACT35) is a member of the TNF receptor family which is expressed on activated CD4+ T-cells (see WO 95/12673). Triggering of this receptor via the OX40-ligand, named OX40L, gp34 or ACT-4-ligand, present on activated B-cells and dendritic cells, enhances the proliferation of CD4+ T-cells during an immune response and influences the formation of CD4+ memory T-cells. Furthermore, the OX40R-OX40L system mediates adhesion of activated T-cells to endothelial cells, thus directing the activated CD4+ T-cells to the site of inflammation.

Inflammatory and autoimmune diseases, such as rheumatoid arthritis and inflammatory bowel disease, are characterized by an infiltration of activated T-cells at the site of inflammation, which is believed to orchestrate the response leading to chronic tissue destruction. In patients with inflammatory bowel disease, OX40+ CD4+ T-cells can be found in the gut associated with sites of inflammation. In addition, in patients suffering from acute graft-vs-host-disease, elevated levels of OX40+ peripheral CD4+ T-cells are present in peripheral blood. In rheumatoid arthritis patients, OX40+ CD4+ T-cells are present in synovial fluid, while they are virtually absent from peripheral blood. Furthermore, OX40+ CD4+ T-cells are found in inflamed synovial tissue in addition to cells expressing the ligand for the OX40-receptor. This is in contrast to patients suffering from osteoarthritis, a joint disease that is not mediated by inflammation, where both cell types could not be found in significant numbers.

Thus, in patients suffering from several inflammatory disorders elevated levels of OX40+ CD4+ T-cells are present at sites of inflammation, indicating that these cells may be involved in progression of autoimmune disease. A blockade of the OX40R-OX40L pathway using antibodies or fusion proteins has led to the attenuation of disease progression in several animal models of autoimmune disease.

Besides their presence in autoimmune diseases, it has been shown that OX40+ T-cells are present within tumor lesions containing tumor infiltrating lymphocytes and in tumor cell positive draining lymph nodes (Weinberg et al., 2000). It was shown in several tumor models in mice that engagement of the OX40-receptor in vivo during tumor priming significantly delayed and prevented the appearance of tumors as compared to control treated mice (Weinberg et al., 2000). Hence, it has been contemplated to enhance the immune response of a mammal to an antigen by engaging the OX40-receptor by administering an OX40-receptor binding agent (WO 99/42585; Weinberg et al., 2000). One possibility is to use a natural ligand of the OX40-receptor, i.e. the OX40-ligand, or fusion proteins thereof as an OX40-receptor binding ligand. Such proteins however have a fixed affinity for the receptor that is not easily changed, may not have the circulatory retention time to exert the desired therapeutic effect, and may give rise to immunogenicity (Weinberg et al., 2000).

Another possibility to stimulate T-cells by virtue of the OX40-receptor pathway, is to use antibodies against this receptor (Kaleeba et al., 1998; Weinberg et al., 2000). A rat anti-mouse OX40-receptor antibody named OX86 (Al-Shamkhani et al., 1996) appeared to engage the OX40-receptor in murine tumor models (Weinberg et al., 2000; U.S. Pat. No. 6,312,700).

To our knowledge agonistic antibodies, particularly human agonistic antibodies, that are capable of stimulating the human OX40-receptor have not been disclosed in the art. Furthermore, it is well known that non-human antibodies are limited in their use in vivo in humans. Problems associated with administration of non-human antibodies to humans are inter alia short serum half life, an inability to trigger certain human effector functions and elicitation of an unwanted dramatic immune response against the non-human antibody in a human.

In general, attempts to overcome the problems associated with use of fully non-human antibodies in humans, have involved genetically engineering the antibodies to be more "human-like". A first stage in the humanization process was preparing chimeric antibodies, i.e. antibodies in which the variable regions of the antibody chains are derived from the non-human species and the constant regions of the antibody chains are human-derived. Subsequently, domains between the variable domains which specify the antigen binding were replaced by their human counterparts leading to so-called humanized antibodies. A disadvantage of these chimeric and humanized antibodies is that they still retain some non-human sequences and therefore still elicit an unwanted immune reaction, especially when administered for prolonged periods.

In the light of the above, there is still a need for human antibodies that stimulate the human OX40-receptor. These antibodies can be useful in inter alia the treatment and/or prevention of tumours in humans.

SUMMARY OF THE INVENTION

The invention provides agonistic binding molecules capable of specifically binding to the human OX40-receptor.

In a preferred embodiment, said binding molecules are human binding molecules. Furthermore, the invention pertains to nucleic acid molecules encoding at least the binding region of the binding molecules. The invention further provides for the use of the binding molecules or nucleic acids for enhancing the immune response in a human, for use in the treatment of the human or animal body, and for the preparation of a medicament to treat a human having or at risk of developing a disorder or disease such as a neoplastic disorder or disease.

DESCRIPTION OF THE FIGURES

In FIG. 3 the binding of anti-human OX40-receptor phage antibodies, selected using immobilized human OX40-Ig fusion protein, to OX40+ CD4+ T-cells is shown.

FIG. 5 shows the nucleotide sequence (SEQ ID NO:1) and amino acid sequence (SEQ ID NO:2) of the scFv called SC02008. The heavy chain CDR3 region is underlined.

FIG. 6 shows the nucleotide sequence (SEQ ID NO:3) and amino acid sequence (SEQ ID NO:4) of the scFv called SC02009. The heavy chain CDR3 region is underlined.

FIG. 7 shows the nucleotide sequence (SEQ ID NO:5) and amino acid sequence (SEQ ID NO:6) of the scFv called SC02010. The heavy chain CDR3 region is underlined.

FIG. 8 shows the nucleotide sequence (SEQ ID NO:7) and amino acid sequence (SEQ ID NO:8) of the scFv called SC02011. The heavy chain CDR3 region is underlined.

FIG. 9 shows the nucleotide sequence (SEQ ID NO:9) and amino acid sequence (SEQ ID NO:10) of the scFv called SC02012. The heavy chain CDR3 region is underlined.

FIG. 10 shows the nucleotide sequence (SEQ ID NO:11) and amino acid sequence (SEQ ID NO:12) of the scFv called SC02021. The heavy chain CDR3 region is underlined.

FIG. 11 shows the nucleotide sequence (SEQ ID NO:13) and amino acid sequence (SEQ ID NO:14) of the scFv called SC02022. The heavy chain CDR3 region is underlined.

FIG. 12 shows the nucleotide sequence (SEQ ID NO:15) and amino acid sequence (SEQ ID NO:16) of the scFv called SC02023. The heavy chain CDR3 region is underlined.

FIG. 14 shows the functional activity of the anti-human OX40-receptor bivalent scFv's SC02008 and SC02023 in an in vitro T-cell costimulation assay.

DETAILED DESCRIPTION OF THE INVENTION

Figure 1:
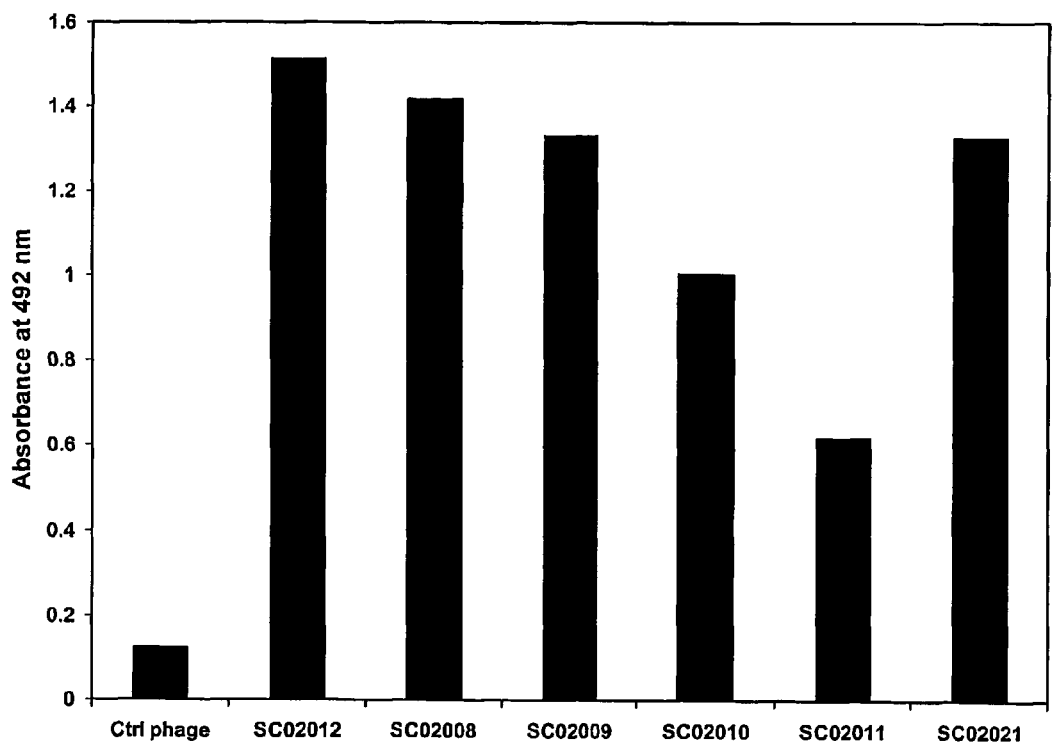
FIG. 1 shows the binding of anti-human OX40-receptor phage antibodies, that were selected using immobilized human OX40-Ig fusion protein, to human OX40-Ig fusion protein coated to ELISA plates. The Y-axis shows the absorbance at 492 nm.

Herebelow follow definitions of terms as used in the invention

Definitions

Agonistic Binding Molecule

The term "agonistic binding molecule" as used herein in general refers to a binding molecule which, when combined with a receptor, e.g. the OX40-receptor, on a cell, is capable of binding to the receptor and is capable of initiating/mimicking/stimulating a reaction or activity that is similar to or the same as that initiated/mimicked/stimulated by the receptor's natural ligand, e.g. the OX40-ligand. An agonistic binding molecule of the OX40-receptor is capable of immunospecifically binding to the OX40-receptor expressed by activated CD4+ T-cells, and is capable of inducing/augmenting/enhancing/stimulating the activation of a signal transduction pathway associated with the OX40-receptor such as for instance the activation of the activated CD4+ T-cells.

Agonistic binding molecules are capable of inducing/augmenting/enhancing/stimulating any or all of, but not limited to, the following responses: proliferation of CD4+ T-cells during an immune response, stimulation of cytokine production, proliferation of Th1 or Th2 effector cells, development of a Th2 response, generation of CD4+ memory T cells. An agonistic binding molecule may induce/enhance/stimulate/augment any one or more of the responses by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. In particular, an agonistic binding molecule that is capable of inducing/enhancing/stimulating/augmenting an activated CD4+ T-cell activates an activated CD4+ T-cell 1-5 fold, 5-10 fold, 10-20 fold, or more than 20 fold as compared to the ability of the agonistic binding molecule to activate a resting T-cell, i.e. T-cells which do not express or express low to undetectable levels of the T-cell activation marker CD4. Methods for determining the activation/stimulation/induction/enhancement are known in the art and include, but are not limited to, antigen specific proliferation assays, cytokine ELISA assays, elispot assays, detection of antigen specific T-cells using flow cytometry methods employing Major Histocompatibility Complex (MHC) peptide tetramers. The agonistic binding molecules are preferably against epitopes within the extracellular domain of the OX40-receptor. The term "agonistic binding molecule" as used herein covers inter alia agonistic human anti-OX40-receptor monoclonal antibodies or parts thereof and agonistic human anti-OX40-receptor compositions with polyepitopic specificity.

Amino Acid Sequence

The term "amino acid sequence" as used herein refers to naturally occurring or synthetic molecules and to a peptide, oligopeptide, polypeptide or protein sequence.

Binding Molecule

As used herein the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g. OX40-receptor. Regardless of structure, the antigen-binding fragment binds with the same antigen that is recognized by the intact immunoglobulin. An antigen-binding fragment can comprise a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least 200 contiguous amino acid residues, or at least contiguous 250 amino acid residues of the amino acid sequence of the binding molecule.

The term "binding molecule", as used herein also includes the immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')2, Fv, dAb, Fd, complementarity determining region (CDR) fragments, single-chain antibodies (scFv), bivalent single-chain antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, or an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in vivo.

Complementary Determining Regions (CDR)

The term "complementary determining regions" as used herein means sequences within the variable regions of binding molecules, such as immunoglobulins, that generate the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of posttranslational modifications of proteins.

Deletion

The term "deletion", as used herein, denotes a change in either amino acid or nucleotide sequence in which one or more amino acid or nucleotide residues, respectively, are absent as compared to the parent, often the naturally occurring, molecule.

Expression-regulating Nucleic Acid Sequence

The term "expression-regulating nucleic acid sequence" as used herein refers to polynucleotide sequences necessary for and/or affecting the expression of an operably linked coding sequence in a particular host organism. Generally, when two nucleic acid sequences are operably linked, they will be in the same orientation and usually also in the same reading frame. They usually will be essentially contiguous, although this may not be required. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism.

Functional Variant

The term "functional variant", as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g. OX40-receptor, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e. the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host

The term "host", as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human

The term "human", when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences based on variable or constant regions either or not occurring in a human or human lymphocyte or in modified form. Thus, the human binding molecules may include amino acid residues not encoded by human germline immunoglobulin sequences, comprise substitutions and/or deletions (e.g., mutations introduced by for instance random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semisynthetic molecules based on human sequences are also considered to be human as used herein.

Immune Response

The term "immune response" as used herein refers to an antagonistic and specific host reaction in response to foreign or self antigens, involving the formation of antibodies by B-cells or a cell-mediated response by T-cells.

Insertion

The term "insertion", also known as the term "addition", denotes a change in an amino acid or nucleotide sequence resulting in the addition of one or more amino acid or nucleotide residues, respectively, as compared to the parent, often the naturally occurring, molecule.

Internalizing Binding Molecule

The term "internalizing binding molecule" as used herein means a binding molecule as defined herein that is capable of being internalized within the target cells to which it binds. In other words, the binding molecule is taken up, i.e. transported from the outside (cell surface) of a target cell to the inside, e.g. into the endosomal compartment or other compartment or into the cytoplasm of the cell, by the target cells upon binding to the binding partner of the binding molecule.

Isolated

The term "isolated", when applied to binding molecules as defined herein, refers to binding molecules that are substantially free of other proteins or polypeptides, particularly free of other binding molecules having different antigenic specificities, and are also substantially free of other cellular or tissue material and/or chemical precursors or other chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. Preferably, substantially free means that the binding molecule will typically comprise about 50%, 60%, 70%, 80% or 90% W/W of a sample, more usually about 95%, and preferably will be over 99% pure.

The term "isolated" when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than the OX40-receptor. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as a cDNA molecules, can be substantially free of other cellular material, or culture medium when produced by recombinant techniques, or substantially free of chemical precursors or other chemicals when chemically synthesized.

Monoclonal Antibody

The term "monoclonal antibody" as used herein refers to a preparation of antibody molecules of single molecular composition. A monoclonal antibody displays a single binding specificity and affinity for a particular epitope. Accordingly, the term "human monoclonal antibody" refers to an antibody displaying a single binding specificity which have variable and constant regions derived from or based on human germline immunoglobulin sequences or derived from completely synthetic sequences.

Naturally Occurring

The term "naturally-occurring" as used herein as applied to an object refers to the fact that an object can be found in nature. For example, a polypeptide or polynucleotide sequence that is present in an organism that can be isolated from a source in nature and which has not been intentionally modified by man in the laboratory is naturally-occurring.

Neoplastic Cells

The term "neoplastic cells" as used herein refers to cells that result from abnormal autonomous new growth which has no apparent physiological function. A neoplastic cell further includes transformed cells and cancer cells including blood cancers (benign and malignant).

Nucleic Acid Molecule

The term "nucleic acid molecule" as used in the present invention refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally-occurring and modified nucleotides linked together by naturally-occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

Operably Linked

The term "operably linked" refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

Pharmaceutically Acceptable Excipient

By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed and is compatible with other ingredients of the formulation comprising the drug, agent or binding molecule.

Specifically Binding

The term "specifically binding", as used herein, in reference to the interaction of a binding molecule, e.g. an antibody, and its binding partner, e.g. an antigen, means that the interaction is dependent upon the presence of a particular structure, e.g. an antigenic determinant or epitope, on the binding partner. In other words, the antibody preferentially binds or recognizes the binding partner even when the binding partner is present in a mixture of other molecules. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme-linked immunosorbent assays (ELISA), BIAcore, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

Substitutions

A "substitution", as used herein, denotes the replacement of one or more amino acids or nucleotides by different amino acids or nucleotides, respectively.

Therapeutically Effective Amount

The term "therapeutically effective amount" refers to an amount of the binding molecule as defined herein that is effective for preventing, ameliorating or treating a disorder or disease wherein the OX40-receptor molecules play a role or are associated with.

Treatment

The term "treatment" refers to therapeutic treatment as well as prophylactic or preventative measures to cure or halt or at least retard disease progress. Those in need of treatment include those already inflicted with a disease or disorder wherein OX40-receptor molecules play a role or are associated with as well as those in which the disease or disorder is to be prevented. Prevention encompasses inhibiting or reducing the spread of the disease or disorder or inhibiting or reducing the onset, development or progression of one or more of the symptoms associated with the disease or disorder wherein OX40-receptor molecules play a role or are associated with.

Vector

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector", as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., bacterial vectors having a bacterial origin of replication). Other vectors can be integrated into the genome of a host upon introduction into the host, and thereby are replicated along with the host genome.

In a first aspect, the present invention provides agonistic binding molecules, capable of binding, preferably specifically binding, to or capable of associating with the human OX40-receptor. The agonistic binding molecules are also capable of binding, particularly specifically binding, to a fragment of the human OX40-receptor, the fragment at least comprising an antigenic determinant of the human OX40-receptor that is recognized by at least one of the agonistic binding molecules of the invention. The human OX40-receptor is selectively expressed by activated immune cells, such as activated CD4+ T-cells. The binding molecules of the invention are capable of stimulating and/or activating and/or enhancing and/or augmenting and/or inducing activated CD4+ T-cells. The expression of CD4 on activated T-cells can be measured by methods known in the art, including, but not limited to, FACS analysis, immunofluorescence assays, RT-PCR, Northern blot analysis and Western blot analysis.

In a preferred embodiment, the agonistic binding molecules according to the invention are human agonistic binding molecules. Preferably, the human binding molecules are derived from a semisynthetic library based on human sequences and mutated using error-prone PCR to increase specificities. A human binding molecule according to the invention such as an antibody lacks murine-derived sequences, in contrast to mouse antibodies obtained by hybridoma technology (Kohler and Milstein, 1975), or variants thereof such as chimeric antibodies or humanized antibodies. Human antibodies have the advantage that when administered to humans an anti-antibody immunogenic response will be extremely low or absent, whereas the murine derived antibodies can give rise to such responses quite extensively (Van Kroonenburgh and Pauwels, 1988). A binding molecule is for instance based upon a human sequence when it has been obtained from a library of human binding molecules. Such a library may also comprise human binding molecules that are based upon a human sequence but containing mutations, e.g. a semi-synthetic library, as was used to obtain molecules according to the present invention. 'Based upon' as used herein, is meant to include the synthetic construction of genetic information based upon knowledge of such genetic information. Such methods include the use of human or human derived genetic material as a template for PCR to construct a new binding molecule encoding construct that is based upon the sequence of the template, the construction of completely synthetic genetic information with a desired sequence e.g. by linking synthetic oligonucleotides to a desired construct, and the like. It is to be understood that 'based upon' does not exclusively mean a direct cloning of the wild type DNA. A person skilled in the art will also be aware of the possibilities of molecular biology to obtain mutant forms of a certain piece of nucleic acid.

The agonistic binding molecules of the invention can be intact immunoglobulin molecules such as polyclonal or monoclonal antibodies, in particular human monoclonal antibodies, or the binding molecules can be antigen-binding fragments including, but not limited to, Fab, F(ab'), F(ab')2, Fv, dAb, Fd, complementarity determining region (CDR) fragments, single-chain antibodies (scFv), bivalent single-chain antibodies, diabodies, triabodies, tetrabodies, and (poly)peptides that contain at least a fragment of an immunoglobulin that is sufficient to confer specific antigen binding to the (poly)peptides. The agonistic binding molecules of the invention can be used in non-isolated or isolated form. Furthermore, the agonistic binding molecules of the invention can be used alone or in a mixture/composition comprising at least one agonistic binding molecule (or variant or fragment thereof) of the invention. The mixture/composition may further comprise at least one other therapeutic agent. In one embodiment, the therapeutic agent can be a natural ligand of the OX40-receptor or a variant of the natural ligand still capable of binding to the human OX40-receptor. The agonistic binding molecules of the invention can act synergistically in vitro with the natural ligand, e.g. OX40-ligand. An advantage of agonistic binding molecules acting synergistically with the natural ligand could be that they may enhance the effect of OX40-ligand present in vivo, rather than only substituting it. Such synergistic activity can be determined by a functional assays known to the skilled artisan.

Typically, agonistic binding molecules according to the invention can bind to their binding partners, i.e. the human OX40-receptor, with an affinity constant (Kd-value) that is lower than $0.2 \times 10^{-4}$ M, $1.0 \times 10^{-5}$ M, $1.0 \times 10^{-6}$ M, $1.0 \times 10^{-6}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and in particular lower than $1.0 \times 10^{-12}$ M. The affinity constants can vary for antibody isotypes. For example, affinity binding for an IgM isotype refers to a binding affinity of at least about $1.0 \times 10^{-7}$ M. Affinity constants can be measured using surface plasmon resonance, i.e. an optical phenomenon that allows for the analysis of real-time biospecific interactions by detection of alterations in protein concentrations within a biosensor matrix, for example using the BIAcore system (Pharmacia Biosensor AB, Uppsala, Sweden).

The agonistic binding molecule of the invention may internalize upon binding to the human OX40-receptor. Furthermore, the agonistic binding molecules according to the invention may bind to the human OX40-receptor in soluble form or may bind to the human OX40-receptor bound or attached to a carrier or substrate, e.g., microtiter plates, membranes and beads, etc. Carriers or substrates may be made of glass, plastic (e.g., polystyrene), polysaccharides, nylon, nitrocellulose, or teflon, etc. The surface of such supports may be solid or porous and of any convenient shape. Furthermore, the agonistic binding molecules may bind to the human OX40-receptor in purified or non-purified form. Preferably, the agonistic binding molecules are capable of specifically binding to the human OX40-receptor associated with cells, such as activated CD4+ T-cells or portions or parts of these cells comprising the human OX40-receptor or a fragment thereof.

In another embodiment, the binding molecules of the invention comprises at least a CDR3 region comprising the amino acid sequence selected from the group consisting of SEQ ID NO:17 (DRYSQVHYALDY), SEQ ID NO:18 (DRYVNTSNAFDY), SEQ ID NO:19 (DMSGFHEFDY), SEQ ID NO:20 (DRYFRQQNAFDY), SEQ ID NO:21 (ARAAGTIFDY), SEQ ID NO:22 (DRYITLPNALDY), SEQ ID NO:23 (YDEPLTIYWFDS) and SEQ ID NO:24 (YDNVMGLYWFDY).

In yet another aspect, the invention provides binding molecules of the invention comprising a heavy chain comprising the amino acid sequence selected from the group consisting of SEQ ID NO:25, SEQ ID NO:26, SEQ ID NO:27 and SEQ ID NO:28. In a further embodiment the invention pertains to binding molecules comprising a heavy chain comprising the amino acid sequence of SEQ ID NO:25 and a light chain comprising the amino acid sequence of SEQ ID NO:29, a heavy chain comprising the amino acid sequence of SEQ ID NO:26 and a light chain comprising the amino acid sequence of SEQ ID NO:30, a heavy chain comprising the amino acid sequence of SEQ ID NO:27 and a light chain comprising the amino acid sequence of SEQ ID NO:31 or a heavy chain comprising the amino acid sequence of SEQ ID NO:28 and a light chain comprising the amino acid sequence of SEQ ID NO:32.

Another aspect of the invention includes functional variants of agonistic binding molecules or fragments thereof as defined herein. Molecules are functional variants of a binding molecule, when the variants are capable of competing for specifically binding to the human OX40-receptor, preferably competing for the same binding site on the human OX40-receptor, with the parent binding molecules. In other words, when the functional variants are still capable of immunospecifically binding to the human OX40-receptor or a portion thereof. Furthermore, the functional variants must be capable of inducing/stimulating/enhancing/augmenting activated CD4+ T-cells. In other words, the functional variants must also have agonistic activity. This agonistic activity can be higher or lower than the agonistic activity of the parent binding molecules of the invention. Functional variants include, but are not limited to, derivatives that are substantially similar in primary structural sequence, but which contain e.g. in vitro or in vivo modifications, chemical and/or biochemical, that are not found in the parent binding molecule. Such modifications include inter alia acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Alternatively, functional variants can be binding molecules as defined in the present invention comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxy termini. Functional variants according to the invention may have the same or different, either higher or lower, binding affinities compared to the parent binding molecule but are still capable of binding to the human OX40-receptor present on e.g. a CD4+ T-cell. For instance, functional variants according to the invention may have increased or decreased binding affinities for the human OX40-receptor compared to the parent binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the present invention have at least 50%, preferably at least 60%, at least 70%, at least 75%, more preferably at least 80%, at least 85%, even more preferably at least 90%, at least 95%, and in particluar at least 97%, at least 98%, at least 99% amino acid sequence homology with the parent binding molecules as defined herein. Computer algorithms such as inter alia Gap or Bestfit known to a person skilled in the art can be used to optimally align amino acid sequences to be compared and to define similar or identical amino acid residues.

Functional variants of the invention can be obtained by altering the nucleotide sequence of parent binding molecules or parts thereof by general molecular biology methods known in the art including, but not limited to, error-prone PCR, oligonucleotide-directed mutagenesis and site-directed mutagenesis. Mutations in the nucleotide sequences may render a different functionality, but they may also be silent in a way that certain mutations do not alter the functionality of that particular piece of DNA and its encoded protein. A person skilled in the art will appreciate the fact that certain deletions, swaps, (point)mutations, additions, substitutions etc. may still result in a nucleic acid that has a similar function as the original nucleic acid. It is therefore to be understood that such alterations that do not significantly alter the functionality of the encoded agonistic binding molecules against the human OX40-receptor are within the scope of the present invention. Human antibodies according to the invention may therefore also contain (semi-)synthetic regions, e.g. in the CDR regions. It is for instance possible to alter the CDR regions of the variable domains of binding molecules by site-directed mutagenesis, oligo-directed mutagenesis, error-prone PCR, cloning of restriction fragments, and the like.

In yet a further aspect, the invention includes immunoconjugates, i.e. molecules comprising at least one agonistic binding molecule as defined herein and further comprising at least one tag, such as a therapeutic moiety. Also contemplated in the present invention are mixtures of immunoconjugates according to the invention or mixtures of at least one immunoconjugates according to the invention and another molecule, such as a therapeutic agent or another binding molecule. In an embodiment, the immunoconjugates of the invention comprise more than one tag. These tags can be the same or distinct from each other and can be joined/conjugated non-covalently to the binding molecules. The tags can be joined/conjugated directly to the binding molecules through covalent bonding, including, but not limited to, disulfide bonding, hydrogen bonding, electrostatic bonding, recombinant fusion and conformational bonding. Alternatively, the tags can be joined/conjugated to the binding molecules by means of one or more linking compounds. Techniques for conjugating tags to binding molecules, are well known, see, e.g., Arnon et al., Monoclonal Antibodies For Immunotargeting Of Drugs In Cancer Therapy, p. 243-256 in Monoclonal Antibodies And Cancer Therapy (1985), Edited by: Reisfeld et al., A. R. Liss, Inc.; Hellstrom et al., Antibodies For Drug Delivery, p. 623-653 in Controlled Drug Delivery, 2$^{nd}$ edition (1987), Edited by: Robinson et al., Marcel Dekker, Inc.; Thorpe, Antibody Carriers Of Cytotoxic Agents, p. 475-506 In Cancer Therapy: A Review, in Monoclonal Antibodies' 84 : Biological And Clinical Applications (1985), Edited by: Pinchera et al.; Analysis, Results, And Future Prospective Of The Therapeutic Use Of Radiolabeled Antibody In Cancer Therapy, p. 303-316 in Monoclonal Antibodies For Cancer Detection And Therapy (1985), Edited by: Baldwin et al., Academic Press.

In a specific embodiment, the tags comprise a compound that further enhances the immune response, such as a compound that stimulates and/or activates and/or enhances and/or augments and/or induces activated immune cells, e.g. activated T-cells such as activated CD4+ T-cells. Such compounds may include, but are not limited to, binding molecules, small molecules, organic or inorganic compounds, enzymes, polynucleotide sequences, plasmids, proteins, peptides, liposomes or combinations thereof. Examples of compounds capable of enhancing the immune response include, but are not limited to, compounds that activate a cytokine receptor such as inter alia cytokines including, but not limited to, CSF-1, Flt3 ligand, G-CSF, GM-CSF, IFN-α, IFN-β, IFN-γ, IL-1β, IL-2, IL-3, IL-4, IL-5, IL-6, IL-7, IL-8, IL-9, IL-10, IL-12, IL-15, IL-18, M-CSF, and TNF-α; chemokines including, but not limited to, IP-10, MIG, and MIP-1; binding molecules that immunospecifically bind to a receptor including, but not limited to, the CSF-1 receptor, Flt3, G-CSF receptor, GM-CSF receptor, IFN-α receptor, IFN-β receptor, IFN-γ receptor, IL-1β receptor, IL-2 receptor, IL-3 receptor, IL-4 receptor, IL-5 receptor, IL-6 receptor, IL-7 receptor, IL-8 receptor, IL-9 receptor, IL-10 receptor, IL-12 receptor, IL-15 receptor, IL-18 receptor, IP-10 receptor, M-CSF receptor, MIG receptor, MIP-1 receptor, and TNF-α receptor. Analogs, derivatives or fragments of the above listed compounds which are still functional, i.e. are capable of stimulating and/or activating and/or enhancing and/or augmenting and/or inducing activated immune cells, e.g. activated T-cells such as activated CD4+ T-cells, can also be used as tags of the invention.

Fusion proteins comprising compounds capable of enhancing the immune response and agonistic binding molecules of the invention can be produced by methods known in the art such as, e.g., recombinantly by constructing nucleic acid molecules comprising nucleotide sequences encoding the agonistic binding molecules in frame with nucleotide sequences encoding the suitable compounds and then expressing the nucleic acid molecules. Alternatively, fusion proteins can be produced chemically by conjugating, directly or indirectly via for instance a linker, agonistic binding molecules as defined herein to a suitable compound.

Alternatively, the binding molecules as described in the present invention can be conjugated to tags and be used for detection and/or analytical and/or diagnostic purposes. The tags used to label the binding molecules for those purposes depend on the specific detection/analysis/diagnosis techniques and/or methods used such as inter alia immunohistochemical staining of tissue samples, flow cytometric detection, scanning laser cytometric detection, fluorescent immunoassays, enzyme-linked immunosorbent assays (ELISA's), radioimmunoassays (RIA's), bioassays (e.g., growth inhibition assays), Western blotting applications, etc. For immunohistochemical staining of tissue samples preferred labels are enzymes that catalyze production and local deposition of a detectable product. Enzymes typically conjugated to binding molecules to permit their immunohistochemical visualization are well-known and include, but are not limited to, alkaline phosphatase, P-galactosidase, glucose oxidase, horseradish peroxidase, and urease. Typical substrates for production and deposition of visually detectable products include, but are not limited to, o-nitrophenyl-beta-D-galactopyranoside (ONPG), o-phenylenediamine dihydrochloride (OPD), p-nitrophenyl phosphate (PNPP), p-nitrophenyl-beta-D-galactopryanoside (PNPG), 3',3'diaminobenzidine (DAB), 3-amino-9-ethylcarbazole (AEC), 4-chloro-1-naphthol (CN), 5-bromo-4-chloro-3-indolyl-phosphate (BCIP), ABTS, BluoGal, iodonitrotetrazolium (INT), nitroblue tetrazolium chloride (NBT), phenazine methosulfate (PMS), phenolphthalein monophosphate (PMP), tetramethyl benzidine (TMB), tetranitroblue tetrazolium (TNBT), X-Gal, X-Gluc, and X-glucoside. Other substrates that can be used to produce products for local deposition are luminescent substrates. For example, in the presence of hydrogen peroxide, horseradish peroxidase can catalyze the oxidation of cyclic diacylhydrazides such as luminol. Next to that, binding molecules of the invention can also be labeled using colloidal gold or they can be labeled with radioisotopes, such as $^{33}$P, $^{32}$P, $^{35}$S, $^{3}$H, and $^{125}$I. When the binding molecules of the present invention are used for flow cytometric detections, scanning laser cytometric detections, or fluorescent immunoassays, they can usefully be labeled with fluorophores. A wide variety of fluorophores useful for fluorescently labeling the binding molecules of the present invention include, but are not limited to, Alexa Fluor and Alexa Fluor dyes, BODIPY dyes, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Cy2, Cy3, Cy3.5, Cy5, Cy5.5, Cy7, fluorescein isothiocyanate (FITC), allophycocyanin (APC), R-phycoerythrin (PE), peridinin chlorophyll protein (PerCP), Texas Red, fluorescence resonance energy tandem fluorophores such as PerCP-Cy5.5, PE-Cy5, PE-Cy5.5, PE-Cy7, PE-Texas Red, and APC-Cy7. When the binding molecules of the present invention are used for secondary detection using labeled avidin, streptavidin, captavidin or neutravidin, the binding molecules may be labeled with biotin.

Next to that, the binding molecules of the invention may be conjugated to photoactive agents or dyes such as fluorescent and other chromogens or dyes to use the so obtained immunoconjugates in photoradiation, phototherapy, or photodynamic therapy. The photoactive agents or dyes include, but are not limited to, photofrin®, synthetic diporphyrins and dichlorins, phthalocyanines with or without metal substituents, chloroaluminum phthalocyanine with or without varying substituents, O-substituted tetraphenyl porphyrins, 3,1-meso tetrakis(o-propionamido phenyl)porphyrin, verdins, purpurins, tin and zinc derivatives of octaethylpurpurin, etiopurpurin, hydroporphyrins, bacteriochlorins of the tetra (hydroxyphenyl)porphyrin series, chlorins, chlorin e6, mono-1-aspartyl derivative of chlorin e$_6$, di-1-aspartyl derivative of chlorin e$_6$, tin(IV) chlorin e$_6$, meta-tetrahydroxyphenylchlor-in, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid benzonaphthoporphyrazines, cationic imminium salts, tetracyclines, lutetium texaphyrin, tin-etio-purpurin, porphycenes, benzophenothiazinium and combinations thereof.

When the immunoconjugates of the invention are used for in vivo diagnostic use, the binding molecules can also be made detectable by conjugation to e.g. magnetic resonance imaging (MRI) contrast agents, including, but not limited to, agents comprising cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); ultrasound contrast agents; X-ray contrast agents, including, but not limited to, agents comprising bismuth (III), gold (III), lanthanum (III) or lead (II); or by radioisotopic labeling, including, but not limited to, agents comprising copper$^{67}$, gallium$^{67}$, gallium$^{61}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$or yttrium$^{90}$.

Furthermore, the binding molecules of the invention can also be attached to solid supports, which are particularly useful for immunoassays or purification of the binding partner, i.e. the human OX40-receptor. Such solid supports might be porous or nonporous, planar or nonplanar and include, but are not limited to, glass, cellulose, polyacrylamide, nylon, polystyrene, polyvinyl chloride or polypropylene supports. The binding molecules can also for example usefully be conjugated to filtration media, such as NHS-activated Sepharose or CNBr-activated Sepharose for purposes of immunoaffinity chromatography. They can also usefully be attached to paramagnetic microspheres, typically by biotin-streptavidin interaction. The microspheres can be used for isolation of cells that express or display the human OX40-receptor or fragments thereof. As another example, the binding molecules of the present invention can usefully be attached to the surface of a microtiter plate for ELISA.

It is another aspect of the present invention to provide a nucleic acid molecule encoding at least a binding molecule or functional fragment thereof according to the invention. Such nucleic acid molecules can be used as intermediates for cloning purposes, e.g. in the process of affinity maturation described above. In a preferred embodiment, the nucleic acid molecules are isolated or purified.

The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parent nucleic acid molecules. Preferably, the nucleic acid molecules encode agonistic binding molecules comprising a CDR3 region, preferably a heavy chain CDR3 region, comprising an amino acid sequence selected from the group consisting of SEQ ID NO:17 (DRYSQVHYALDY), SEQ ID NO:18 (DRYVNTSNAFDY), SEQ ID NO:19 (DMSGFHEFDY), SEQ ID NO:20 (DRYFRQQNAFDY), SEQ ID NO:21 (ARAAGTIFDY), SEQ ID NO:22 (DRYITLPNALDY), SEQ ID NO:23 (YDEPLTIYWFDS) and SEQ ID NO:24 (YDNVMGLYWFDY). Even more preferably, the nucleic acid molecules encode agonistic binding molecules comprising a heavy chain comprising an amino acid sequence selected from the group consisting of SEQ ID NO:25, SEQ ID NO:26, SEQ ID NO:27 and SEQ ID NO:28. In yet another embodiment, the nucleic acid molecules encode binding molecules comprising a heavy chain comprising the amino acid sequence of SEQ ID NO:25 and a light chain comprising the amino acid sequence of SEQ ID NO:29, or they encode a heavy chain comprising the amino acid sequence of SEQ ID NO:26 and a light chain comprising the amino acid sequence of SEQ ID NO:30, or they encode a heavy chain comprising the amino acid sequence of SEQ ID NO:27 and a light chain comprising the amino acid sequence of SEQ ID NO:31, or they encode a heavy chain comprising the amino acid sequence of SEQ ID NO:28 and a light chain comprising the amino acid sequence of SEQ ID NO:32. A further aspect of the invention pertains to nucleic acid molecules comprising a nucleotide sequence selected from the group consisting of SEQ ID NO:39, SEQ ID NO:40, SEQ ID NO:41 and SEQ ID NO:42. Nucleic acid molecules comprising a heavy chain comprising the nucleotide sequence of SEQ ID NO:39 and a light chain comprising the nucleotide sequence of SEQ ID NO:43, a heavy chain comprising the nucleotide sequence of SEQ ID NO:40 and a light chain comprising the nucleotide sequence of SEQ ID NO:44, a heavy chain comprising the nucleotide sequence of SEQ ID NO:41 and a light chain comprising the nucleotide sequence of SEQ ID NO:45 or a heavy chain comprising the nucleotide sequence of SEQ ID NO:42 and a light chain comprising the nucleotide sequence of SEQ ID NO:46 are also a part of the present invention.

Another aspect of nucleic acid molecules according to the present invention, is their potential for use in gene-therapy or vaccination applications. Therefore, in another embodiment of the invention, nucleic acid molecules according to the invention are provided wherein said nucleic acid molecule is present in a gene delivery vehicle. A 'gene delivery vehicle' as used herein refers to an entity that can be used to introduce nucleic acid molecules into cells, and includes liposomes, recombinant viruses, and the like. Preferred gene therapy vehicles of the present invention will generally be viral vectors, such as comprised within a recombinant retrovirus, herpes simplex virus (HSV), adenovirus, adeno-associated virus (AAV), cytomegalovirus (CMV), and the like. Such applications of the nucleic acid sequences according to the invention are included in the present invention. The person skilled in the art will be aware of the possibilities of recombinant viruses for administering sequences of interest to cells. The administration of the nucleic acids of the invention to cells can result in an enhanced immune response.

It is another aspect of the invention to provide vectors, i.e. nucleic acid constructs, comprising one or more nucleic acid molecules according to the present invention. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses such as inter alia alfalfa mosaic virus, bromovirus, capillovirus, carlavirus, carmovirus, caulivirus, closterivirus, comovirus, cryptovirus, cucumovirus, dianthovirus, fabavirus, fijivirus, furovirus, geminivirus, hordeivirus, ilarvirus, luteovirus, machlovirus, marafivirus, necrovirus, nepovirus, phytorepvirus, plant rhabdovirus, potexvirus, potyvirus, sobemovirus, tenuivirus, tobamovirus, tobravirus, tomato spotted wilt virus, tombusvirus, tymovirus, etc; or animal viruses such as inter alia adenovirus, arenaviridae, baculoviridae, birnaviridae, bunyaviridae, caliciviridae, cardioviruses, coronaviridae, corticoviridae, cystoviridae, Epstein-Barr virus, enteroviruses, filoviridae, flaviviridae, Foot-and-Mouth disease virus, hepadnaviridae, hepatitis viruses, herpesviridae, immunodeficiency viruses, influenza virus, inoviridae, iridoviridae, orthomyxoviridae, papovaviruses, paramyxoviridae, parvoviridae, picornaviridae, poliovirus, polydnaviridae, poxviridae, reoviridae, retroviruses, rhabdoviridae, rhinoviruses, Semliki Forest virus, tetraviridae, togaviridae, toroviridae, vaccinia virus, vescular stomatitis virus, etc. Vectors can be used for cloning and/or for expression of the agonistic binding molecules of the invention and might even be used for gene therapy purposes. Vectors comprising one or more nucleic acid molecules according to the invention operably linked to one or more expression-regulating nucleic acid molecules are also covered by the present invention. The choice of vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. Useful markers are dependent on the host cells of choice and are well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the agonistic binding molecules as described above operably linked to one or more nucleic acid molecules encoding proteins or peptides that can be used to isolate the binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the present invention. Preferably, the hosts are host cells. Host cells include, but are not limited to, cells of mammalian, plant, insect, fungal or bacterial origin. Bacterial cells include, but are not limited to, cells from Gram positive bacteria such as several species of the genera *Bacillus, Streptomyces* and *Staphylococcus* or cells of Gram negative bacteria such as several species of the genera *Escherichia* and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells or Bowes melanoma cells are preferred in the present invention. Mammalian cells provide expressed proteins with posttranslational modifications that are most similar to natural molecules of mammalian origin. Since the present invention deals with molecules that may have to be administered to humans, a completely human expression system would be particularly preferred. Therefore, even more preferably, the host cells are human cells, such as HeLa, 911, AT1080, A549, 293 or PER.C6™ cells (PER.C6 is a trademark owned by Crucell Holland B. V.) and cells derived therefrom by genetic modification with antibody encoding expression constructs. In preferred embodiments, the producing human cells comprise at least a functional part of a nucleic acid sequence encoding an adenovirus E1 region in expressible format. In even more preferred embodiments, said host cells are derived from a human retina and immortalized with nucleic acids comprising adenoviral E1 sequences, such as PER.C6™ cells and derivatives thereof. Production of recombinant proteins in host cells can be performed according to methods well known in the art. The use of PER.C6™ cells as a production platform for proteins of interest has been described in WO 00/63403 the disclosure of which is incorporated herein by reference.

It is another aspect of the invention to provide a method of producing agonistic binding molecules or functional variants thereof, preferably human agonistic binding molecules or functional variants thereof according to the present invention. The method comprises the steps of a) culturing a host as described above under conditions conducive to the expression of the agonistic binding molecules, and b) optionally, recovering the expressed agonistic binding molecules. The expressed agonistic binding molecules can be recovered from the cell free extract, but preferably they are recovered from the culture medium. Methods to recover proteins, such as binding molecules, from cell free extracts or culture medium are well known to the man skilled in the art. Agonistic binding molecules or functional variants thereof as obtainable by the above described method are also a part of the present invention.

Alternatively, next to the expression in hosts, such as host cells, the agonistic binding molecules of the invention or functional fragments thereof can be produced synthetically by conventional peptide synthesizers or in cell-free translation systems using RNA's derived from DNA molecules according to the invention. Agonistic binding molecule as obtainable by the above described synthetic production methods or cell-free translation systems are also a part of the present invention.

In yet another alternative embodiment, binding molecules according to the present invention, preferably human agonistic binding molecules specifically binding to the human OX40-receptor or fragments thereof, may be generated by transgenic non-human mammals, such as for instance transgenic mice or rabbits, that express human immunoglobulin genes. Preferably, the transgenic non-human mammals have a genome comprising a human heavy chain transgene and a human light chain transgene encoding all or a portion of the human agonistic binding molecules as described above. The transgenic non-human mammals can be immunized with a purified or enriched preparation of the human OX40-receptor or fragment thereof and/or cells expressing the human OX40-receptor. Protocols for immunizing non-human mammals are well established in the art. See Using Antibodies: A Laboratory Manual, Edited by: E. Harlow, D. Lane (1998), Cold Spring Harbor Laboratory, Cold Spring Harbor, N.Y. and Current Protocols in Immunology, Edited by: J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human agonistic binding molecules are produced by B cells or plasma cells derived from the transgenic animals. In yet another embodiment, the human agonistic binding molecules are produced by hybridomas which are prepared by fusion of B cells obtained from the above described transgenic non-human mammals to immortalized cells. B cells, plasma cells and hybridomas as obtainable from the above described transgenic non-human mammals and human agonistic binding molecules as obtainable from the above described transgenic non-human mammals, B cells, plasma cells and hybridomas are also a part of the present invention. In yet another embodiment, human agonistic binding molecules of the present invention can also be produced in transgenic, non-human, mammals such as inter alia goats or cows, and can be secreted into, and optionally recovered from, the milk of the transgenic mammals.

In a further aspect, the invention provides a method of identifying binding molecules, preferably human binding molecules such as human monoclonal antibodies or fragments thereof, according to the invention or nucleic acid molecules according to the invention and comprises the steps of a) contacting a phage library of binding molecules, preferably human binding molecules, with material comprising the human OX40-receptor or a part thereof, b) selecting at least once for a phage binding to the material comprising the human OX40-receptor or a part thereof, and c) separating and recovering the phage binding to the material comprising the human OX40-receptor or a part thereof. The selection step according to the present invention is preferably performed in the presence of at least part of the human OX40-receptor, e.g. cells transfected with the human OX40-receptor expression plasmids, isolated human OX40-receptor, the extracellular part thereof, fusion proteins comprising such, and the like.

Phage display methods for identifying and obtaining binding molecules, e.g. antibodies, are by now well-established methods known by the person skilled in the art. They are e.g. described in U.S. Pat. No. 5,696,108; Burton and Barbas, 1994; and de Kruif et al., 1995b. For the construction of phage display libraries, collections of human monoclonal antibody heavy and light chain variable region genes are expressed on the surface of bacteriophage, preferably filamentous bacteriophage, particles, in for example single chain Fv (scFv) or in Fab format (see de Kruif et al., 1995b). Large libraries of antibody fragment-expressing phages typically contain more than $1.0 \times 10^9$ antibody specificities and may be assembled from the immunoglobulin V regions expressed in the B lymphocytes of immunized- or non-immunized individuals. Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g. CDR regions. Antigen specific phage antibodies can be selected from the library by immobilizing target antigens such as the human OX40-receptor or fragments thereof on a solid phase and subsequently exposing the target antigens to a phage library to allow binding of phages expressing antibody fragments specific for the solid phase-bound antigen. Non-bound phages are removed by washing and bound phages eluted from the solid phase for infection of *Escherichia coli* (*E. coli*) bacteria and subsequent propagation. Multiple rounds of selection and propagation are usually required to sufficiently enrich for phages binding specifically to the target antigen. Phages may also be selected for binding to complex antigens such as complex mixtures of proteins or whole cells such as cells transfected with the human OX40-receptor expression plasmids or cells naturally expressing the human OX40-receptor. Selection of antibodies on whole cells has the advantage that target antigens are presented in their native configuration, i.e. unperturbed by possible conformational changes that might have been introduced in the case where an antigen is immobilized to a solid phase. Antigen specific phage antibodies can be selected from the library by incubating a cell population of interest, expressing known and unknown antigens on their surface, with the phage antibody library to let for example the scFv or Fab part of the phage bind to the antigens on the cell surface. After incubation and several washes to remove unbound and loosely attached phages, the cells of interest are stained with specific fluorescent labeled antibodies and separated on a Fluorescent Activated Cell Sorter (FACS). Phages that have bound with their scFv or Fab part to these cells are eluted and used to infect *Escherichia coil* to allow amplification of the new specificity. Generally, one or more selection rounds are required to separate the phages of interest from the large excess of non-binding phages. Monoclonal phage preparations can be analyzed for their specific staining patterns and allowing identification of the antigen being recognized (De Kruif et al., 1995a; Lekkerkerker and Logtenberg, 1999). The phage display method can be extended and improved by subtracting non-relevant binders during screening by addition of an excess of non-target molecules that are similar but not identical to the target, and thereby strongly enhance the chance of finding relevant binding molecules (see U.S. Pat. No. 6,265,150 which is incorporated herewith by reference). In this method, subtraction can be done by the presence of T-cells and other lymphocytes that do not express the human OX40-receptor.

In yet a further aspect, the invention provides a method of obtaining a binding molecule, preferably a human binding molecule or a nucleic acid molecule according to the invention, wherein the method comprises the steps of a) performing the above described method of identifying binding molecules, preferably human binding molecules such as human monoclonal antibodies or fragments thereof according to the invention, or nucleic acid molecules according to the invention, and b) isolating from the recovered phage the human binding molecule and/or the nucleic acid encoding the human binding molecule. Once a new monoclonal phage antibody has been established or identified with the above mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFv's or complete human immunoglobulins of a desired specificity (e.g. IgG, IgA or IgM). These constructs can be transfected into suitable cell lines and complete binding molecules such as human monoclonal antibodies can be produced (see Huls et al., 1999; Boel et al., 2000).

Preferably, after identifying and obtaining a binding molecule specifically binding to the human OX40-receptor, it is established if the binding molecule has agonistic activity. This can be tested in vitro in a cell culture system or in an animal model system. The cell culture system can comprise cells derived from a tissue sample of a patient. For instance, activated CD4+ T-cells can be contacted with a binding molecule of the invention or a control binding molecule and the ability of the binding molecule of the invention to enhance the activity of activated CD4+ T-cells compared to the control binding molecule can be determined. Furthermore, the activation induced by the binding molecule of the invention might be compared to a well-known inducer of the OX40-receptor such as the OX40-ligand. Moreover, with this kind of test a binding molecule with antagonistic activity can be identified and optionally used in the treatment of a disorder or disease wherein antagonistic binding molecules capable of binding to the human OX40-receptor are useful. The ability of binding molecule according to the invention to modulate (either enhance or decrease) the activity of activated CD4+ T-cells can be assessed by detecting the proliferation of CD4+ T-cells, detecting the activation of signaling molecules, detecting the effector function of CD4+ T-cells, detecting the expression of cytokines or antigens, or detecting the differentiation of CD4+ T-cells. Furthermore, agonistic activity of the binding molecules can be established by a costimulation assay with for instance the OX40-ligand as described in the present examples. Techniques known to those of skill in the art can be used for measuring these activities. For example, cellular proliferation can be assayed by $^3$H-thymidine incorporation assays and trypan blue cell counts. The activation of signaling molecules can be assayed, for example, by kinase assays and electromobility shift assays (EMSAs). The effector function of T-cells can be measured, for example, by cytokine ELISA assays or elispot assays. Cytokine and antigen expression can be assayed, for example, by immunoassays including, but not limited to, competitive and non-competitive assay systems using techniques such as Western blots, immunohistochemistry, radioimmunoassays, ELISA, sandwich immunoassays, immunoprecipitation assays, immunodiffusion assays, agglutination assays, complement-fixation assays, immunoradiometric assays, fluorescent immunoassays, protein A immunoassays and FACS analysis. The binding molecules of the invention can also be tested in suitable animal model systems prior to use in humans. Such animal model systems include, but are not limited to, mice, rats, chicken, cows, monkeys, pigs, dogs, rabbits, etc. Any animal system well-known in the art may be used.

In a further aspect, the invention provides compositions comprising at least one agonistic binding molecule, at least one functional variant or fragment thereof, at least one immunoconjugate according to the invention or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. Examples of such salts include, but are not limited to, acid addition salts and base addition salts. Acid addition salts include, but are not limited to, those derived from nontoxic inorganic acids, such as hydrochloric, nitric, phosphoric, sulfuric, hydrobromic, hydro-iodic, and phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include, but are not limited to, those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. If necessary, the binding molecules of the invention may be coated in or on a material to protect them from the action of acids or other natural or non-natural conditions that may inactivate the binding molecules.

In yet a further aspect, the invention provides compositions comprising at least one nucleic acid molecule as defined in the present invention. The compositions may comprise aqueous solutions such as aqueous solutions containing salts (e.g., NaCl or salts as described above), detergents (e.g., SDS) and/or other suitable components.

Furthermore, the present invention pertains to pharmaceutical compositions comprising at least one agonistic binding molecule according to the invention, at least one functional variant or fragment thereof, at least one immunoconjugate according to the invention, at least one composition according to the invention, or combinations thereof. The pharmaceutical composition of the invention further comprises at least one pharmaceutically acceptable excipient. A pharmaceutical composition according to the invention can further comprise at least one other therapeutic, prophylactic and/or diagnostic agent. Alternatively, the further therapeutic, prophylactic and/or diagnostic agents can also be administered separately from the pharmaceutical composition of the invention. The pharmaceutical compositions of the invention can be used in vitro, ex vivo or in vivo. Therapeutic agents and prophylactic agents can include, but are not limited to, toxic substances, radioactive substances, liposomes, binding molecules (with or without tags) specifically binding to cancer cell antigens, enzymes, polynucleotide sequences, plasmids, proteins, peptides or combinations thereof. Toxic substances include, but are not limited to, cytotoxic agents, such as small molecule toxins or chemotherapeutic agents, or enzymatically active toxins of bacterial, fungal, plant or animal origin, or fragments thereof. In general, suitable chemotherapeutic agents are described in Remington's Pharmaceutical Sciences, 18$^{th}$ edition (1990), Edited by: A. R. Gennaro, Mack Publishing Co., Philadelphia and in Goodman and Gilman's The Pharmacological Basis of Therapeutics, 7th edition (1985), Edited by: A. G. Gilman, L. S. Goodman, T. W. Rall and F. Murad. MacMillan Publishing Co., New York. Suitable chemotherapeutic agents that are still in the experimental phase are known to those of skill in the art and might also be used as toxic substances in the present invention. In a specific embodiment, therapeutic agents and prophylactic agents can include, but are not limited to, compounds that stimulate and/or activate and/or enhance and/or augment and/or induce activated immune cells, e.g. activated T-cells such as activated CD4+ T-cells. Such compounds may include, but are not limited to, binding molecules, small molecules, organic or inorganic compounds, enzymes, polynucleotide sequences, plasmids, proteins, peptides, liposomes or combinations thereof. Examples of compounds capable of enhancing the immune response include, but are not limited to, compounds that activate a cytokine receptor such as inter alia cytokines including, but not limited to, CSF-1, Flt3 ligand, G-CSF, GM-CSF, IFN-α, IFN-β, IFN-γ, IL-1β, IL-2, IL-3, IL-4, IL-5, IL-6, IL-7, IL-8, IL-9, IL-10, IL-12, IL-15, IL-18, M-CSF, and TNF-α; chemokines including, but not limited to, IP-10, MIG, and MIP-1; binding molecules that immunospecifically bind to the CSF-1 receptor, Flt3, G-CSF receptor, GM-CSF receptor, IFN-α receptor, IFN-β receptor, IFN-γ receptor, IL-1β receptor, IL-2 receptor, IL-3 receptor, IL-4 receptor, IL-5 receptor, IL-6 receptor, IL-7 receptor, IL-8 receptor, IL-9 receptor, IL-10 receptor, IL-12 receptor, IL-15 receptor, IL-18 receptor, IP-10 receptor, M-CSF receptor, MIG receptor, MIP-1 receptor, and TNF-α receptor. Pharmaceutically acceptable salts, acids or derivatives, analogs, derivatives or fragments of the above listed compounds which are still functional, i.e. are capable of stimulating and/or activating and/or enhancing and/or augmenting and/or inducing activated immune cells, e.g. activated T-cells such as activated CD4+ T-cells, can also be used as further therapeutic or prophylactic agents. In a specific embodiment of the invention the pharmaceutical composition of the invention comprises an OX40-ligand, preferably a human OX40-ligand. This ligand can also be administered separately, either before, subsequent to, or after administration of the pharmaceutical composition of the invention.

Alternatively, the further therapeutic or prophylactic agents include, but are not limited to, anti-viral, anti-microbial, such as anti-bacterial, or anti-fungal agents. Such agents can be binding molecules, small molecules, organic or inorganic compounds, enzymes, polynucleotide sequences etc. Examples of anti-microbial agents include, but are not limited to, amifloxacin, amikacin, amoxicillin, amphotericin B, ampicillin, azlocillin, aztreonam, bacampicillin, bacitracin, bifonazole, cafamandole, candicidin, carbenicillin, carbenicillin indanyl, cefaclor, cefadroxil, cefazolin, cefepime, cefonicid, cefoparazone, ceforanide, cefotaxime, cefotetan, cefoxitin, cefpodoxime proxetil, ceftazidime, ceftizoxime, ceftriaxone, cefuroxime, cefuroxime axetil, cepalospolin, cephadrine, cephalexin, cephalothin, chlortetracycline, cinoxacin, ciprofloxacin, clavulanic acid, cloxacillin, clotrimazole, demeclocycline, dicloxacillin, doxycycline, econazole, erythromycin, fleroxacin, floxacillin, 5-fluorocytosine, fluconazole, gentamicin, griseofulvin, haloprogin, imipenem, itraconazole, kanamycin, ketoconazole, lomefloxacin, loracarbef, methacycline, methicillin, metronidazole, mezlocillin, miconazole, minocycline, moxalactam, nafcillin, natamycin, neomycin, netilmicin, norfloxacin, nystatin, ofloxacin, oxacillin, oxytetracycline, para-aminobenzoic acid, pefloxacin, penicillin G, penicillin V, pentamidine, piperacillin, sparfloxacin, streptomycin, sulfacetamide, sulfadiazine, sulfamethoxazole, sulfanilamide, sulfisoxazole, tetracycline, ticarcillin, tobramycin, trimethoprim-sulfamethoxazole nalidixic acid, vancomycin, vibunazole, and pharmaceutically acceptable salts, acids or derivatives of any of the above.

Examples of anti-viral agents include, but are not limited to, abacavir, acyclovir, adefovir, afovirsen, amantadine, amprenavir, AZT, camptothecins, castanospermine, cidofovir, D4T, ddC, ddI, d4T, delavirdine, didanosine, efavirenz, famciclovir, fialuridine, foscarnet, FTC, ganciclovir, GG167, idoxuridine, indinavir, interferon alpha, lamivudine, lobucavir, loviride, nelfinavir, nevirapine, oseltamivir, penciclovir, pirodavir, ribavirin, rimantadine, ritonavir, saquinavir, sICAM-1, sorivudine, stavudine, trifluridine, 3TC, valacyclovir, vidarabine, zalcitabine, zanamivir, zidovudine, and pharmaceutically acceptable salts, acids or derivatives of any of the above.

Examples of anti-fungal agents include, but are not limited to, amphotericin B, benzoic acid, butoconazole, caprylic acid, ciclopirox olamine, clotrimazole, econazole, fluconazole, flucytosine, griseofulvin, haloprogin, imidazoles, itraconzole, ketoconazole, miconazole, naftifine, nystatin, potassium iodide, propionic acid, salicyclic acid, terbinafine, terconazole, tolnaftate, and triazoles, undecylenic acid, and pharmaceutically acceptable salts, acids or derivatives of any of the above.

Typically, pharmaceutical compositions must be sterile and stable under the conditions of manufacture and storage. The agonistic binding molecules, variant or fragments thereof, immunoconjugates, nucleic acid molecules or compositions of the present invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the agonistic binding molecules, variant or fragments thereof, immunoconjugates, nucleic acid molecules or compositions of the present invention can be in solution and the appropriate pharmaceutically acceptable excipient can be added and/or mixed before or at the time of delivery to provide a unit dosage injectable form. Preferably, the pharmaceutically acceptable excipient used in the present invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the agonistic binding molecules of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the agonistic binding molecules with, or co-administer the agonistic binding molecules with, a material or compound that prevents the inactivation of the agonistic binding molecules. For example, the agonistic binding molecules may be administered to a subject in an appropriate carrier, for example, liposomes, or a diluent.

The routes of administration can be divided into two main categories, oral and parenteral administration. These two categories include, but are not limited to, bolus, buccal, epidermal, epidural, inhalation, intra-abdominal, intra-arterial, intra-articular, intrabronchial, intracapsular, intracardiac, intracartilaginous, intracavitary, intracelial, intracelebellar, intracerebronventricular, intracolic, intracervical, intradermal, intragastric, intrahepatic, intramedullary, intramuscular, intramyocardial, intranasal, intra-ocular intra-orbital, intraosteal, intrapelvic, intrapericardiac, intraperitoneal, intraplaque, intrapleural, intraprostatic, intrapulmonary, intrarectal, intrarenal, intraretinal, intraspinal, intrasternal, intrasynovial, intrathecal, intrathoracic, intratumoral, intrauterine, intravenous, intraventricular, intravesical, rectal, spinal, subarachnoid, subcapsular, subcutaneous, subcuticular, sublingual, topical, transdermal, and transmucosal, transtracheal, vaginal administration.

Oral dosage forms can be formulated inter alia as tablets, troches, lozenges, aqueous or oily suspensions, dispersable powders or granules, emulsions, hard capsules, soft gelatin capsules, syrups or elixirs, pills, dragees, liquids, gels, or slurries. These formulations can contain pharmaceutically acceptable excipients including, but not limited to, inert diluents such as calcium carbonate, sodium carbonate, lactose, calcium phosphate or sodium phosphate; granulating and disintegrating agents such as corn starch or alginic acid; binding agents such as starch, gelatin or acacia; lubricating agents such as calcium stearate, glyceryl behenate, hydrogenated vegetable oils, magnesium stearate, mineral oil, polyethylene glycol, sodium stearyl, fumarate, stearic acid, talc, zinc stearate; preservatives such as n-propyl-p-hydroxybenzoate; colouring, flavouring or sweetening agents such as sucrose, saccharine, glycerol, propylene glycol or sorbitol; vegetable oils such as arachis oil, olive oil, sesame oil or coconut oil; mineral oils such as liquid paraffin; wetting agents such as benzalkonium chloride, docusate sodium, lecithin, poloxamer, sodium lauryl sulfate, sorbitan esters; and thickening agents such as agar, alginic acid, beeswax, carboxymethyl cellulose calcium, carageenan, dextrin or gelatin.

The pharmaceutical compositions of the present invention can also be formulated for parenteral administration. Formulations for parenteral administration can be inter alia in the form of aqueous or non-aqueous isotonic sterile non-toxic injection or infusion solutions or suspensions. Preferred parenteral administration routes include intravenous, intraperitoneal, epidural, intramuscular and intratumoral injection or infusion. The solutions or suspensions may comprise agents that are non-toxic to recipients at the dosages and concentrations employed such as 1,3-butanediol, Ringer's solution, Hank's solution, isotonic sodium chloride solution, oils such as synthetic mono- or diglycerides or fatty acids such as oleic acid, local anaesthetic agents, preservatives, buffers, viscosity or solubility increasing agents, water-soluble antioxidants such as ascorbic acid, cysteine hydrochloride, sodium bisulfate, sodium metabisulfite, sodium sulfite and the like, oil-soluble antioxidants such as ascorbyl palmitate, butylated hydroxyanisole (BHA), butylated hydroxytoluene (BHT), lecithin, propyl gallate, alpha-tocopherol, and the like, and metal chelating agents, such as citric acid, ethylenediamine tetraacetic acid (EDTA), sorbitol, tartaric acid, phosphoric acid, and the like.

In a further aspect, the invention encompasses the use of an agonistic binding molecule, a functional variant, an immunoconjugate, a nucleic acid molecule, a composition or a pharmaceutical composition of the invention for stimulating T-cells, preferably activated CD4+ T-cells in vitro. The agonistic binding molecules of the invention can also be contacted together with antigen-presenting cells with T-cells to stimulate T-cell proliferation in vitro.

The agonistic binding molecules, preferably the human agonistic binding molecules such as human agonistic monoclonal antibodies according to the invention, the variants or fragments thereof, the immunoconjugates according to the invention, the nucleic acid molecules according to the invention, the compositions according to the invention or the pharmaceutical compositions according to the invention can be used as medicaments. They can inter alia be used in the diagnosis, prophylaxis, treatment, or combination thereof, of a neoplastic, viral, or bacterial disorder or disease. Preferably, the neoplastic disorder or disease is selected from the group consisting of heavy chain disease, leukemias (e.g., acute myeloid leukemia, chronic myeloid leukemia, chronic myelomonocytic leukemia, acute promyelocytic leukemia, myelodysplastic syndrome, juvenile myelomonocytic leukemia, etc.), metastases, neoplasms, tumors (e.g., acoustic neuroma, adenocarcinoma, adrenal cortical cancer, anal carcinoma, angiosarcoma, astrocytoma, basal cell carcinoma, bile duct carcinoma, bladder carcinoma, brain cancer, breast cancer, bronchogenic carcinoma, cancer of the peritoneum, cervical cancer, chondrosarcoma, chordoma, choriocarcinoma, colon carcinoma, colorectal cancer, craniopharyngioma, cystadenocarcinoma, embryonal carcinoma, endometrial carcinoma, endotheliosarcoma, ependymoma, epithelial carcinoma, esophageal cancer, Ewing's tumor, fibrosarcoma, gastrointestinal cancer, genitourinary tract cancer, glioblastoma, glioma, head cancer, hemangioblastoma, hepatoma, Hodgkin's Disease, kidney cancer, leiomyosarcoma, liposarcoma, liver cancer, lung carcinoma, lymphangioendotheliosarcoma, lymphangiosarcoma, lymphomas, malignant hypercalcemia, malignant pancreatic insulanoma, medullary carcinoma, medulloblastoma, melanoma, meningioma, mesothelioma, neck cancer, neuroblastoma, non-Hodgkin's lymphoma, non-small cell lung carcinoma, oligodendroglioma, osteogenic sarcoma, ovarian cancer, pancreatic cancer, papillary adenocarcinomas, papillary carcinoma, penile carcinoma, pinealoma, premalignant skin lesions, primary brain tumors, primary macroglobulinemia, primary thrombocytosis, prostate cancer, rectal cancer, renal cell carcinoma, retinoblastoma, rhabdomyosarcoma, salivary gland carcinoma, sarcoma, sebaceous gland carcinoma, seminoma, small cell lung carcinoma, squamous cell carcinoma, stomach cancer, synovioma, sweat gland carcinoma, testicular tumor, thyroid cancer, uterine carcinoma, vulval cancer, and Wilms tumor), or any disease or disorder characterized by uncontrolled cell growth. The binding molecules of the invention are suitable for treatment of yet untreated patients suffering from any of the above disorders and diseases, patients who have been or are treated and are in remission or are not in remission, and patients with a recurrent/refractory diseases or disorders.

Preferably, the viral disorder or disease is selected from the group consisting of disorders or diseases associated with the coronavirus responsible for the Severe Acute Respiratory Syndrome (SARS), herpes simplex virus (HSV), hepatitis B virus (HBV), hepatitis C virus (HCV), human T-cell lymphotrophic virus (HTLV) type I and II, human immunodeficiency virus (HIV) type I and II, cytomegalovirus, papillomavirus, polyoma viruses, adenoviruses, Epstein-Barr virus, poxviruses, influenza virus, measles virus, rabies virus, Sendai virus, poliomyelitis virus, coxsackieviruses, rhinoviruses, reoviruses, and rubella virus.

Preferably, the bacterial (for sake of simplicity also including yeast and fungal disorders and diseases) disorder or disease is selected from the group consisting of disorders or diseases associated with *Acinetobacter* sp., *Aeromonas hydrophila*, *Alcaligenes faecalis*, *Bacillus cereus*, *Bacteroides fragilis*, *Bacteroides ovatus*, *Bacteroides ureolyticus*, *Bacteroides vulgatus*, *Borrelia burgdorferi*, *Borrelia vincentii*, *Brucella abortus*, *Brucella melitensis*, *Brucella suis*, *Campylobacter* (*Vibrio*) *fetus*, *Campylobacter jejuni*, *Chlamydia* spp., *Citrobacter diversus*, *Citrobacter freundii*, *Corynebacterium jeikeium*, *Clostridium botulinum*, *Clostridium difficile*, *Clostridium perfringens*, *Clostridium ramosum*, *Clostridium sporogenes*, *Clostridium* sp., *Clostridium tetani*, *Corynebacterium diphtheriae*, *Edwardsiella tarda*, *Enterobacter aerogenes*, *Enterobacter cloacae*, *Enterococcus faecalis*, *Escherichia coli*, *Francisella tularensis*, *Haemophilus influenzae*, *Helicobacter pylori*, *Klebsiella oxytoca*, *Klebsiella ozaenae*, *Klebsiella pneumoniae*, *Klebsiella rhinoscleromotis*, *Leptospira icterohemorrhagiae*, *Mycobacterium tuberculosis*, *Mycoplasma* spp., *Neisseria gonorrhoea*, *Neisseria meningitidis*, *Peptostreptococcus anaerobius*, *Peptostreptococcus asaccharolyticus*, *Peptostreptococcus magnus*, *Pneumocystis carinii*, *Prevotella bivia*, and *Prevotella melaninogenica*, *Pseudomonas aeruginosa*, *Pseudomonas fluorescens*, *Pseudomonas stutzeri*, *Rickettsia prowazeki*, *Rickettsia tsutsugumushi*, *Salmonella typhimurium*, *Shigella dysenteriae*, *Shigella flexneri*, *Shigella sonnei*, *Staphylococcus aureus*, *Staphylococcus epidermidis*, *Streptococcus* group C, *Streptococcus* group G, *Staphylococcus haemolyticus*, *Staphylococcus hominis*, *Staphylococcus simulans*, *Staphylococcus warneri*, *Staphylococcus xylosus*, *Stenotrophomonas maltophilia*, *Streptococcus agalactiae*, *Streptococcus bovis*, *Streptococcus equinus*, *Streptococcus pneumoniae*, *Streptococcus pyogenes*, *Streptococcus pyogenes*, *Toxoplasma gondii*, *Treponema carateneum*, *Treponema pallidum*, *Treponema pertenue*, *Vibrio cholerae*, *Yersinia enterocolitica*, *Yersinia pestis*, and *Yersinia pseudotuberculosis*.

Preferably, the agonistic binding molecules, preferably the human agonistic binding molecules such as human agonistic monoclonal antibodies according to the invention, the variants or fragments thereof, the immunoconjugates according to the invention, the nucleic acid molecules according to the invention, the compositions according to the invention or the pharmaceutical compositions according to the invention can be used for enhancing the immune response in a human or animal, more preferably for enhancing the immune response against a tumour, bacterial or viral antigen in a human or animal. In a specific embodiment the agonistic binding molecules of the invention can be used in combination with the OX40-ligand, preferably the human OX40-ligand. These compounds may exert a costimulatory effect.

As a further aspect, the invention encompasses a method for modulating a T-cell response in a human, comprising the step of administering to said human an effective dose of a binding molecule according to the invention or a functional variant according to the invention, an immunoconjugate according to the invention, a nucleic acid molecule according to the invention, a vector according to the invention or a pharmaceutical composition according to the invention. Preferably, said modulation comprises the stimulation of T-cell proliferation.

Another aspect of the invention covers the use of an agonistic binding molecule, a functional variant, an immunoconjugate, a nucleic acid molecule, a composition or a pharmaceutical composition for the preparation of a medicament for the treatment of a neoplastic, viral or bacterial disorder or a disease as described herein. More preferably, the use will be for the preparation of a medicament for enhancing the immune response in a human or animal, more preferably the use will be for the preparation of a medicament for enhancing the immune response against a tumour, bacterial or viral antigen in a human or animal.

The molecules are typically formulated in the compositions and pharmaceutical compositions of the invention in a therapeutically, prophylactically or diagnostically effective amount such as for instance 1-100 mg/kg, preferably 1-25 mg/kg, more preferably 3-10 mg/kg. Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. The molecules and compositions according to the present invention are preferably sterile. Methods to render these molecules and compositions sterile are well known in the art.

Alternatively, cells that are genetically engineered to express the human agonistic binding molecules of the invention are administered to patients in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the nucleic acid molecules of the invention into the cells.

Preferably, the agonistic binding molecules are secreted from the cells. The engineered cells which express and preferably secrete the binding molecules as described herein can be introduced into the patient for example systemically, e.g., in the circulation, or intraperitoneally. In other embodiments, the cells can be incorporated into a matrix or can be encapsulated and implanted in the body.

In another embodiment, activated CD4+ T-cells are removed from a patient and contacted with the agonistic binding molecules of the invention in vitro. Thereafter, the treated activated CD4+ T-cells are administered to the patient.

In yet a further specific embodiment, the agonistic binding molecules of the invention and antigen-presenting cells are contacted with T-cells to stimulate T-cell proliferation in vitro.

In a specific embodiment, neoplastic, viral or bacterial antigens or combinations thereof can be administered before, concomitant or after administration of the agonistic binding molecules of the invention. Preferably, the antigens are administered to a subject with an neoplastic or infectious disorder or disease prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before) the administration of the agonistic binding molecules of the invention. The antigens include, but are not limited to, recombinantly produced antigens, purified antigens, compositions comprising the antigens, neoplastic cells comprising the antigens, portions of neoplastic cells, such as for instance membranes, comprising the antigens, fragments of the antigens, viruses, bacteria, fungi, yeast and other microorganisms. If cells are used, the cells can be used directly after removal from the patient, but preferably the cells are first attenuated before administration to a patient. If viruses or bacteria or other infectious organisms are used, the organisms are preferably first attenuated before administration to a patient. Methods for attenuation are known in the art and include, but are not limited to, irradiation, heat treatment and chemical inactivation.

In connection with the treatment of neoplastic disorders or diseases, the agonistic binding molecules of the present invention may be used in combination with classical approaches, such as surgery, radiotherapy, chemotherapy, and the like. The human agonistic binding molecules and chemotherapeutic, radiotherapeutic or anti-angiogenic agents may be administered in a single composition or as two distinct compositions using identical or different administration routes. The invention therefore also provides combined therapies in which the agonistic binding molecules of the invention are used simultaneously with, before, or after surgery, radiotherapy or chemotherapy or are administered to patients with, before, or after conventional chemotherapeutic, radiotherapeutic or anti-angiogenic agents. When the administration of the human agonistic binding molecule precedes or follows the administration of the chemotherapeutic, radiotherapeutic or anti-angiogenic agents, intervals ranging from minutes to weeks may lie between the various administrations. It has to be ensured however that a significant period of time does not expire between the time of each delivery, such that the composition comprising the agent and the composition comprising the agonistic binding molecule will still be able to exert an advantageously combined effect on the neoplasm or tumor. In such instances, it is contemplated that one will contact the neoplasm or tumor with both compositions within about 2 minutes to about one week of each other and, more preferably, within about 12-72 hours of each other, with a delay time of only about 12-48 hours being most preferred.

In connection with the treatment of viral or bacterial disorders or diseases as mentioned above, the agonistic binding molecules of the present invention may be used in combination with anti-viral and/or anti-bacterial compounds as described above. An similar dosage regimen as indicated for the treatment of neoplastic disorders and diseases can also be applied for the viral or bacterial disorders or diseases, i.e. one or more human agonistic binding molecules or compositions comprising them may be administered to a subject with an infectious disease prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more anti-viral and/or anti-bacterial compounds.

Next to that, pharmaceutical packs or kits comprising at least one agonistic binding molecule, preferably human agonistic binding molecules such as human agonistic monoclonal antibodies according to the invention, at least one variant or fragment thereof, at least one immunoconjugate according to the invention, at least one nucleic acid molecule according to the invention, at least one composition according to the invention, at least one pharmaceutical composition according to the invention, at least one vector according to the invention, at least one host according to the invention or a combination thereof are also a part of the present invention. Optionally, the kits also contain other therapeutic or prophylactic compounds. Optionally, the above described components of the kits of the invention are packed in suitable containers and labeled for diagnosis, prophylaxis and/or treatment of the indicated conditions. The above-mentioned components may be stored in unit or multi-dose containers, for example, sealed ampules, vials, bottles, syringes, and test tubes, as an aqueous, preferably sterile, solution or as a lyophilized, preferably sterile, formulation for reconstitution. The containers may be formed from a variety of materials such as glass or plastic and may have a sterile access port (for example the container may be an intravenous solution bag or a vial having a stopper pierceable by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. Associated with the kits can be instructions customarily included in commercial packages of therapeutic, prophylactic or diagnostic products, that contain information about for example the indications, usage, dosage, manufacture, administration, contraindications and/or warnings concerning the use of such therapeutic or diagnostic products. The documents providing instructions for the use of the agents of the kit can be in, e.g., written and/or electronic form.

EXAMPLES

To illustrate the invention, the following examples are provided. The examples are not intended to limit the scope of the invention in any way.

Example 1

Selection of Phage Carrying Single Chain Fv Fragments Specifically Recognizing Human OX40-receptor Using OX40-Ig Fusion Protein.

Antibody fragments were selected using antibody phage display libraries and MAbstract™ technology, essentially as described in U.S. Pat. No. 6,265,150 and in WO 98/15833, both of which are incorporated herein in their entirety. All procedures were performed at room temperature unless stated otherwise. A human OX40-Ig fusion protein consisting of the extracellular domain of the human OX40-receptor linked to the CH2 and CH3 domains of human IgG1 was obtained commercially (Alexis Biochemicals) and coated for 2 hours at 37° C. onto the surface of Maxisorp™ plastic tubes (Nunc) at a concentration of 1.25 µg/ml. The tubes were blocked for 1 hour in 2% fat free milk powder dissolved in PBS (MPBS). Simultaneously, 500 µl (approximately $10^{13}$ cfu) of a phage display library expressing single chain Fv fragments (scFv's) essentially prepared as described by De Kruif et al. (1995a) and references therein (which are incorporated herein in their entirety), was added to two volumes of 4% MPBS. In addition, human serum was added to a final concentration of 15% and blocking was allowed to proceed for 30-60 minutes. The OX40-Ig-coated tubes were emptied and the blocked phage library was added. The tube was sealed and rotated slowly for 1 hour, followed by 2 hours of incubation without rotation. The tubes were emptied and washed 10 times in PBS containing 0.1% Tween-20, followed by washing 5 times in PBS. 1 ml glycine-HCL, 0.05 M, pH 2.2 was added, and the tube was rotated slowly for 10 minutes. The eluted phages were added to 500 µl 1M Tris-HCl pH 7.4. To this mixture, 3.5 ml of exponentially growing XL-1 blue bacterial culture was added. The tubes were incubated for 30 minutes at 37° C. without shaking. Then, the bacteria were plated on 2TY agar plates containing ampicillin, tetracycline and glucose. After overnight incubation of the plates at 37° C., the colonies were scraped from the plates and used to prepare an enriched phage library, essentially as described by De Kruif et al. (1995a). Briefly, scraped bacteria were used to inoculate 2TY medium containing ampicillin, tetracycline and glucose and grown at a temperature of 37° C. to an $OD_{600nm}$ of ~0.3. Helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages were precipitated using polyethylene glycol 6000/NaCl. Finally, the phages were dissolved in a small volume of PBS containing 1% BSA, filter-sterilized and used for a next round of selection. The selection/re-infection procedure was performed twice. After the second round of selection, individual E. coli colonies were used to prepare monoclonal phage antibodies. Essentially, individual colonies were grown to log-phase and infected with helper phages after which phage antibody production was allowed to proceed overnight. Phage antibody containing supernatants were tested in ELISA for binding activity to human OX40-Ig coated 96 wells plates.

Example 2

Validation of the Human OX40R-specific scFv's.

Selected phage antibodies that were obtained in the screen described above, were validated in ELISA for specificity. For this purpose, human OX40-Ig was coated to Maxisorp™ ELISA plates. After coating, the plates were blocked in 2% MPBS. The selected phage antibodies were incubated in an equal volume of 4% MPBS. The plates are emptied, washed once in PBS, after which the blocked phages were added. Incubation was allowed to proceed for 1 hour, the plates were washed in PBS containing 0.1% Tween-20 and bound phages were detected using an anti-M13 antibody conjugated to peroxidase. As a control, the procedure was performed simultaneously using a control phage antibody directed against thyroglobulin (De Kruif et al. 1995a and 1995b), which served as a negative control. As shown in FIG. 1, the selected phage antibodies called SC02008, SC02009, SC02010, SC02011, SC02012 and SC02021 displayed significant binding to the immobilized human OX40-Ig fusion protein.

The phage antibodies that bound to human OX40-Ig were subsequently tested for binding to human serum IgG to exclude the possibility that they recognized the Fc part of the fusion protein. None of the selected anti-OX40-receptor phages demonstrated binding to human IgG.

Figure 2:
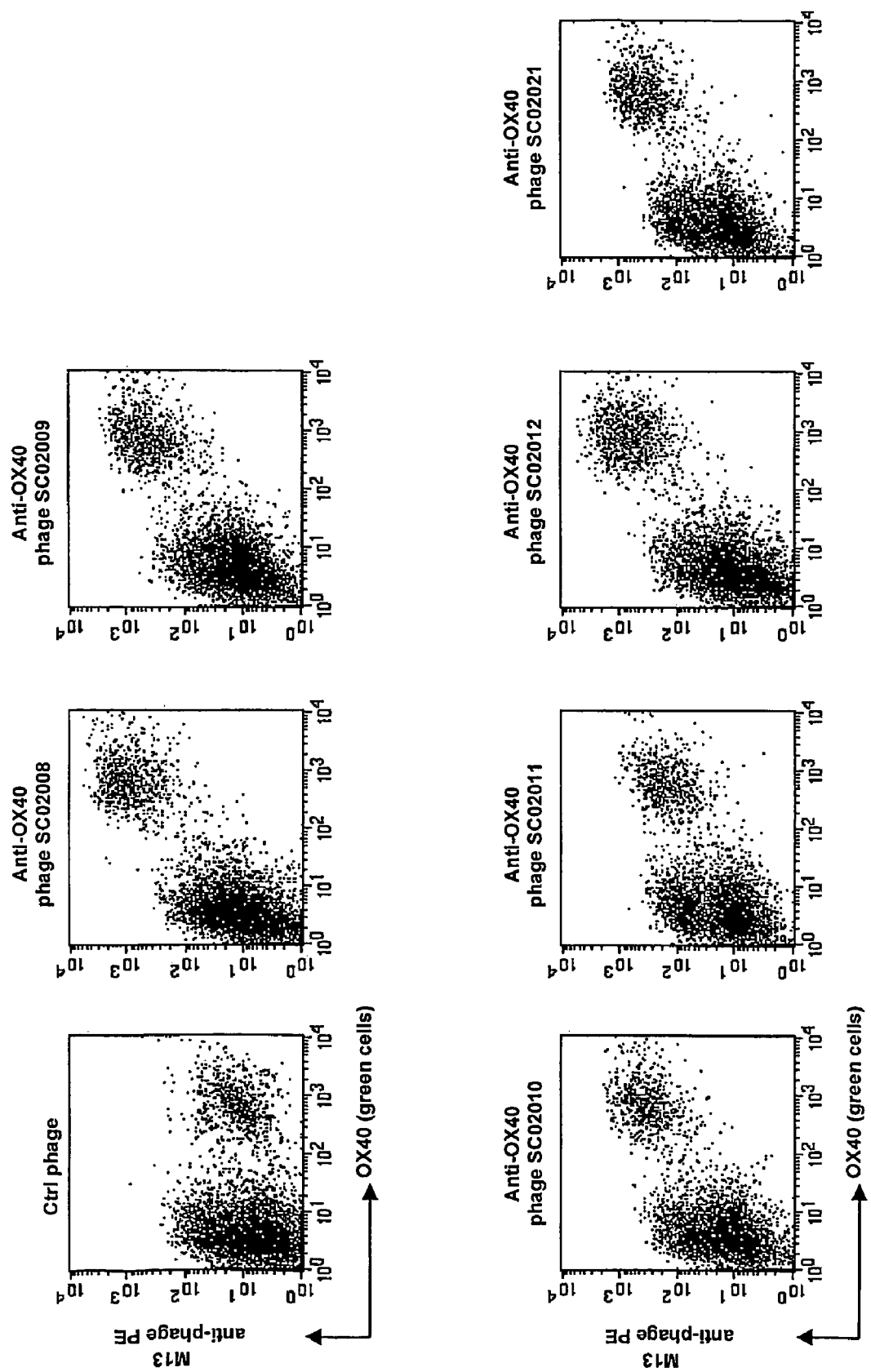
FIG. 2 shows the binding of anti-human OX40-receptor phage antibodies, that were selected using immobilized human OX40-Ig fusion protein, to human OX40-receptor transfected PER.C6™ cells. In each picture the group of cells on the left are control transfected PER.C6™ cells and the group of cells on the right are OX40-receptor transfected PER.C6™ cells. The upper left picture shows binding of a control phage antibody directed against thyroglobulin.

In another assay the phage antibodies were analyzed for their ability to bind PER.C6™ cells that recombinantly express human OX40-receptor. To this purpose PER.C6™ cells were transfected with a plasmid carrying a cDNA sequence encoding human OX40-receptor or with the empty vector and stable transfectants were selected using standard techniques known to a person skilled in the art (Coligan et al., 2001). For flow cytometry analysis, phage antibodies were first blocked in an equal volume of 4% MPBS for 15 minutes at 4° C. prior to the staining of the OX40-receptor- and control transfected PER.C6™ cells. The blocked phages were added to a mixture of unlabelled control transfected PER.C6™ cells and OX40-receptor transfected PER.C6™ cells that were labelled green using a lipophylic dye (PKH67, Sigma). The binding of the phage antibodies to the cells was visualized using a biotinylated anti-M13 antibody (Santa Cruz Biotechnology) followed by streptavidin-phycoerythrin (Caltag). As shown in FIG. 2, the selected anti-human OX40-receptor phage antibodies called SC02008, SC02009, SC02010, SC02011, SC02012 and SC02021 selectively stained the PER.C6™ OX40-receptor transfectant, while they did not bind the control transfectant.

In another assay the phage antibodies were analyzed for their ability to bind to OX40-receptor positive CD4+ T-cells derived from inflamed tonsils or from synovial fluid from patients suffering from rheumatoid arthritis. As a control, the staining pattern of the anti OX40-receptor phage antibodies on peripheral blood mononuclear cells (MNC) is also shown.

Figure 3A:
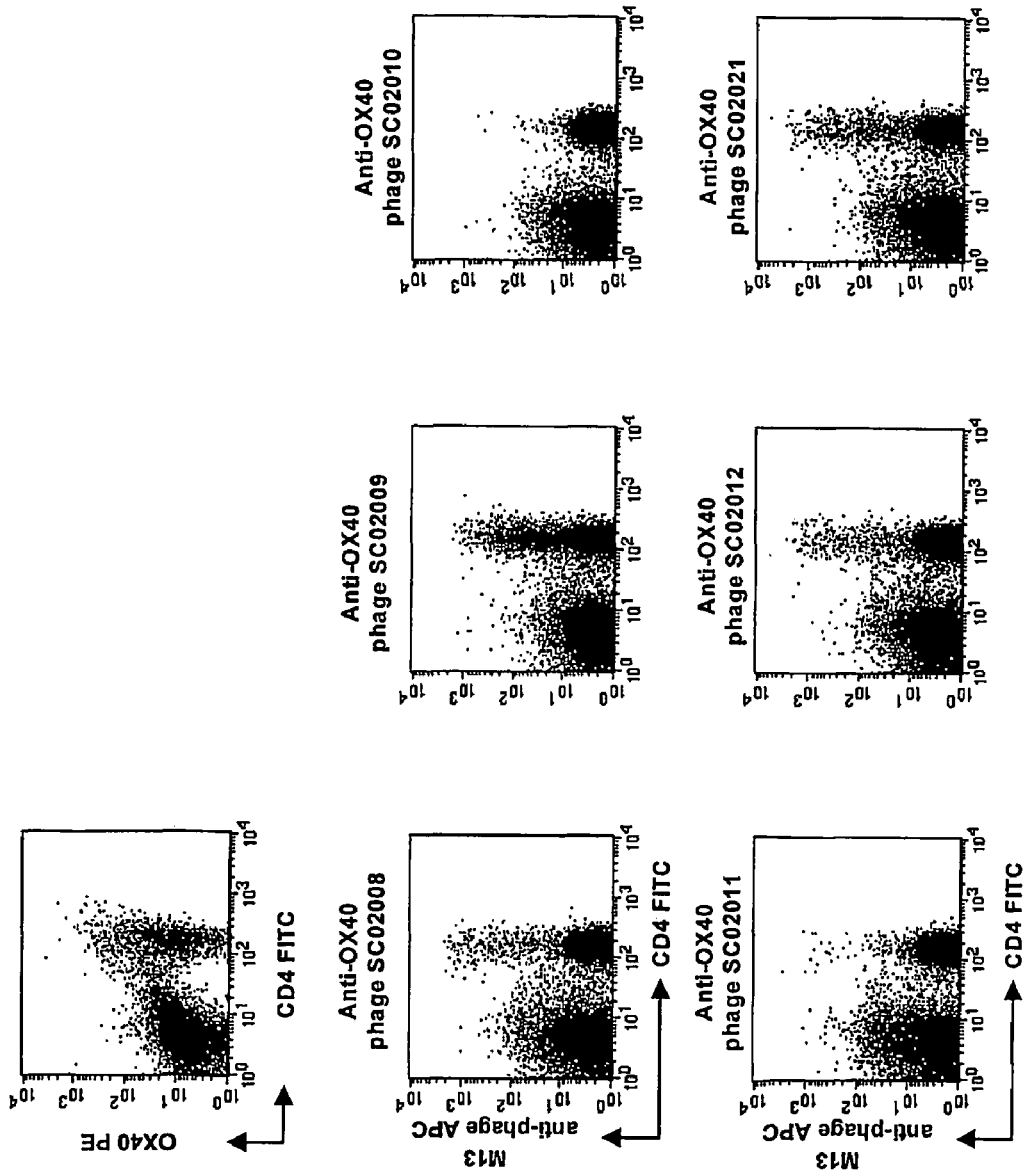
In FIG. 3A the binding of the selected phage antibodies to a subset of CD4+ T-cells within tonsil mononuclear cells is shown.
Figure 3B:
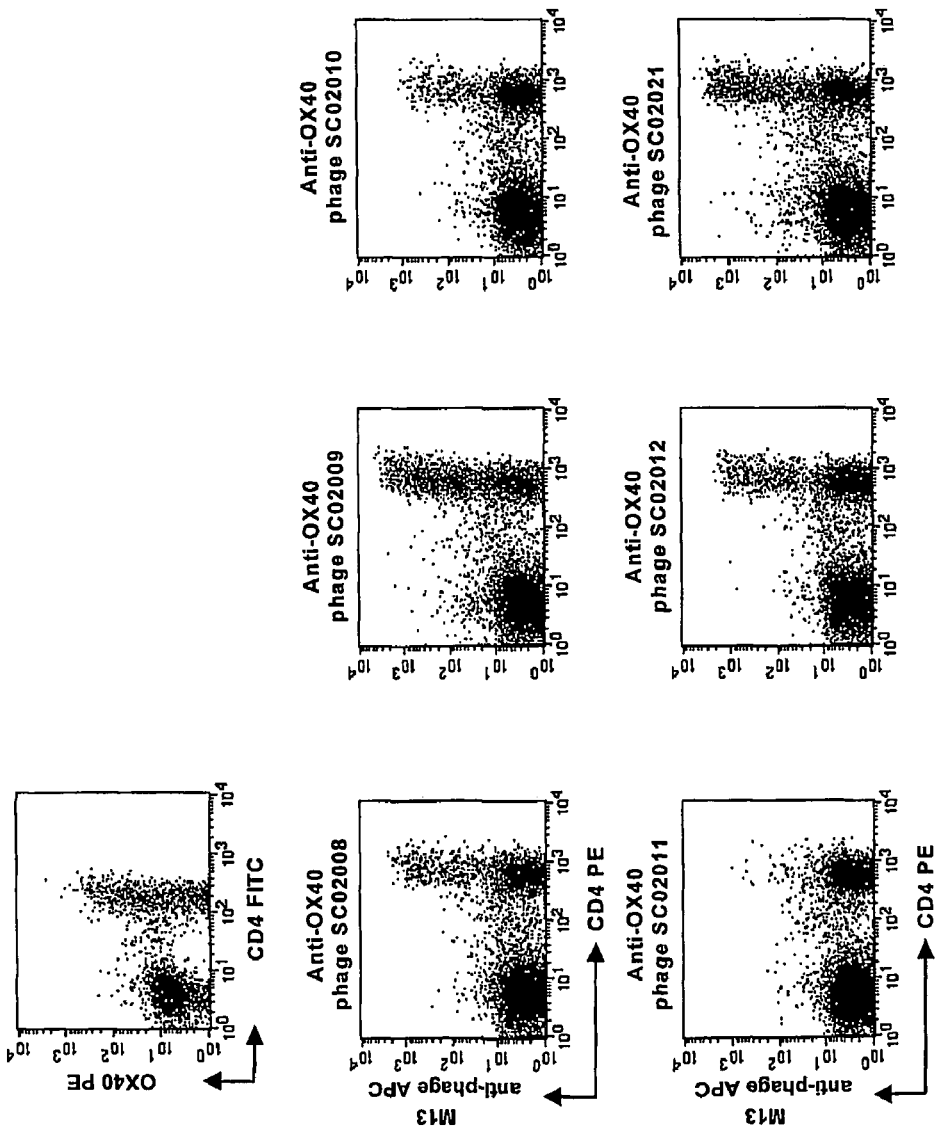
In FIG. 3B the binding of the phage antibodies to a subset of CD4+ T-cells within synovial fluid mononuclear cells is shown.
Figure 3C:
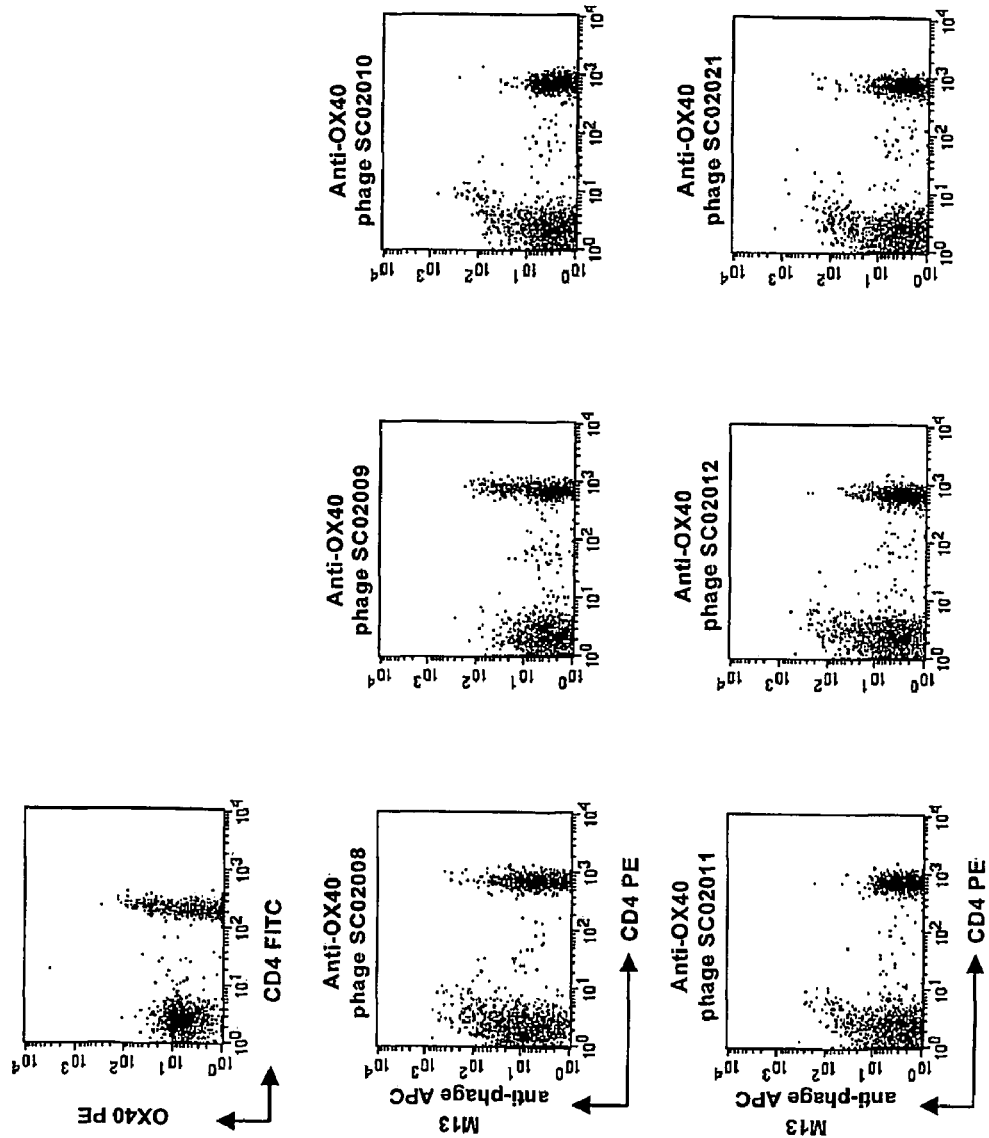
In FIG. 3C the binding of the selected phage antibodies to peripheral blood CD4+ T-cells is displayed. The upper FACS plot in FIGS. 3A, 3B and 3C shows a control staining on CD4+ T cells using a PE-labelled mouse anti-human OX40 antibody.

Inflamed tonsils were obtained from patients undergoing routine tonsillectomy. Tonsils were minced and the MNC fraction was isolated by density centrifugation. Flow cytometric analysis of the binding of the anti-OX40-receptor phage antibodies to the OX40+ CD4+ T-cells was performed as described above. The CD4+ T-cells were distinguished from total tonsil MNC using a FITC conjugated antibody against CD4. As shown in FIGS. 3A and 3B the selected anti-human OX40-receptor phage antibodies called SC02008, SC02009, SC02010, SC02011, SC02012 and SC02021 selectively stain a subset of CD4+ T-cells within tonsil and synovial fluid mononuclear cells respectively, while they display minor staining of peripheral blood CD4+ T-cells (FIG. 3C).

Example 3

Selection of Phage Carrying Single Chain Fv Fragments Specifically Recognizing Human OX40-receptor Using OX40+ CD4+ T-cells.

Figure 4A:
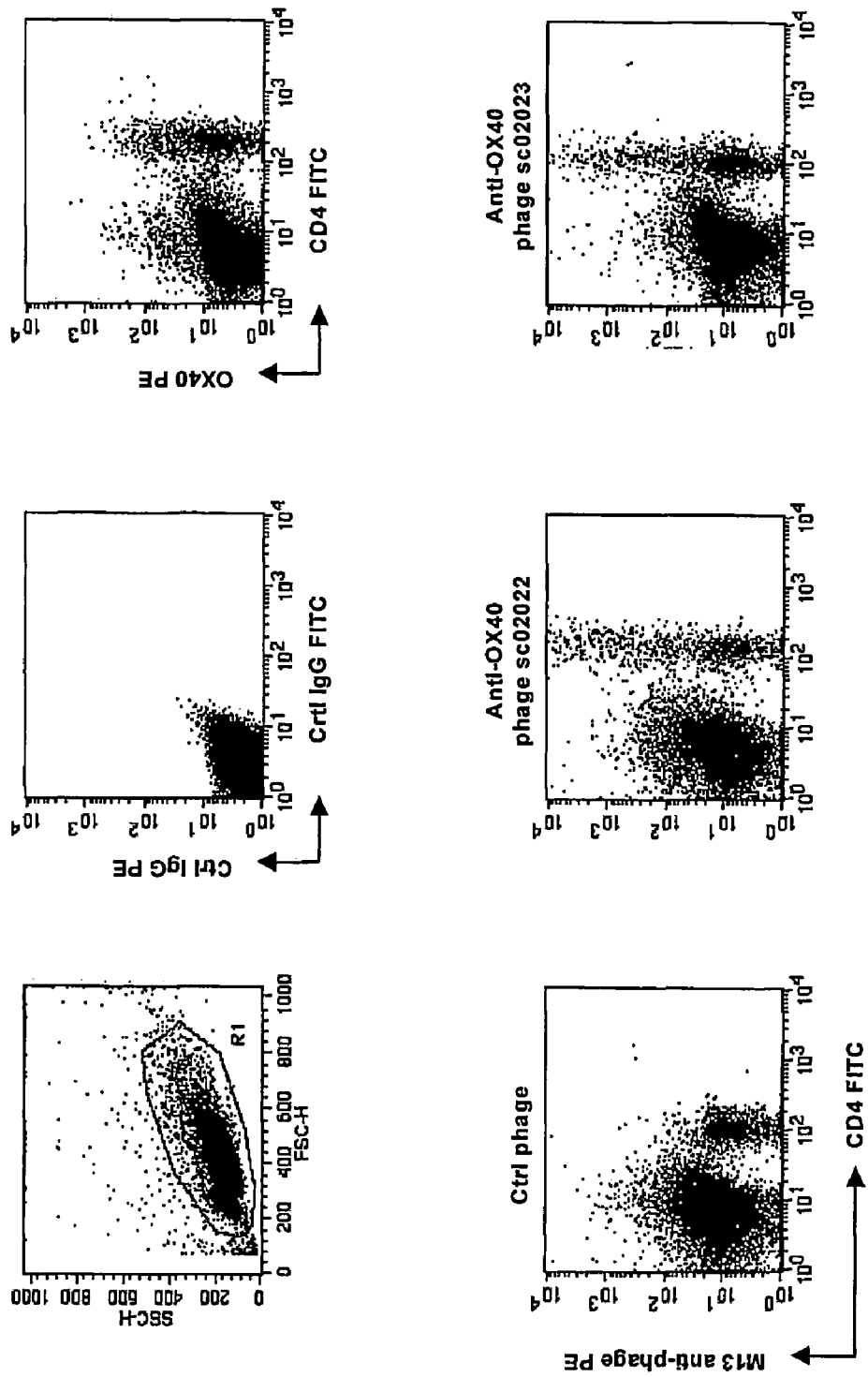
FIG. 4 shows the binding of anti-human OX40-receptor phage antibodies, selected using OX40+ CD4+ T-cells, to OX40+ CD4+ T-cells (see FIG. 4A) and to human OX40-receptor transfected PER.C6™ cells (see FIG. 4B).
Figure 4B:
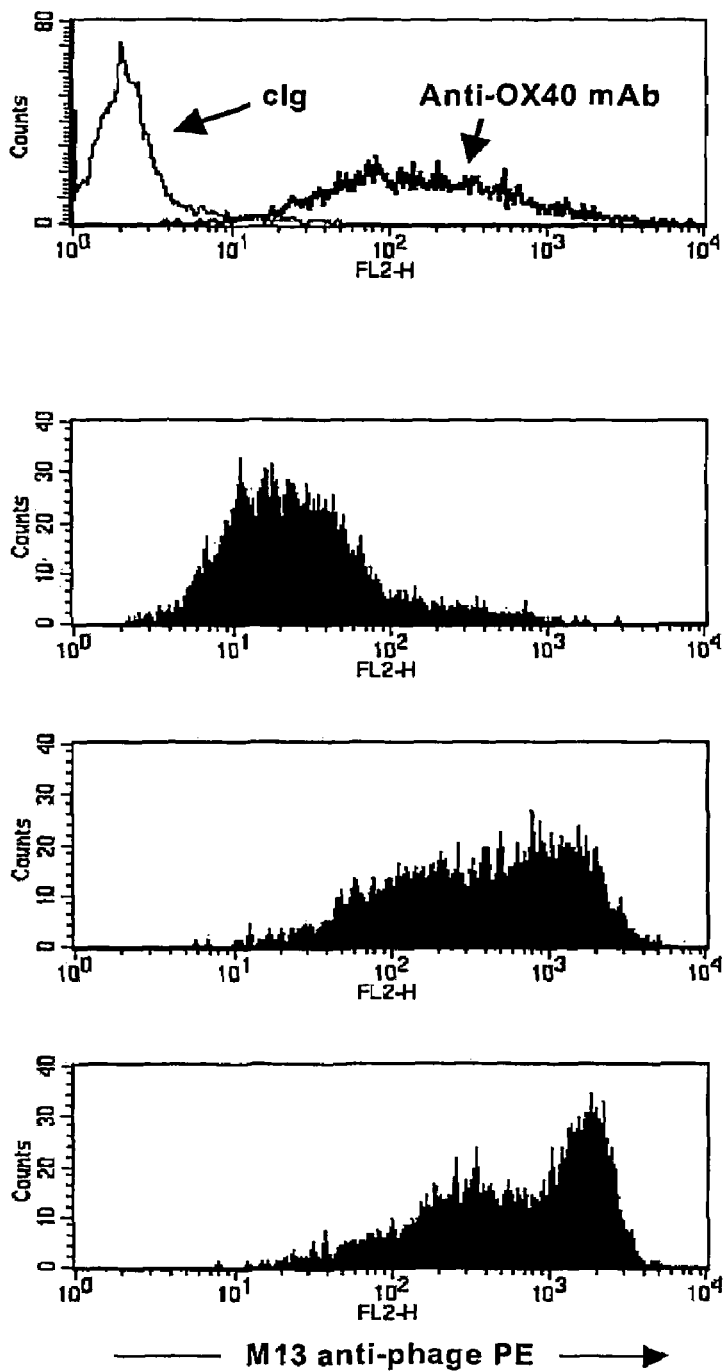

Phage selection experiments were performed as described supra, using lymphocytes as target. An aliquot of the phage library (500 µl, approximately $10^{13}$ cfu) were blocked with 2 ml RPMI/10% FCS/1% NHS for 15 minutes at room temperature. Tonsil MNC (~10×$10^6$ cells) were added to the blocked phage library and incubated for 2.5 hours while slowly rotating at 4° C. Subsequently, the cells were washed twice and were resuspended in 500 µl RPMI/10% FCS and incubated with a FITC-conjugated anti-CD4 antibody (Becton Dickinson) and a phycoerythrin-conjugated anti-OX40-receptor antibody (Becton Dickinson) for 15 minutes on ice. The cells were washed once and transferred to a 4 ml tube. Cell sorting was performed on a FACSvantage fluorescence-activated cell sorter (Becton Dickinson), and ~15.000 CD4+ OX40+ cells were sorted. The sorted cells were spun down, the supernatant was saved and the bound phages were eluted from the cells by resuspending the cells in 500 µl 50 mM glycin pH 2.2 followed by incubation for 5 minutes at room temperature. The mixture was neutralized with 250 µl 1 M Tris-HCl pH 7.4 and added to the rescued supernatant. Collectively these phages were used to prepare an enriched phage library as described earlier. The selection/re-infection procedure was performed twice. After the second round of selection, monoclonal phage antibodies were prepared and tested for binding to tonsillar OX40+ CD4+ T-cells. Selected phage antibodies that met this criterium were subsequently tested for binding to OX40-receptor transfected PER.C6™ cells. The results in FIG. 4 show that the selected phage antibodies called SC02022 and SC02023 selectively bind to a subset of CD4+ T-cells within tonsil mononuclear cells (see FIG. 4A) and that they bind to the human OX40-receptor PER.C6™ transfectant (see FIG. 4B).

Example 4

Characterization of the Human OX40-receptor Specific scFv's.

From the selected human OX40-receptor specific phage antibody (scFv) clones plasmid DNA was obtained and nucleotide sequences were determined according to standard techniques. Nucleotide sequences and amino acid translations of the scFv's called SC02008, SC02009, SC02010, SC02011, SC02012, SC02021, SC02022 and SC02023 are shown in FIGS. 5-12, respectively. The nucleotide sequences of the scFv's called SC02008, SC02009, SC02010, SC02011, SC02012, SC02021, SC02022 and SC02023 are also shown in SEQ ID NO:1, SEQ ID NO:3, SEQ ID NO:5, SEQ ID NO:7, SEQ ID NO:9, SEQ ID NO:11, SEQ ID NO:13 and SEQ ID NO:15, respectively. The amino acid sequences of the scFv's called SC02008, SC02009, SC02010, SC02011, SC02012, SC02021, SC02022 and SC02023 are shown in SEQ ID NO:2, SEQ ID NO:4, SEQ ID NO:6, SEQ ID NO:8, SEQ ID NO:10, SEQ ID NO:12, SEQ ID NO:14 and SEQ ID NO:16, respectively. The VH and VL gene identity and heavy chain CDR3 compositions of the anti-human OX40-receptor scFv's are depicted in table 1.

Example 5

Production of Human OX40-receptor Specific Bivalent scFv in *Pichia Pastoris*.

Figure 13A:
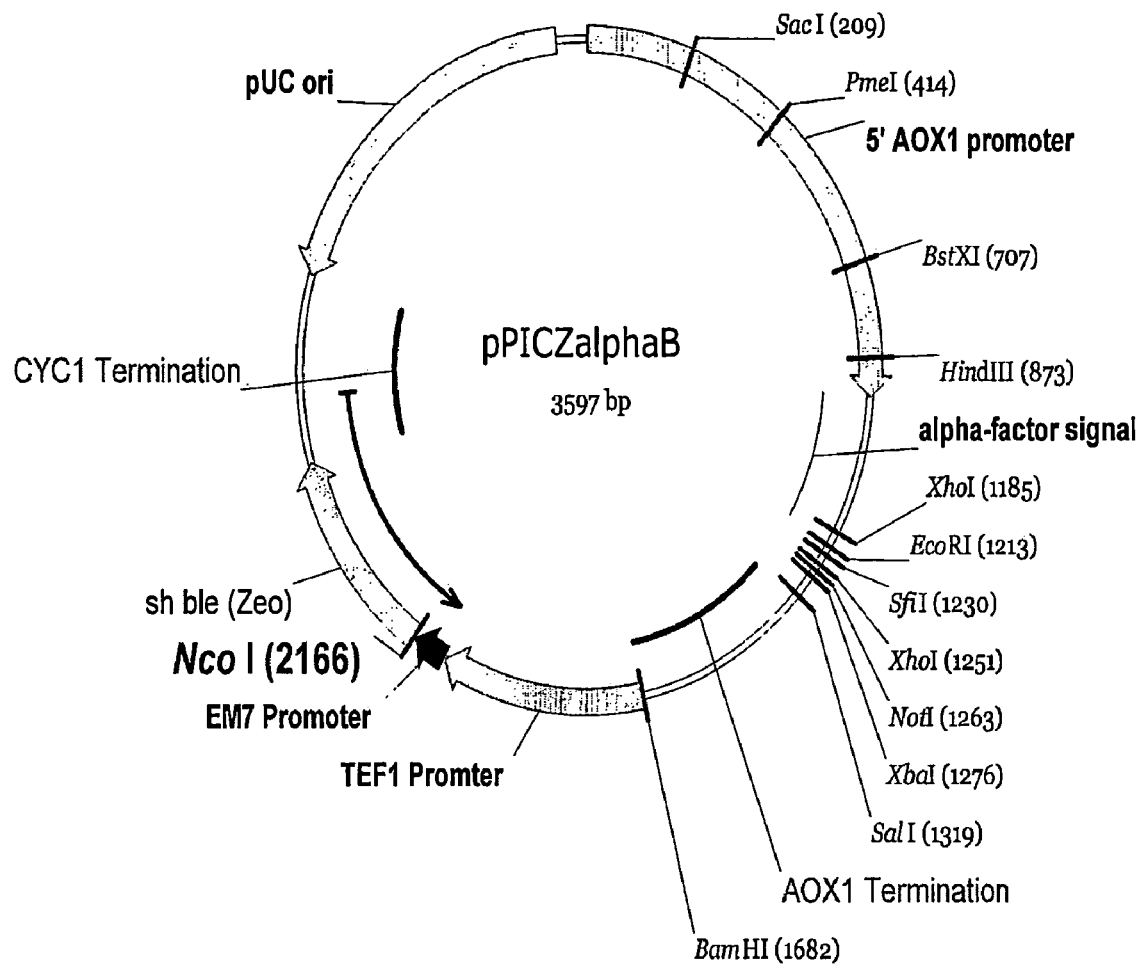
In FIG. 13A the vector pPICZαB is shown and in FIG. 13B the bivalent scFv expression vector pPicZbiFVH is shown.
Figure 13B:
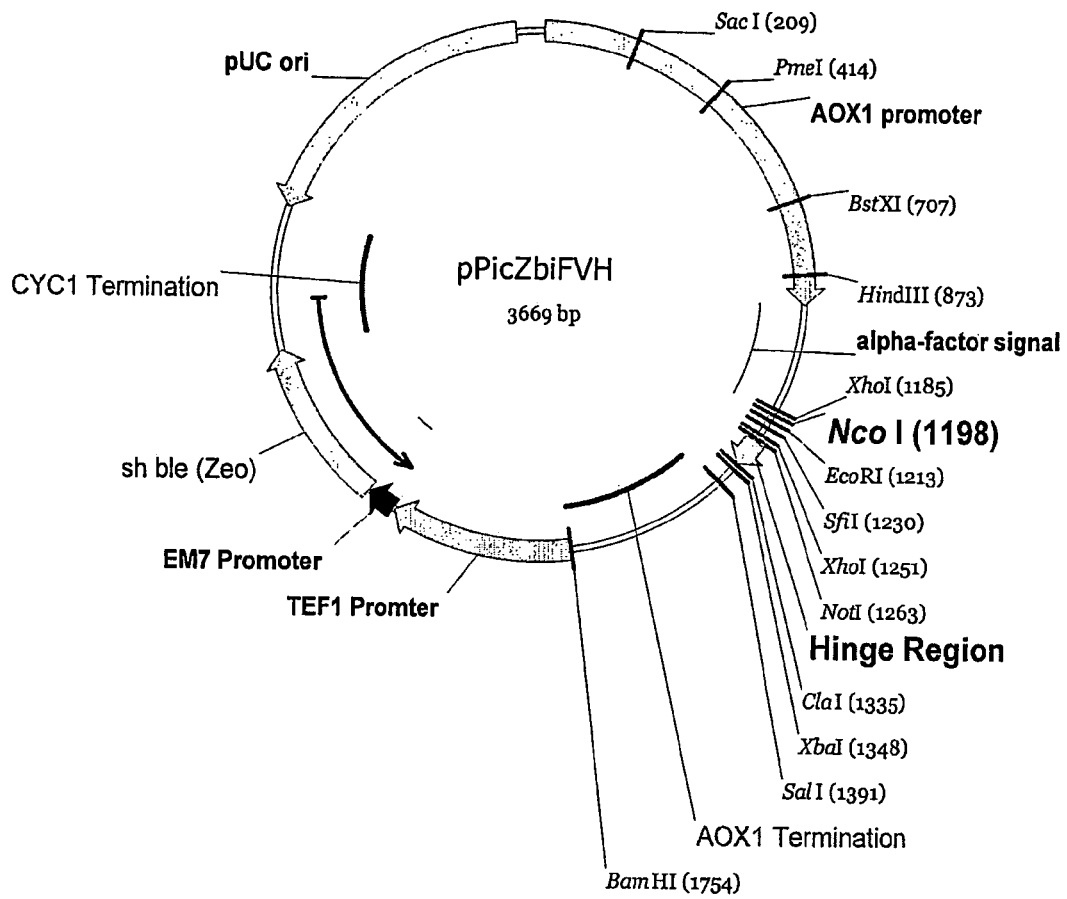
FIG. 13 shows the construction of the bivalent scFv expression vector pPICZbiFVH.
FIG. 13C shows the cloning strategy of scFv's into pPicZbiFVH.

Methods for the cloning and expression of bivalent scFv fragments in the *Pichia pastoris* system were based on protocols provided by the suppler (Invitrogen) in "A Manual of Methods for Expression of Recombinant Proteins Using pPICZ and pPICZα in *Pichia pastoris* (Version F)". The bivalent scFv expression vector pPicZbiFVH (see FIG. 13B) was constructed from the vector pPICZαB (Invitrogen) (see FIG. 13A) following standard molecular biology techniques known to a person skilled in the art. Three modifications were introduced in the pPICZαB (see FIG. 13C):
1. A restriction site (NcoI) was introduced by PCR-generated point mutation directly after the KEK2 cleavage site of the signal peptide to facilitate cloning into the vector.
2. A second NcoI restriction site was removed by PCR generated point mutation inside the coding region of the sh ble gene.
3. A synthetic fragment comprising the hinge region of murine IgG3 and a linker fragment was introduced between the restriction sites NotI and XbaI.

All modifications were confirmed by sequencing. ScFv's were cloned into pPicZbiFVH from the phage display expression vector by directional cloning using the restriction sites NcoI and NotI. The *Pichia pastoris* strain SMD1168 kek1: suc1 (ATCC #204414) was transformed with 5-10 μg of linearized construct cDNA by electroporation according to the manufacturer's protocols (supra). The transformed cells were plated on YPDS agar containing 250 μg/ml Zeocin and incubated at 30° C. for 3-4 days. High producing clones were selected by colony lift immunoblot screening, as follows. Pre-wet nitrocellulose membranes were layered over the transformation plates and a fraction of each colony was lifted onto the membrane. The membrane was then placed colony side up on YPD agar containing 0.5% methanol and incubated overnight at 30° C. The membranes were then washed repeatedly with Tris buffered saline containing 0.5% Tween-20 (TBST) to removed colonies, then blocked for 30 minutes with TBST and 4% non-fat milk powder. The membranes were then placed in TBST containing 4% non-fat milk powder and horseradish peroxidase conjugated anti-c-myc antibody (Roche) for 1 hour. Finally, the membranes were washed extensively in TBST followed by a PBS washing step and scFv-secreting colonies were revealed by a chemofluorescence detection system (Apbiochem). Selected high producers were purified by streaking on YPD plates and were subsequently used for bivalent scFv expression. Small-scale expression cultures were carried out in shaker flasks essentially as described by the manufacturer's protocols (supra). BMGY medium was used for the cell expansion phase, while BMMY medium was used during the bivalent scFv expression phase. After 48 hours of induction supernatants were clarified by repeated centrifugation. The supernatant was conditioned for purification by the addition of 1 M $Na_2HPO_4$ pH 8 to a concentration of 20 mM, 0.5 M Imidazole to a concentration of 10 mM, 5 M NaCl to a concentration of 500 mM. Hereafter, the samples were purified by immobilized metal affinity chromatography followed by anion exchange chromatography on an AKTAprime FPLC-system (Pharmacia). A 5 ml HiTrap™ chelating column (Pharmacia) was charged with $NiSO_4$ and equilibrated according to the manufacturers instructions. Conditioned supernatant was loaded directly on to the column and washed extensively in equilibration buffer (20 mM $Na_2PO_4$ pH 8, 10 mM imidazole). Bivalent scFv were eluted directly off the column on to a 1 ml sepharose Q HP column (Pharmacia) in the presence of 250 mM imidazole pH 8.5. The column was then washed in 20 mM Tris-HCl pH 8, then briefly in 20 mM $Na_2PO_4$ pH 7.3, and bivalent scFv's were eluted off the column over a gradient of 0-0.5 M NaCl in 7 column volumes. Fractions were then measured for protein content and were analyzed for activity and purity. The bivalent scFv clones of SC02008, SC02010, SC02011 and SC02023 were deposited at the European Collection of Cell Cultures (ECACC), CAMR, Salisbury, Wiltshire SP4 OJG, Great Britain on 15 May 2002, under accession numbers 02051563, 02051560, 02051561 and 02051562, respectively.

Example 6

Functional Analysis of Bivalent scFv Specifically Recognizing Human OX40-receptor.

The anti human-OX40-receptor bivalent scFv's were validated for their ability to bind to OX40+ CD4+ T-cells within tonsil MNC. Tonsil MNC samples were obtained as described supra and were stained with the bivalent scFv's at a concentration of 5 μg/ml at 4° C. Binding of the bivalent scFv's was visualized using a biotinylated anti-myc antibody (9E10, Santa Cruz Biotechnology) followed by streptavidin-phycoerythrin (Caltag). The bivalent anti human-OX40-receptor scFv's displayed a similar staining pattern as the corresponding scFv's in phage antibody format.

Figure 14A:
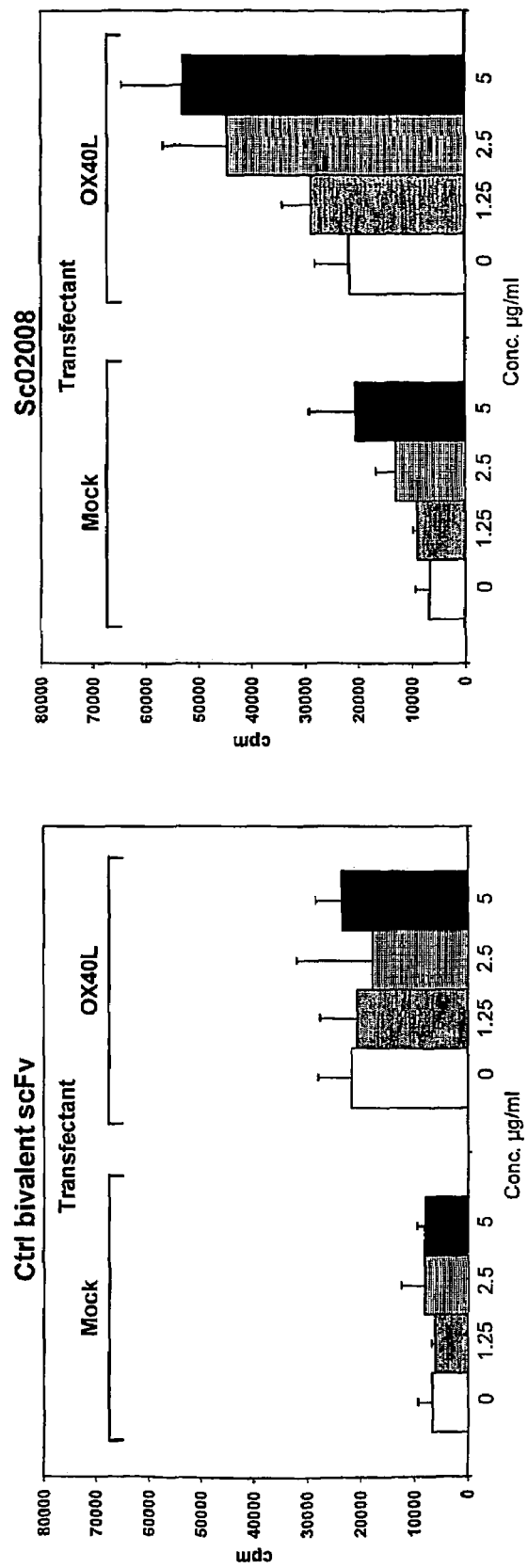
FIG. 14A shows the stimulation assay for the bivalent scFv SC02008 and FIG. 14B shows the stimulation assay for the bivalent scFv SC02023.
Figure 14B:
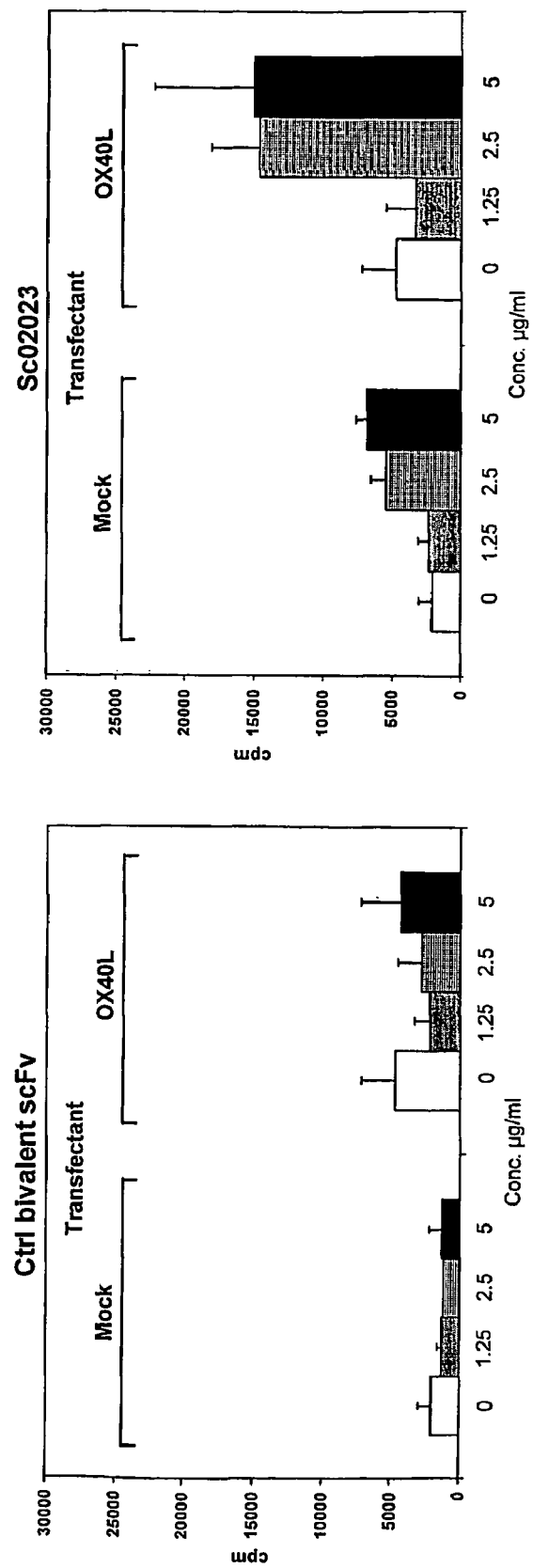

The anti-human OX40-receptor bivalent scFv's were analyzed for their ability to interfere with OX40-receptor-mediated signaling in a costimulation assay. For this purpose 293T cells were transfected with either the empty vector or with an OX40-ligand cDNA-containing plasmid (pCDNA3.1zeo(+), In Vitrogen) using the lipofectamine reagent according to standard protocols. 48 hours after transfection, the cells were harvested, paraformaldehyde fixed and analyzed for cell surface expression of OX40-ligand by flow cytometry (OX40-ligand was visualized using the OX40-Ig fusion protein followed by incubation with a biotinylated goat-anti-human Fc polyclonal antibody (Caltag) and streptavidin-phycoerythrin (Caltag)). To cocultures of $1.5 \times 10^3$ 293T transfectants and $4 \times 10^5$ T-cells, which were activated with a submitogenic dose of 50 ng/ml of PHA (Abbot Murex), several concentrations of the bivalent anti-human-OX40-receptor or control scFv's were added. T-cells were purified via negative selection using the MACS system and a pan-T cell isolation kit (Myltenyi Biotec) from PBMC that were obtained from healthy donors by Ficoll-Hypaque density gradients. The cultures were performed in U-bottom 96 well plates for 5 days and the proliferation of the T-cells was measured by $^3$H-thymidine incorporation during the last 16 hours of culture. As shown in FIGS. 14A and 14B, the bivalent scFv's SC02008 and SC02023, respectively, display agonistic (stimulating) function in that they induce T-cell proliferation in a concentration dependent manner when incubated with the mock-transfected 293T cells. Interestingly, these agonistic bivalent anti human-OX40-receptor scFv's demonstrate a synergistic stimulatory effect when co-incubated with the OX40-ligand transfected 293T cells as compared to the level of proliferation that is reached with the same transfectant in the presence of a control bivalent scFv antibody.

Example 7

Construction of Fully Human Immunoglobulin Molecules from the Selected Anti-human OX40-receptor Single Chain Fv Fragments.

To use the selected antibody fragments that recognize human OX40-receptor for therapeutic applications in humans, it is desirable to generate human immunoglobulin molecules. The engineering and production of the human IgG1 monoclonal antibodies is essentially performed as described in detail by Boel et al. (2000). In detail, scFv were recloned in IgG expression vector C01 (pCRU-KO1). To that purpose, $V_H$ and $V_L$ regions were PCR amplified using designated primers to append restriction sites and restore complete human frameworks. The PCR fragments were cloned in pTOPO (Invitrogen), the integrity of the PCR-fragments was verified by sequencing and thereafter the inserts were sequentially cloned (EcoRI-BamHI for V$_H$ and XhoI-NotI for V$_L$) into the IgG expression vector C01.

| ScFv | 5'V$_H$ oligo | 3'V$_H$ oligo | 5'V$_L$ oligo | 3'V$_L$ oligo |
|---|---|---|---|---|
| 02-008 | 5H-B | 3H-B | 5K-E | 3K-E |
| 02-011 | 5H-B | 3H-B | 5K-E | 3K-E |
| 02-021 | 5H-B | 3H-B | 5K-G | 3K-B |
| 02-023 | 5H-B | 3H-B | 5K-H | 3K-F | primer sequences:

5H-B:
acctgtcttgaattctccatggccgaggtgcagctggtggagtctg         (SEQ ID NO: 47)

3H-B:
gctcgcggatccactcacctgaggagacggtcaccagggtgccctggcccc    (SEQ ID NO: 48)

5K-E:
acctgtctcgagttttccatggctgacatcgtgatgacacagtctccag      (SEQ ID NO: 49)

5K-G:
acctgtctcgagttttccatggctgacatcgtgatgacccagtctcc        (SEQ ID NO: 50)

5K-H:
acctgtctcgagttttccatggctgaaattgtgctcacacagtctccagccacc (SEQ ID NO: 51)

3K-E:
ttttccttagcggccgcaaagtgcacttacgtttgatttccagtttggtgccctg (SEQ ID NO: 52)

3K-B:
ttttccttagcggccgcaaagtgcacttacgtttgatttccactttggtgccctg (SEQ ID NO: 53)

3K-F:
ttttccttagcggccgcaaagtgcacttacgtttgatctccaccttggtccctcc (SEQ ID NO: 54)

The resulting expression constructs pgG102-008C01, pgG102-011C01, pgG102-021C01 and pgG102-023C01 encoding the human IgG1 antibodies directed against human-OX40 receptor were transiently expressed in PER.C6™ cells and supernatants containing IgG1 antibodies were obtained. The expression constructs pgG102-008C01, pgG102-011C01, pgG102-021C01 and pgG102-023C01 were deposited at the European Collection of Cell Cultures (ECACC), CAMR, Salisbury, Wiltshire SP4 OJG, Great Britain on 9 Jun. 2003, under provisional accession numbers 03060601, 03060602, 03060603 and 03060604, respectively.

The nucleotide sequences of the heavy chains of the antibodies called 008, 011, 021 and 023 are shown in SEQ ID NOS:39-42, respectively. The amino acid sequences of the heavy chains of the antibodies called 008, 011, 021 and 023 are shown in SEQ ID NOS:25-28, respectively. The nucleotide sequences of the light chains of the antibodies called 008, 011, 021 and 023 are shown in SEQ ID NOS:43-46, respectively. The amino acid sequences of the light chains of the antibodies called 008, 011, 021 and 023 are shown in SEQ ID NOS:29-32, respectively. Subsequently, the antibodies were purified over size-exclusion columns and protein A columns using standard purification methods used generally for immunoglobulins (see for instance WO 00/63403).

Figure 15:
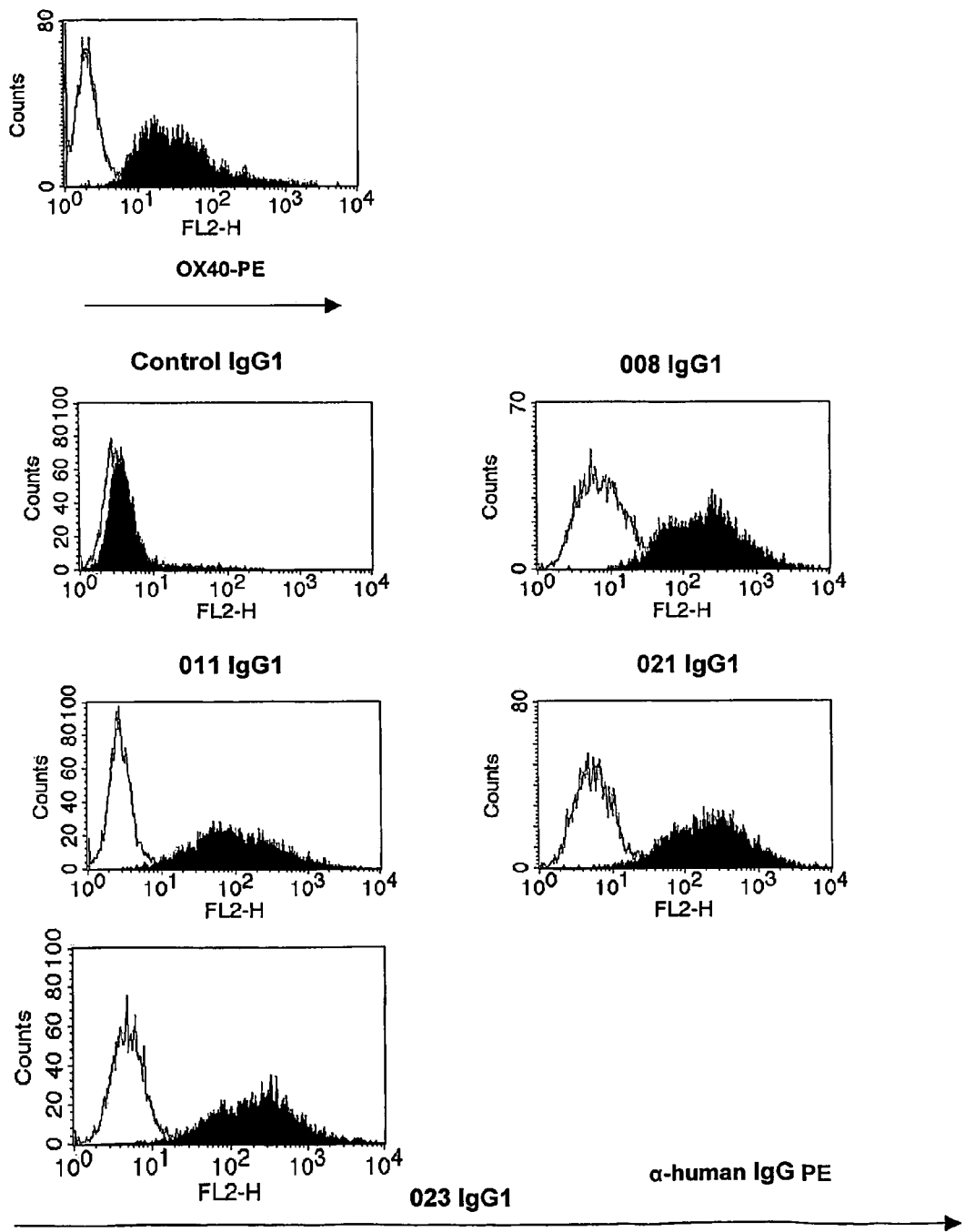
FIG. 15 shows the binding of human IgG molecules called 008, 011, 021 and 023 to human OX40-receptor transfected PER.C6™ cells.

The anti-OX40 receptor IgG1 antibodies were validated for their ability to bind to PER.C6™ cells transfected with human OX40-receptor. To this purpose mock- and human OX40-receptor-transfected cells were stained with the IgG1 antibodies at a concentration of 20 μg/ml at 4° C. Binding of the antibodies called 008, 011, 021 and 023 was visualized using biotinylated goat-anti-human IgG (Fc specific, Caltag) followed by streptavidin-phyco-erythrin (Caltag). The stained cells were analyzed by flow cytometry. All antibodies specifically recognized the human OX40-receptor on OX40-receptor-transfected PER.C6™ cells (filled histograms in FIG. 15,) while they did not bind the mock-transfected cell line (open histograms in FIG. 15).

Example 8

Functional Analysis of Fully Human IgG Molecules Specifically Recognizing Human OX40-receptor.

The anti-OX40-receptor IgG1 molecules are validated for their ability to interfere with OX40R-mediated signaling in a costimulation assay as described supra. It is to be expected that at least one of the IgG1 molecules stimulates T-cell proliferation.

Example 9

Immunohistochemistry

The anti-OX40-receptor IgG molecules are biotinylated and subsequently analyzed for their ability to bind to OX40+ cells in inflamed tonsil and tumor sections with infiltrating lymphocytes by immunohistochemistry. Furthermore, they are analyzed for their ability to bind to normal tissues. To this purpose, frozen sections of the following normal tissues: adrenal gland; bladder; brain (cerebellum and cerebrum); blood vessels (aorta and coronary artery); fallopian tube; oesophagus; stomach (antrum and body); duodenum; ileum; colon; heart; kidney; liver; lung; lymphnode; ovary; pancreas; parathyroid; peripheral nerve; pituitary gland; placenta; prostate; salivary gland; skin; spinal cord; spleen; striated muscle; testis; tonsil; thyroid; ureter and uterus (cervix and endometrium) as well as inflamed tissues and tumor tissues are cut, mounted on glass slides and are dried at room temperature. The sections are blocked for endogenous peroxidase with 50 mM sodium azide containing 0.03% $H_2O_2$ for 20 minutes, followed by blocking for endogenous biotin according to the provided protocol (X0590, Dako). Subsequently, the sections are blocked with PBS containing 4% BSA and 10% normal human serum prior to incubation with the biotinylated anti-human OX40 receptor IgG's for 60 minutes at room temperature. To detect bound IgG molecules the sections are incubated with streptavidin coupled-horseradish peroxidase (Dako) followed by incubation with diaminobenzidine (Sigma) resulting in a local deposition of brown crystals. The sections are counterstained with hematoxilin to visualize nucleated cells within the sections. Prior to analysis the sections are dehydrated and the slides are sealed with eukitt (BDH).

Example 10

In vivo Analysis of Enhanced Immune Response Induced by Agonistic Anti-human OX40-receptor Binding Molecules.

To determine the cross-reactivity of the anti-human OX40-receptor antibodies with mouse OX40-receptor, splenic OX40+ CD4+ T-cells are analyzed by flow cytometry. Murine OX40+ T-cells are generated by stimulating C57B16 splenic CD4 T-cells that are isolated using an anti-CD4-phycoerythrin antibody (Pharmingen) and anti-phycoerythrin labeled MACS beads (Myltenyi Biotec) with a mitogenic dose of PHA and IL2. The cells are analyzed after 72 hours of stimulation with a rat antibody against the murine OX40-receptor and with the panel of anti-human OX40-receptor antibodies (supra). In case the agonistic anti-human OX40-receptor antibodies display cross reactivity with mouse OX40-receptor, the OX40-receptor can be engaged in vivo with these agonistic antibodies to demonstrate the delivery of a costimulatory signal to effector T-cells. To demonstrate the effect of providing an agonistic anti-OX40-receptor antibody to T-cells during tumor priming in vivo, a MCA 303 sarcoma tumor model in C57BL/6 mice is used as described by Weinberg et al. (2000) and in WO 99/42585. Mice are inoculated subcutaneously at day 0 with $1-3 \times 10^5$ MCA 303 sarcoma tumor cells. Three days later the animals are given intraperitoneal injections with the agonistic anti-human OX40-receptor antibodies at doses ranging from 100-500 μg per animal. A second dose is given 7 days after tumor inoculation. The animals are then monitored for tumor growth for over 50 days, animals are sacrificed when tumor sizes exceed 1 cubic cm. When animals that are given the agonistic anti-human OX40-receptor antibodies remain tumor free (or have tumours smaller in size than control animals), while animals that are given the tumor cells alone have to be sacrificed, this indicates that engagement of the OX40-receptor by the agonistic anti-human OX40-receptor antibodies costimulate effector T-cells to exert their tumor eradicating function. Alternatively, the experiment described above can also be performed in a transgenic mouse model in which human OX40-receptor is expressed under a T-cell specific promoter. Such a mouse can be created according to protocols known to the person skilled in the art of transgenic mouse models.

TABLE 1

| Name scFv | SEQ ID NO of nucleotide sequence | SEQ ID NO of amino acid sequence | CDR3 | $V_H$-germline | $V_L$-germline |
|---|---|---|---|---|---|
| SC02-008 | SEQ ID NO: 1 | SEQ ID NO: 2 | DRYSQVHYAL DY (SEQ ID NO: 17) | $V_H$3 DP47 | $V_K$II |
| SC02-009 | SEQ ID NO: 3 | SEQ ID NO: 4 | DRYVNTSNAF DY (SEQ ID NO: 18) | $V_H$3 DP29 | $V_K$II |
| SC02-010 | SEQ ID NO: 5 | SEQ ID NO: 6 | DMSGFHEFDY (SEQ ID NO: 19) | $V_H$3 DP49 | $V_K$I |
| SC02-011 | SEQ ID NO: 7 | SEQ ID NO: 8 | DRYFRQQNAF DY (SEQ ID NO: 20) | $V_H$3 DP47 | $V_K$II |
| SC02-012 | SEQ ID NO: 9 | SEQ ID NO: 10 | ARAAGTIFDY (SEQ ID NO: 21) | $V_H$3 DP29 | $V_K$II |
| SC02-021 | SEQ ID NO: 11 | SEQ ID NO: 12 | DRYITLPNALD Y (SEQ ID NO: 22) | $V_H$3 DP50 | $V_K$II |
| SC02-022 | SEQ ID NO: 13 | SEQ ID NO: 14 | YDEPLTIYWFD S (SEQ ID NO: 23) | $V_H$3 DP44 | $V_K$III |
| SC02-023 | SEQ ID NO: 15 | SEQ ID NO: 16 | YDNVMGLYWF DY (SEQ ID NO: 24) | $V_H$3 DP52 | $V_K$II |

REFERENCES

Al-Shamkhani, A., Birkeland, M. L., Puklavec, M., Brown, M. H., James, W., and Barclay, A. N. (1996) OX40 is differentially expressed on activated rat and mouse T cells and is the sole receptor for the OX40 ligand. Eur J Immunol 26:1695-1699.

Boel E, Verlaan S, Poppelier M J, Westerdaal N A, Van Strijp J A and Logtenberg T (2000) Functional human monoclonal antibodies of all isotypes constructed from phage display library-derived single-chain Fv antibody fragments. J Immunol Methods 239:153-166.

Burton D R and Barbas C F (1994) Human antibodies from combinatorial libraries. Adv Immunol 57:191-280.

Coligan J E, Dunn B M, Ploegh H L, Speicher D W and Wingfield P T (eds.) (2001) Current protocols in protein science, volume I. John Wiley & Sons, Inc., New York.

De Kruif J, Terstappen L, Boel E and Logtenberg T (1995a) Rapid selection of cell subpopulation-specific human monoclonal antibodies from a synthetic phage antibody library. Proc Natl Acad Sci USA 92:3938.

De Kruif J, Boel E and Logtenberg T (1995b) Selection and application of human single chain Fv antibody fragments from a semi-synthetic phage antibody display library with designed CDR3 regions. J Mol Biol 248:97.

Huls G, Heijnen I J, Cuomo E, van der Linden J, Boel E, van de Winkel J and Logtenberg T (1999) Antitumor immune effector mechanisms recruited by phage display-derived fully human IgG1 and IgA1 monoclonal antibodies. Cancer Res 59: 5778-5784.

Kaleeba, J. A., Offner, H., Vandenbark, A. A., Lublinski, A., and Weinberg, A. D. (1998) The OX-40 receptor provides a potent co-stimulatory signal capable of inducing encephalitogenicity in myelin-specific CD4+ T cells. Int Immunol 10:453-461.

Kohler G and Milstein C (1975) Continuous cultures of fused cells secreting antibody of predefined specificity. Nature 256:495-497.

Lekkerkerker A and Logtenberg T (1999) Phage antibodies against human dendritic cell populations obtained by flow cytometry-based selection on freshly isolated cells. J Immunol Methods 231:53-63.

Sambrook and Russell (2001) Molecular Cloning, a Laboratory Manual, third edition. Cold Spring Harbor Laboratory Press, Cold Spring Harbor, N.Y.

Van Kroonenburgh, M. J., and Pauwels, E. K. (1988) Human immunological response to mouse monoclonal antibodies in the treatment or diagnosis of malignant diseases. Nucl Med Commun 9:919-930.

Weinberg, A. D., Rivera, M. M., Prell, R., Morris, A., Ramstad, T., Vetto, J. T., Urba, W. J., Alvord, G., Bunce, C., and Shields, J. (2000) Engagement of the OX-40 receptor in vivo enhances antitumor immunity. J Immunol 164:2160-2169.

SEQUENCE LISTING

```
<160> NUMBER OF SEQ ID NOS: 54

<210> SEQ ID NO 1
<211> LENGTH: 769
<212> TYPE: DNA
<213> ORGANISM: Artificial sequence
<220> FEATURE:
<223> OTHER INFORMATION: scFv SC02008
<220> FEATURE:
<221> NAME/KEY: CDS
<222> LOCATION: (3)..(767)
<223> OTHER INFORMATION: Source of genetic material is Homo sapiens

<400> SEQUENCE: 1 cc atg gct gag gtg cag ctg gtg gag tct ggg gga ggc ttg gtc cag          47
   Met Ala Glu Val Gln Leu Val Glu Ser Gly Gly Gly Leu Val Gln
   1               5                  10                  15 cct gga ggg tcc ctg aga ctc tcc tgt gca gcc tct gga ttc acc ttt         95
Pro Gly Gly Ser Leu Arg Leu Ser Cys Ala Ala Ser Gly Phe Thr Phe
            20                  25                  30 agc aac tac acg atg aac tgg gtc cgc cag gcg ccc ggg aag ggg ctg        143
Ser Asn Tyr Thr Met Asn Trp Val Arg Gln Ala Pro Gly Lys Gly Leu
        35                  40                  45 gag tgg gtc tca gct att agt ggt agt ggt ggt agc aca tac tac gca        191
Glu Trp Val Ser Ala Ile Ser Gly Ser Gly Gly Ser Thr Tyr Tyr Ala
    50                  55                  60 gac tcc gtg aag ggc cgg ttc acc atc tcc aga gac aat tcc aag aac        239
Asp Ser Val Lys Gly Arg Phe Thr Ile Ser Arg Asp Asn Ser Lys Asn
65                  70                  75 acg ctg tat ctg caa atg aac agc ctg aga gcc gag gac acg gcc gtg        287
Thr Leu Tyr Leu Gln Met Asn Ser Leu Arg Ala Glu Asp Thr Ala Val
80                  85                  90                  95 tat tac tgt gcc aaa gac cgc tac tcc cag gtg cac tac gcg ttg gat        335
Tyr Tyr Cys Ala Lys Asp Arg Tyr Ser Gln Val His Tyr Ala Leu Asp
                100                 105                 110 tac tgg ggc cag ggc acc ctg gtg acc gtg ctc gag ggt acc gga ggt        383
Tyr Trp Gly Gln Gly Thr Leu Val Thr Val Leu Glu Gly Thr Gly Gly
            115                 120                 125 tcc ggc gga acc ggg tct ggg act ggt acg agc gag ctc gac atc cag        431
Ser Gly Gly Thr Gly Ser Gly Thr Gly Thr Ser Glu Leu Asp Ile Gln
        130                 135                 140 atg acg cag tct cca gac tca ctg ccc gtc acc cct gga gag ccg gcc        479
Met Thr Gln Ser Pro Asp Ser Leu Pro Val Thr Pro Gly Glu Pro Ala
    145                 150                 155 tcc atc tcc tgc agg tct agt cag agc ctc ctg cat agt aat gga tac        527
Ser Ile Ser Cys Arg Ser Ser Gln Ser Leu Leu His Ser Asn Gly Tyr
160                 165                 170                 175 aac tat ttg gat tgg tac ctg cag aag gca ggg cag tct cca cag ctc        575
Asn Tyr Leu Asp Trp Tyr Leu Gln Lys Ala Gly Gln Ser Pro Gln Leu
                180                 185                 190
```

```
ctg atc tat ttg ggt tct aat cgg gcc tcc ggg gtc cct gac agg ttc     623
Leu Ile Tyr Leu Gly Ser Asn Arg Ala Ser Gly Val Pro Asp Arg Phe
        195                 200                 205 agt ggc agt gga tca ggc aca gat ttt aca ctg aaa atc agc aga gtg     671
Ser Gly Ser Gly Ser Gly Thr Asp Phe Thr Leu Lys Ile Ser Arg Val
    210                 215                 220 gag gct gag gat gtt ggg gtt tat tac tgc cag cag tac tac aac cac     719
Glu Ala Glu Asp Val Gly Val Tyr Tyr Cys Gln Gln Tyr Tyr Asn His
225                 230                 235 ccg acg acc ttc ggc cag ggc acc aaa ctg gaa atc aaa cgc gcg gcc     767
Pro Thr Thr Phe Gly Gln Gly Thr Lys Leu Glu Ile Lys Arg Ala Ala
240                 245                 250                 255 gc                                                                   769

<210> SEQ ID NO 2
<211> LENGTH: 255
<212> TYPE: PRT
<213> ORGANISM: Artificial sequence
<220> FEATURE:
<223> OTHER INFORMATION: scFv SC02008

<400> SEQUENCE: 2

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Asn Tyr Thr Met Asn Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Arg Tyr Ser Gln Val His Tyr Ala Leu Asp Tyr
            100                 105                 110

Trp Gly Gln Gly Thr Leu Val Thr Val Leu Glu Gly Thr Gly Gly Ser
        115                 120                 125

Gly Gly Thr Gly Ser Gly Thr Gly Thr Ser Glu Leu Asp Ile Gln Met
    130                 135                 140

Thr Gln Ser Pro Asp Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Ala Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Gly Thr Asp Phe Thr Leu Lys Ile Ser Arg Val Glu
    210                 215                 220

Ala Glu Asp Val Gly Val Tyr Tyr Cys Gln Gln Tyr Tyr Asn His Pro
225                 230                 235                 240

Thr Thr Phe Gly Gln Gly Thr Lys Leu Glu Ile Lys Arg Ala Ala
                245                 250                 255

<210> SEQ ID NO 3
```

```
<211> LENGTH: 775
<212> TYPE: DNA
<213> ORGANISM: Artificial sequence
<220> FEATURE:
<223> OTHER INFORMATION: scFv SC02009
<220> FEATURE:
<221> NAME/KEY: CDS
<222> LOCATION: (3)..(773)
<223> OTHER INFORMATION: Source of genetic material is Homo sapiens

<400> SEQUENCE: 3 cc atg gct gag gtg cag ctg gtg gag tct ggg gga ggc ttg gtc cag        47
   Met Ala Glu Val Gln Leu Val Glu Ser Gly Gly Gly Leu Val Gln
   1               5                   10                  15 cct ggg ggg tcc ctg aga ctc tcc tgt gca gcc tct gga ttc acc ttc       95
Pro Gly Gly Ser Leu Arg Leu Ser Cys Ala Ala Ser Gly Phe Thr Phe
                20                  25                  30 agc ggc tac tct atg aac tgg gtc cgc cag gcg ccc ggg aag ggg ctg      143
Ser Gly Tyr Ser Met Asn Trp Val Arg Gln Ala Pro Gly Lys Gly Leu
            35                  40                  45 gag tgg gtt ggc cgt act aga aac aaa gct aac agt tac acc aca gaa      191
Glu Trp Val Gly Arg Thr Arg Asn Lys Ala Asn Ser Tyr Thr Thr Glu
        50                  55                  60 tac gcc gcg tct gtg aaa ggc aga ttc acc atc tca aga gat gat tca      239
Tyr Ala Ala Ser Val Lys Gly Arg Phe Thr Ile Ser Arg Asp Asp Ser
65                  70                  75 aag aac tca ctg tat ctg caa atg aac agt ctg aga gcc gag gac aca      287
Lys Asn Ser Leu Tyr Leu Gln Met Asn Ser Leu Arg Ala Glu Asp Thr
80                  85                  90                  95 gcc gtg tat tac tgt gcc aaa gac cgc tac gtc aac acg tcg aac gcg      335
Ala Val Tyr Tyr Cys Ala Lys Asp Arg Tyr Val Asn Thr Ser Asn Ala
                100                 105                 110 ttc gat tac tgg ggc cag ggc acc ctg gtg acc gtg ctc gag ggt acc      383
Phe Asp Tyr Trp Gly Gln Gly Thr Leu Val Thr Val Leu Glu Gly Thr
            115                 120                 125 gga ggt tcc ggc gga acc ggg tct ggg act ggt acg agc gag ctc gac      431
Gly Gly Ser Gly Gly Thr Gly Ser Gly Thr Gly Thr Ser Glu Leu Asp
        130                 135                 140 atc cag atg aca cag tct cca gac tca ctg ccc gtc acc cct gga gag      479
Ile Gln Met Thr Gln Ser Pro Asp Ser Leu Pro Val Thr Pro Gly Glu
    145                 150                 155 ccg gcc tcc atc tcc tgc aga tct agt cag agc ctc ctg cat agt aat      527
Pro Ala Ser Ile Ser Cys Arg Ser Ser Gln Ser Leu Leu His Ser Asn
160                 165                 170                 175 gga tac aac tat ttg gat tgg tac ctg cag aag cca ggg cag tct cca      575
Gly Tyr Asn Tyr Leu Asp Trp Tyr Leu Gln Lys Pro Gly Gln Ser Pro
                180                 185                 190 cag ctc ctg atc tat ttg ggt tct aat cgg gcc tcc ggg gtc cct gac      623
Gln Leu Leu Ile Tyr Leu Gly Ser Asn Arg Ala Ser Gly Val Pro Asp
            195                 200                 205 agg ttc agt ggc agt gga tca ggc aca gat ttt aca ctg aaa atc agc      671
Arg Phe Ser Gly Ser Gly Ser Gly Thr Asp Phe Thr Leu Lys Ile Ser
        210                 215                 220 aga gtg gag gct cac cat gtt ggg gtt tat tac tgc cag cag tac ccg      719
Arg Val Glu Ala His His Val Gly Val Tyr Tyr Cys Gln Gln Tyr Pro
    225                 230                 235 ctg ggc ccg ccc acc ttc ggc cag ggc acc aaa ctg gaa atc aaa cgc      767
Leu Gly Pro Pro Thr Phe Gly Gln Gly Thr Lys Leu Glu Ile Lys Arg
240                 245                 250                 255 gcg gcc gc                                                           775
Ala Ala
```

<210> SEQ ID NO 4
<211> LENGTH: 257
<212> TYPE: PRT
<213> ORGANISM: Artificial sequence
<220> FEATURE:
<223> OTHER INFORMATION: scFv SC02009

<400> SEQUENCE: 4

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Gly Tyr Ser Met Asn Trp Val Arg Gln Ala Pro Gly Lys Gly Leu Glu
        35                  40                  45

Trp Val Gly Arg Thr Arg Asn Lys Ala Asn Ser Tyr Thr Thr Glu Tyr
    50                  55                  60

Ala Ala Ser Val Lys Gly Arg Phe Thr Ile Ser Arg Asp Asp Ser Lys
65                  70                  75                  80

Asn Ser Leu Tyr Leu Gln Met Asn Ser Leu Arg Ala Glu Asp Thr Ala
                85                  90                  95

Val Tyr Tyr Cys Ala Lys Asp Arg Tyr Val Asn Thr Ser Asn Ala Phe
            100                 105                 110

Asp Tyr Trp Gly Gln Gly Thr Leu Val Thr Val Leu Glu Gly Thr Gly
        115                 120                 125

Gly Ser Gly Gly Thr Gly Ser Gly Thr Gly Thr Ser Glu Leu Asp Ile
    130                 135                 140

Gln Met Thr Gln Ser Pro Asp Ser Leu Pro Val Thr Pro Gly Glu Pro
145                 150                 155                 160

Ala Ser Ile Ser Cys Arg Ser Ser Gln Ser Leu Leu His Ser Asn Gly
                165                 170                 175

Tyr Asn Tyr Leu Asp Trp Tyr Leu Gln Lys Pro Gly Gln Ser Pro Gln
            180                 185                 190

Leu Leu Ile Tyr Leu Gly Ser Asn Arg Ala Ser Gly Val Pro Asp Arg
        195                 200                 205

Phe Ser Gly Ser Gly Ser Gly Thr Asp Phe Thr Leu Lys Ile Ser Arg
    210                 215                 220

Val Glu Ala His His Val Gly Val Tyr Tyr Cys Gln Gln Tyr Pro Leu
225                 230                 235                 240

Gly Pro Pro Thr Phe Gly Gln Gly Thr Lys Leu Glu Ile Lys Arg Ala
                245                 250                 255

Ala

<210> SEQ ID NO 5
<211> LENGTH: 736
<212> TYPE: DNA
<213> ORGANISM: Artificial sequence
<220> FEATURE:
<223> OTHER INFORMATION: scFv SC02010
<220> FEATURE:
<221> NAME/KEY: CDS
<222> LOCATION: (3)..(734)
<223> OTHER INFORMATION: Source of genetic material is Homo sapiens

<400> SEQUENCE: 5 cc atg gct gag gtg cag ctg gtg gag tct ggg gga ggc ttg atc cag        47
   Met Ala Glu Val Gln Leu Val Glu Ser Gly Gly Gly Leu Ile Gln
   1               5                   10                  15 cct ggg ggg tcc ctg aga ctc tcc tgt gca gcc tct gga ttc acc ttc       95

```
                                    Pro Gly Gly Ser Leu Arg Leu Ser Cys Ala Ala Ser Gly Phe Thr Phe
                                                20                  25                  30 agc ggc tac cct atg aac tgg gtc cgc cag gcg ccc ggg aag ggg ctg         143
Ser Gly Tyr Pro Met Asn Trp Val Arg Gln Ala Pro Gly Lys Gly Leu
        35                  40                  45 gag tgg gtg gca gtt ata tca tat gat gga agt aat aaa tac tac gca         191
Glu Trp Val Ala Val Ile Ser Tyr Asp Gly Ser Asn Lys Tyr Tyr Ala
    50                  55                  60 gac tcc gtg aag ggc cga ttc acc atc tcc aga gac aat tcc aag aac         239
Asp Ser Val Lys Gly Arg Phe Thr Ile Ser Arg Asp Asn Ser Lys Asn
65                  70                  75                  80 acg ctg tat ctg caa atg aac agc ctg aga gct gag gac aca gcc gtg         287
Thr Leu Tyr Leu Gln Met Asn Ser Leu Arg Ala Glu Asp Thr Ala Val
                85                  90                  95 tat tac tgt gca aga gac atg tcc ggc ttc cac gag ttc gat tac tgg         335
Tyr Tyr Cys Ala Arg Asp Met Ser Gly Phe His Glu Phe Asp Tyr Trp
            100                 105                 110 ggc cag ggc acc ctg gtg acc gtg ctc gag ggt acc gga ggt tcc ggc         383
Gly Gln Gly Thr Leu Val Thr Val Leu Glu Gly Thr Gly Gly Ser Gly
        115                 120                 125 gga acc ggg tct ggg act ggt acg agc gag ctc acc cag tct cca tcc         431
Gly Thr Gly Ser Gly Thr Gly Thr Ser Glu Leu Thr Gln Ser Pro Ser
    130                 135                 140 tcc ctg tct gca tct gta gga gac aga gtc acc atc act tgc cgg gca         479
Ser Leu Ser Ala Ser Val Gly Asp Arg Val Thr Ile Thr Cys Arg Ala
145                 150                 155 agt cag agc att agc agc tac tta aat tgg tat cag cag aaa cca ggg         527
Ser Gln Ser Ile Ser Ser Tyr Leu Asn Trp Tyr Gln Gln Lys Pro Gly
160                 165                 170                 175 aaa gcc cct aag ctc ctg atc tat gct gca tcc agt ttg caa agt ggg         575
Lys Ala Pro Lys Leu Leu Ile Tyr Ala Ala Ser Ser Leu Gln Ser Gly
                180                 185                 190 gtc cca tca agg ttc agt ggc agt gga tct ggg aca gat ttc act ctc         623
Val Pro Ser Arg Phe Ser Gly Ser Gly Ser Gly Thr Asp Phe Thr Leu
            195                 200                 205 acc atc agc agt ctg caa cct gaa gat ttt gca act tac tac tgt caa         671
Thr Ile Ser Ser Leu Gln Pro Glu Asp Phe Ala Thr Tyr Tyr Cys Gln
        210                 215                 220 cag agt tac agt acc cct cca acg ttc ggc caa ggg acc aag gtg gag         719
Gln Ser Tyr Ser Thr Pro Pro Thr Phe Gly Gln Gly Thr Lys Val Glu
    225                 230                 235 atc aaa cgt gcg gcc gc                                                  736
Ile Lys Arg Ala Ala
240

<210> SEQ ID NO 6
<211> LENGTH: 244
<212> TYPE: PRT
<213> ORGANISM: Artificial sequence
<220> FEATURE:
<223> OTHER INFORMATION: scFv SC02010

<400> SEQUENCE: 6

Met Ala Glu Val Gln Leu Val Glu Ser Gly Gly Gly Leu Ile Gln Pro
1               5                   10                  15

Gly Gly Ser Leu Arg Leu Ser Cys Ala Ala Ser Gly Phe Thr Phe Ser
            20                  25                  30

Gly Tyr Pro Met Asn Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
```

```
                50                      55                      60
Ser Val Lys Gly Arg Phe Thr Ile Ser Arg Asp Asn Ser Lys Asn Thr
 65                      70                      75                      80

Leu Tyr Leu Gln Met Asn Ser Leu Arg Ala Glu Asp Thr Ala Val Tyr
                         85                      90                      95

Tyr Cys Ala Arg Asp Met Ser Gly Phe His Glu Phe Asp Tyr Trp Gly
                        100                     105                     110

Gln Gly Thr Leu Val Thr Val Leu Glu Gly Thr Gly Gly Ser Gly Gly
                115                     120                     125

Thr Gly Ser Gly Thr Gly Ser Glu Leu Thr Gln Ser Pro Ser Ser
        130                     135                     140

Leu Ser Ala Ser Val Gly Asp Arg Val Thr Ile Thr Cys Arg Ala Ser
145                     150                     155                     160

Gln Ser Ile Ser Ser Tyr Leu Asn Trp Tyr Gln Gln Lys Pro Gly Lys
                165                     170                     175

Ala Pro Lys Leu Leu Ile Tyr Ala Ala Ser Ser Leu Gln Ser Gly Val
                180                     185                     190

Pro Ser Arg Phe Ser Gly Ser Gly Ser Gly Thr Asp Phe Thr Leu Thr
                195                     200                     205

Ile Ser Ser Leu Gln Pro Glu Asp Phe Ala Thr Tyr Tyr Cys Gln Gln
210                     215                     220

Ser Tyr Ser Thr Pro Pro Thr Phe Gly Gln Gly Thr Lys Val Glu Ile
225                     230                     235                     240

Lys Arg Ala Ala

<210> SEQ ID NO 7
<211> LENGTH: 763
<212> TYPE: DNA
<213> ORGANISM: Artificial sequence
<220> FEATURE:
<223> OTHER INFORMATION: scFv SC02011
<220> FEATURE:
<221> NAME/KEY: CDS
<222> LOCATION: (3)..(761)
<223> OTHER INFORMATION: Source of genetic material is Homo sapiens

<400> SEQUENCE: 7 cc atg gct gag gtg cag ctg gtg gag tct ggg gga ggc gtg gtc cag      47
   Met Ala Glu Val Gln Leu Val Glu Ser Gly Gly Gly Val Val Gln
     1               5                  10                  15 cct ggg agg tcc ctg aga ctc tcc tgt gca gcc tct gga ttc acc ttc     95
Pro Gly Arg Ser Leu Arg Leu Ser Cys Ala Ala Ser Gly Phe Thr Phe
                 20                  25                  30 agc gac tac acg atg aac tgg gtc cgc cag gcg ccc ggg aag ggg ctg    143
Ser Asp Tyr Thr Met Asn Trp Val Arg Gln Ala Pro Gly Lys Gly Leu
             35                  40                  45 gag tgg gtc tca tcc att agt ggt ggt agc aca tac tac gca gac tcc    191
Glu Trp Val Ser Ser Ile Ser Gly Gly Ser Thr Tyr Tyr Ala Asp Ser
         50                  55                  60 agg aag ggc aga ttc acc atc tcc aga gac aat tcc aag aac acg ctg    239
Arg Lys Gly Arg Phe Thr Ile Ser Arg Asp Asn Ser Lys Asn Thr Leu
 65                  70                  75 tat ctt caa atg aac aac ctg aga gct gag gac acg gcc gtg tat tac    287
Tyr Leu Gln Met Asn Asn Leu Arg Ala Glu Asp Thr Ala Val Tyr Tyr
 80                  85                  90                  95 tgt gca aga gac cgc tac ttc agg cag cag aac gcg ttc gat tac tgg    335
Cys Ala Arg Asp Arg Tyr Phe Arg Gln Gln Asn Ala Phe Asp Tyr Trp
                100                 105                 110
```

```
ggc cag ggc acc ctg gtg acc gtg ctc gag ggt acc gga ggt tcc ggc        383
Gly Gln Gly Thr Leu Val Thr Val Leu Glu Gly Thr Gly Gly Ser Gly
            115                 120                 125 gga acc ggg tct ggg act ggt acg agc gag ctc gac atc cag atg act        431
Gly Thr Gly Ser Gly Thr Gly Thr Ser Glu Leu Asp Ile Gln Met Thr
        130                 135                 140 cag tct cca gtc acc ctg ccc gtc acc cct gga gag ccg gcc tcc atc        479
Gln Ser Pro Val Thr Leu Pro Val Thr Pro Gly Glu Pro Ala Ser Ile
    145                 150                 155 tcc tgc agg tct agt cag agc ctc ctg cat agt aat gga tac aac tat        527
Ser Cys Arg Ser Ser Gln Ser Leu Leu His Ser Asn Gly Tyr Asn Tyr
160                 165                 170                 175 ttg gat tgg tac ctg cag aag cca ggg cag tct cca cag ctc ctg atc        575
Leu Asp Trp Tyr Leu Gln Lys Pro Gly Gln Ser Pro Gln Leu Leu Ile
            180                 185                 190 tat ttg ggt tct aat cgg gcc tcc ggg gtc cct gac agg ttc agt ggc        623
Tyr Leu Gly Ser Asn Arg Ala Ser Gly Val Pro Asp Arg Phe Ser Gly
        195                 200                 205 agt gga tca ggc aca gat ttt aca ctg aaa atc agc aga gtg gag gct        671
Ser Gly Ser Gly Thr Asp Phe Thr Leu Lys Ile Ser Arg Val Glu Ala
    210                 215                 220 gag gat gtt ggg gtt tat tac tgc cag cag tac ctc acg gcc ccg ccc        719
Glu Asp Val Gly Val Tyr Tyr Cys Gln Gln Tyr Leu Thr Ala Pro Pro
225                 230                 235 acc ttc ggc cag ggc acc aaa ctg gaa atc aaa cgc gcg gcc gc            763
Thr Phe Gly Gln Gly Thr Lys Leu Glu Ile Lys Arg Ala Ala
240                 245                 250

<210> SEQ ID NO 8
<211> LENGTH: 253
<212> TYPE: PRT
<213> ORGANISM: Artificial sequence
<220> FEATURE:
<223> OTHER INFORMATION: scFv SC02011

<400> SEQUENCE: 8

Met Ala Glu Val Gln Leu Val Glu Ser Gly Gly Gly Val Val Gln Pro
1               5                   10                  15

Gly Arg Ser Leu Arg Leu Ser Cys Ala Ala Ser Gly Phe Thr Phe Ser
            20                  25                  30

Asp Tyr Thr Met Asn Trp Val Arg Gln Ala Pro Gly Lys Gly Leu Glu
        35                  40                  45

Trp Val Ser Ser Ile Ser Gly Gly Ser Thr Tyr Tyr Ala Asp Ser Arg
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
            85                  90                  95

Ala Arg Asp Arg Tyr Phe Arg Gln Gln Asn Ala Phe Asp Tyr Trp Gly
        100                 105                 110

Gln Gly Thr Leu Val Thr Val Leu Glu Gly Thr Gly Gly Ser Gly Gly
    115                 120                 125

Thr Gly Ser Gly Thr Gly Thr Ser Glu Leu Asp Ile Gln Met Thr Gln
130                 135                 140

Ser Pro Val Thr Leu Pro Val Thr Pro Gly Glu Pro Ala Ser Ile Ser
145                 150                 155                 160

Cys Arg Ser Ser Gln Ser Leu Leu His Ser Asn Gly Tyr Asn Tyr Leu
            165                 170                 175
```

```
Asp Trp Tyr Leu Gln Lys Pro Gly Gln Ser Pro Gln Leu Leu Ile Tyr
            180                 185                 190

Leu Gly Ser Asn Arg Ala Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Gln Gln Tyr Leu Thr Ala Pro Pro Thr
225                 230                 235                 240

Phe Gly Gln Gly Thr Lys Leu Glu Ile Lys Arg Ala Ala
                245                 250

<210> SEQ ID NO 9
<211> LENGTH: 748
<212> TYPE: DNA
<213> ORGANISM: Artificial sequence
<220> FEATURE:
<223> OTHER INFORMATION: scFv SC02012
<220> FEATURE:
<221> NAME/KEY: CDS
<222> LOCATION: (3)..(746)
<223> OTHER INFORMATION: Source of genetic material is Homo sapiens

<400> SEQUENCE: 9 cc atg gct gaa gtg cag ctg gtg gaa agc ggc ggc ggc ctg gtg aag      47
   Met Ala Glu Val Gln Leu Val Glu Ser Gly Gly Gly Leu Val Lys
   1               5                   10                  15 ccg ggt ggc agc ctg cgc ctg agc tgc gcc gct agc ggc ttc acc ttt    95
Pro Gly Gly Ser Leu Arg Leu Ser Cys Ala Ala Ser Gly Phe Thr Phe
            20                  25                  30 agc aac gac tcg atg aac tgg atg cgc cag gcc ccg ggc aaa ggc ctc    143
Ser Asn Asp Ser Met Asn Trp Met Arg Gln Ala Pro Gly Lys Gly Leu
        35                  40                  45 gaa tgg gtg gcc aat atc aat cag gat ggc aac gaa aaa tat tac gcc    191
Glu Trp Val Ala Asn Ile Asn Gln Asp Gly Asn Glu Lys Tyr Tyr Ala
    50                  55                  60 gac tct gtc aaa ggc cgc ttc acc atc agt cgc gat aac tcc aaa aac    239
Asp Ser Val Lys Gly Arg Phe Thr Ile Ser Arg Asp Asn Ser Lys Asn
65                  70                  75 tcc ctg tac ctg cag atg aac agc ctg cgc gac gaa gat acc gcc ctg    287
Ser Leu Tyr Leu Gln Met Asn Ser Leu Arg Asp Glu Asp Thr Ala Leu
80                  85                  90                  95 tac tac tgc gca cgc gcc cgc gcc gcc ggc acc atc ttc gat tac tgg    335
Tyr Tyr Cys Ala Arg Ala Arg Ala Ala Gly Thr Ile Phe Asp Tyr Trp
                100                 105                 110 ggc cag ggc acc ctg gtg acc gtg ctc gag ggt acc gga ggt tcc ggc    383
Gly Gln Gly Thr Leu Val Thr Val Leu Glu Gly Thr Gly Gly Ser Gly
            115                 120                 125 gga acc ggg tct ggg act ggt acg agc gag ctc gat atc cag atg acc    431
Gly Thr Gly Ser Gly Thr Gly Thr Ser Glu Leu Asp Ile Gln Met Thr
        130                 135                 140 cag agc ccg agt tcc ctg agc gcc tcc gtg ggc gac cgc gtg acc atc    479
Gln Ser Pro Ser Ser Leu Ser Ala Ser Val Gly Asp Arg Val Thr Ile
145                 150                 155 acc tgc cgc gcc agc cag aac gtc agc aac tac ctg acc tgg tac cag    527
Thr Cys Arg Ala Ser Gln Asn Val Ser Asn Tyr Leu Thr Trp Tyr Gln
160                 165                 170                 175 cag aaa ccg ggc aag gct gga aaa ctg ctg att tac gcc gcc agc agc    575
Gln Lys Pro Gly Lys Ala Gly Lys Leu Leu Ile Tyr Ala Ala Ser Ser
            180                 185                 190 ctc caa agc ggc gtg ccg tct aga ttc agt ggc tcc ggc tcc gga acc    623
Leu Gln Ser Gly Val Pro Ser Arg Phe Ser Gly Ser Gly Ser Gly Thr
```

```
                          195                 200                 205
gat ttt acc ctg acc atc agc agc ctg cag ccg gaa gat ttc gct acc        671
Asp Phe Thr Leu Thr Ile Ser Ser Leu Gln Pro Glu Asp Phe Ala Thr
        210                 215                 220 tac tat tgt cag cag tcc tac ttc aac ccg gcg acc ttc ggc cag ggc        719
Tyr Tyr Cys Gln Gln Ser Tyr Phe Asn Pro Ala Thr Phe Gly Gln Gly
    225                 230                 235 acc aaa ctg gaa atc aaa cgc gcg gcc gc                                 748
Thr Lys Leu Glu Ile Lys Arg Ala Ala
240                 245

<210> SEQ ID NO 10
<211> LENGTH: 248
<212> TYPE: PRT
<213> ORGANISM: Artificial sequence
<220> FEATURE:
<223> OTHER INFORMATION: scFv SC02012

<400> SEQUENCE: 10

Met Ala Glu Val Gln Leu Val Glu Ser Gly Gly Gly Leu Val Lys Pro
1               5                   10                  15

Gly Gly Ser Leu Arg Leu Ser Cys Ala Ala Ser Gly Phe Thr Phe Ser
            20                  25                  30

Asn Asp Ser Met Asn Trp Met Arg Gln Ala Pro Gly Lys Gly Leu Glu
        35                  40                  45

Trp Val Ala Asn Ile Asn Gln Asp Gly Asn Glu Lys Tyr Tyr Ala Asp
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Asp Glu Asp Thr Ala Leu Tyr
                85                  90                  95

Tyr Cys Ala Arg Ala Arg Ala Ala Gly Thr Ile Phe Asp Tyr Trp Gly
            100                 105                 110

Gln Gly Thr Leu Val Thr Val Leu Glu Gly Thr Gly Gly Ser Gly Gly
        115                 120                 125

Thr Gly Ser Gly Thr Gly Thr Ser Glu Leu Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Asn Val Ser Asn Tyr Leu Thr Trp Tyr Gln Gln
                165                 170                 175

Lys Pro Gly Lys Ala Gly Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ser Tyr Phe Asn Pro Ala Thr Phe Gly Gln Gly Thr
225                 230                 235                 240

Lys Leu Glu Ile Lys Arg Ala Ala
                245

<210> SEQ ID NO 11
<211> LENGTH: 769
<212> TYPE: DNA
<213> ORGANISM: Artificial sequence
<220> FEATURE:
<223> OTHER INFORMATION: scFv SC02021
```

<220> FEATURE:
<221> NAME/KEY: CDS
<222> LOCATION: (3)..(767)
<223> OTHER INFORMATION: Source of genetic material is Homo sapiens

<400> SEQUENCE: 11

```
cc atg gct gag gtg cag ctg gtg gag tct ggg gga ggc ttg gta cag         47
   Met Ala Glu Val Gln Leu Val Glu Ser Gly Gly Gly Leu Val Gln
   1               5                  10                  15 cct agg ggg tcc ctg aga ctc tcc tgt gca gcc tct gga ttc acc ttt         95
Pro Arg Gly Ser Leu Arg Leu Ser Cys Ala Ala Ser Gly Phe Thr Phe
                20                  25                  30 agc agc tac gcg atg aac tgg gtc cgc cag gcg ccc ggg aag ggg ctg        143
Ser Ser Tyr Ala Met Asn Trp Val Arg Gln Ala Pro Gly Lys Gly Leu
            35                  40                  45 gag tgg gtg gca gtt ata tca tat gat gga agc aat aaa tac tac gca        191
Glu Trp Val Ala Val Ile Ser Tyr Asp Gly Ser Asn Lys Tyr Tyr Ala
        50                  55                  60 gac tcc gtg aag ggc cga ttc acc atc tcc aga gac aat tcc aag aac        239
Asp Ser Val Lys Gly Arg Phe Thr Ile Ser Arg Asp Asn Ser Lys Asn
    65                  70                  75 acg ctg tat ctg caa atg aac agc ctg aga gct gag gac aca gcc gtg        287
Thr Leu Tyr Leu Gln Met Asn Ser Leu Arg Ala Glu Asp Thr Ala Val
80                  85                  90                  95 tat tac tgt gcc aaa gac cgc tac atc acg ttg ccg aac gcg ttg gat        335
Tyr Tyr Cys Ala Lys Asp Arg Tyr Ile Thr Leu Pro Asn Ala Leu Asp
                100                 105                 110 tac tgg ggc cag ggc acc ctg gtg acc gtg ctc gag ggt acc gga ggt        383
Tyr Trp Gly Gln Gly Thr Leu Val Thr Val Leu Glu Gly Thr Gly Gly
            115                 120                 125 tcc ggc gga acc ggg tct ggg act ggt acg agc gag ctc gac atc cag        431
Ser Gly Gly Thr Gly Ser Gly Thr Gly Thr Ser Glu Leu Asp Ile Gln
        130                 135                 140 atg acc cag tct cca gtc tca ctg ccc gtc acc cct gga gag ccg gcc        479
Met Thr Gln Ser Pro Val Ser Leu Pro Val Thr Pro Gly Glu Pro Ala
    145                 150                 155 tcc atc tcc tgc agg tct agt cag agc ctc ctg cat agt aat gga tac        527
Ser Ile Ser Cys Arg Ser Ser Gln Ser Leu Leu His Ser Asn Gly Tyr
160                 165                 170                 175 aac tat ttg gat tgg tac ctg cag aag cca ggg cag tct cca cag ctc        575
Asn Tyr Leu Asp Trp Tyr Leu Gln Lys Pro Gly Gln Ser Pro Gln Leu
                180                 185                 190 ctg atc tat ttg ggt tct aat cgg gcc tcc ggg gtc cct gac agg ttc        623
Leu Ile Tyr Leu Gly Ser Asn Arg Ala Ser Gly Val Pro Asp Arg Phe
            195                 200                 205 agt ggc agt gga tca ggc aca gat ttt aca ctg aaa atc agc aga gtg        671
Ser Gly Ser Gly Ser Gly Thr Asp Phe Thr Leu Lys Ile Ser Arg Val
        210                 215                 220 gag gct gag gat gtt ggg gtt tat tac tgc cag cag tac aag tcg aac        719
Glu Ala Glu Asp Val Gly Val Tyr Tyr Cys Gln Gln Tyr Lys Ser Asn
    225                 230                 235 ccg ccc acc ttc ggc cag ggc acc aaa gtg gaa atc aaa cgc gcg gcc        767
Pro Pro Thr Phe Gly Gln Gly Thr Lys Val Glu Ile Lys Arg Ala Ala
240                 245                 250                 255 gc                                                                     769
```

<210> SEQ ID NO 12
<211> LENGTH: 255
<212> TYPE: PRT
<213> ORGANISM: Artificial sequence
<220> FEATURE:

<223> OTHER INFORMATION: scFv SC02021

<400> SEQUENCE: 12

```
Met Ala Glu Val Gln Leu Val Glu Ser Gly Gly Gly Leu Val Gln Pro
1               5                   10                  15

Arg Gly Ser Leu Arg Leu Ser Cys Ala Ala Ser Gly Phe Thr Phe Ser
            20                  25                  30

Ser Tyr Ala Met Asn Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Arg Tyr Ile Thr Leu Pro Asn Ala Leu Asp Tyr
            100                 105                 110

Trp Gly Gln Gly Thr Leu Val Thr Val Leu Glu Gly Thr Gly Gly Ser
        115                 120                 125

Gly Gly Thr Gly Ser Gly Thr Gly Thr Ser Glu Leu Asp Ile Gln Met
    130                 135                 140

Thr Gln Ser Pro Val Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Gly Thr Asp Phe Thr Leu Lys Ile Ser Arg Val Glu
    210                 215                 220

Ala Glu Asp Val Gly Val Tyr Tyr Cys Gln Gln Tyr Lys Ser Asn Pro
225                 230                 235                 240

Pro Thr Phe Gly Gln Gly Thr Lys Val Glu Ile Lys Arg Ala Ala
                245                 250                 255
```

<210> SEQ ID NO 13
<211> LENGTH: 745
<212> TYPE: DNA
<213> ORGANISM: Artificial sequence
<220> FEATURE:
<223> OTHER INFORMATION: scFv SC02022
<220> FEATURE:
<221> NAME/KEY: CDS
<222> LOCATION: (3)..(743)
<223> OTHER INFORMATION: Source of genetic material is Homo sapiens

<400> SEQUENCE: 13

```
cc atg gcc gag gtg cag ctg gtg gag tct ggg gga ggc ttg gta cat        47
   Met Ala Glu Val Gln Leu Val Glu Ser Gly Gly Gly Leu Val His
   1               5                   10                  15 cct ggg ggg tcc ctg aga ctc tcc tgt gca ggc tct gga ttc acc ttc        95
Pro Gly Gly Ser Leu Arg Leu Ser Cys Ala Gly Ser Gly Phe Thr Phe
            20                  25                  30 agt agc tat gct atg cac tgg gtt cgc cag gct cca gga aaa ggt ctg      143
Ser Ser Tyr Ala Met His Trp Val Arg Gln Ala Pro Gly Lys Gly Leu
        35                  40                  45 gag tgg gta tca gct att ggt acc ggt ggt ggc aca tac tat gca gac      191
```

```
Glu Trp Val Ser Ala Ile Gly Thr Gly Gly Thr Tyr Tyr Ala Asp
        50                  55                  60 tcc gtg cag ggc cga ttc acc atc tcc aga gac aat gcc aag aac tcc    239
Ser Val Gln Gly Arg Phe Thr Ile Ser Arg Asp Asn Ala Lys Asn Ser
65                  70                  75 ttg tat ctt caa atg aac agc ctg aga gcc gag gac acg gcc gtg tat    287
Leu Tyr Leu Gln Met Asn Ser Leu Arg Ala Glu Asp Thr Ala Val Tyr
80                  85                  90                  95 tac tgt gca aga tac gac gag ccg ctg acg att tac tgg ttt gac tcc    335
Tyr Cys Ala Arg Tyr Asp Glu Pro Leu Thr Ile Tyr Trp Phe Asp Ser
            100                 105                 110 tgg ggc caa ggt acc ctg gtc acc gtc tcg agt ggt gga ggc ggt tca    383
Trp Gly Gln Gly Thr Leu Val Thr Val Ser Ser Gly Gly Gly Gly Ser
        115                 120                 125 ggc gga ggt ggc tct ggc ggt ggc gga tcg gaa att gag ctc aca cag    431
Gly Gly Gly Gly Ser Gly Gly Gly Gly Ser Glu Ile Glu Leu Thr Gln
        130                 135                 140 tct cca gcc acc ctg tct ttg tct cca ggg gaa aga gcc acc ctc tcc    479
Ser Pro Ala Thr Leu Ser Leu Ser Pro Gly Glu Arg Ala Thr Leu Ser
145                 150                 155 tgc agg gcc agt cag agt gtt agc agc tac tta gcc tgg tac caa cag    527
Cys Arg Ala Ser Gln Ser Val Ser Ser Tyr Leu Ala Trp Tyr Gln Gln
160                 165                 170                 175 aaa cct ggc cag gct ccc agg ctc ctc atc tat gat gca tcc aac agg    575
Lys Pro Gly Gln Ala Pro Arg Leu Leu Ile Tyr Asp Ala Ser Asn Arg
            180                 185                 190 gcc act ggc atc cca gcc agg ttc agt ggc agt ggg tct ggg aca gac    623
Ala Thr Gly Ile Pro Ala Arg Phe Ser Gly Ser Gly Ser Gly Thr Asp
        195                 200                 205 ttc act ctc acc atc agc agc cta gag cct gaa gat ttt gca gtt tat    671
Phe Thr Leu Thr Ile Ser Ser Leu Glu Pro Glu Asp Phe Ala Val Tyr
        210                 215                 220 tac tgt cag cag cgt agc aac tgg cct ccg gct ttc ggc gga ggg acc    719
Tyr Cys Gln Gln Arg Ser Asn Trp Pro Pro Ala Phe Gly Gly Gly Thr
        225                 230                 235 aag gtg gag atc aaa cgt gcg gcc gc                                 745
Lys Val Glu Ile Lys Arg Ala Ala
240                 245

<210> SEQ ID NO 14
<211> LENGTH: 247
<212> TYPE: PRT
<213> ORGANISM: Artificial sequence
<220> FEATURE:
<223> OTHER INFORMATION: scFv SC02022

<400> SEQUENCE: 14

Met Ala Glu Val Gln Leu Val Glu Ser Gly Gly Gly Leu Val His Pro
1               5                   10                  15

Gly Gly Ser Leu Arg Leu Ser Cys Ala Gly Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ser Ala Ile Gly Thr Gly Gly Thr Tyr Tyr Ala Asp Ser
        50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95
```

```
Cys Ala Arg Tyr Asp Glu Pro Leu Thr Ile Tyr Trp Phe Asp Ser Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Glu Ile Glu Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gln Gln Arg Ser Asn Trp Pro Pro Ala Phe Gly Gly Gly Thr Lys
225                 230                 235                 240

Val Glu Ile Lys Arg Ala Ala
                245

<210> SEQ ID NO 15
<211> LENGTH: 745
<212> TYPE: DNA
<213> ORGANISM: Artificial sequence
<220> FEATURE:
<223> OTHER INFORMATION: scFv SC02023
<220> FEATURE:
<221> NAME/KEY: CDS
<222> LOCATION: (3)..(743)
<223> OTHER INFORMATION: Source of genetic material is Homo sapiens

<400> SEQUENCE: 15 cc atg gcc gag gtg cag ctg gtg gag tct ggg gga ggc ttg gta cat        47
   Met Ala Glu Val Gln Leu Val Glu Ser Gly Gly Gly Leu Val His
   1               5                   10                  15 cct ggg ggg tcc ctg aga ctc tcc tgt gca ggc tct gga ttc acc ttc       95
Pro Gly Gly Ser Leu Arg Leu Ser Cys Ala Gly Ser Gly Phe Thr Phe
            20                  25                  30 agt agc tat gct atg cac tgg gtt cgc cag gct cca gga aaa ggt ctg      143
Ser Ser Tyr Ala Met His Trp Val Arg Gln Ala Pro Gly Lys Gly Leu
        35                  40                  45 gag tgg gta tca gct att ggt act ggt ggt ggc aca tac tat gca gac      191
Glu Trp Val Ser Ala Ile Gly Thr Gly Gly Gly Thr Tyr Tyr Ala Asp
    50                  55                  60 tcc gtg atg ggc cgg ttc acc atc tcc aga gac aat tcc aag aac acg      239
Ser Val Met Gly Arg Phe Thr Ile Ser Arg Asp Asn Ser Lys Asn Thr
65                  70                  75 ctg tat ctg caa atg aac agc ctg aga gcc gag gac acg gcc gtg tat      287
Leu Tyr Leu Gln Met Asn Ser Leu Arg Ala Glu Asp Thr Ala Val Tyr
80                  85                  90                  95 tac tgt gca aga tac gac aat gtg atg ggt ctt tac tgg ttt gac tac      335
Tyr Cys Ala Arg Tyr Asp Asn Val Met Gly Leu Tyr Trp Phe Asp Tyr
                100                 105                 110 tgg ggc caa ggt acc ctg gtc acc gtc tcg agt ggt gga ggc ggt tca      383
Trp Gly Gln Gly Thr Leu Val Thr Val Ser Ser Gly Gly Gly Gly Ser
            115                 120                 125 ggc gga ggt ggc tct ggc ggt ggc gga tcg gaa att gag ctc aca cag      431
Gly Gly Gly Gly Ser Gly Gly Gly Gly Ser Glu Ile Glu Leu Thr Gln
        130                 135                 140
```

```
tct cca gcc acc ctg tct ttg tct cca ggg gaa aga gcc acc ctc tcc        479
Ser Pro Ala Thr Leu Ser Leu Ser Pro Gly Glu Arg Ala Thr Leu Ser
    145                 150                 155 tgc agg gcc agt cag agt gtt agc agc tac tta gcc tgg tac caa cag        527
Cys Arg Ala Ser Gln Ser Val Ser Ser Tyr Leu Ala Trp Tyr Gln Gln
160                 165                 170                 175 aaa cct ggc cag gct ccc agg ctc ctc atc tat gat gca tcc aac agg        575
Lys Pro Gly Gln Ala Pro Arg Leu Leu Ile Tyr Asp Ala Ser Asn Arg
                180                 185                 190 gcc act ggc atc cca gcc agg ttc agt ggc agt ggg tct ggg aca gac        623
Ala Thr Gly Ile Pro Ala Arg Phe Ser Gly Ser Gly Ser Gly Thr Asp
            195                 200                 205 ttc act ctc acc atc agc agc cta gag cct gaa gat ttt gca gtt tat        671
Phe Thr Leu Thr Ile Ser Ser Leu Glu Pro Glu Asp Phe Ala Val Tyr
        210                 215                 220 tac tgt cag cag cgt agc aac tgg cct ccg gct ttc ggc gga ggg acc        719
Tyr Cys Gln Gln Arg Ser Asn Trp Pro Pro Ala Phe Gly Gly Gly Thr
    225                 230                 235 aag gtg gag atc aaa cgt gcg gcc gc                                     745
Lys Val Glu Ile Lys Arg Ala Ala
240                 245
```

<210> SEQ ID NO 16
<211> LENGTH: 247
<212> TYPE: PRT
<213> ORGANISM: Artificial sequence
<220> FEATURE:
<223> OTHER INFORMATION: scFv SC02023

<400> SEQUENCE: 16

```
Met Ala Glu Val Gln Leu Val Glu Ser Gly Gly Gly Leu Val His Pro
1               5                   10                  15

Gly Gly Ser Leu Arg Leu Ser Cys Ala Gly Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ser Ala Ile Gly Thr Gly Gly Thr Tyr Tyr Ala Asp Ser
    50                  55                  60

Val Met Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Tyr Asp Asn Val Met Gly Leu Tyr Trp Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Glu Ile Glu Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Ser Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
```

```
                210                 215                 220
Cys Gln Gln Arg Ser Asn Trp Pro Pro Ala Phe Gly Gly Gly Thr Lys
225                 230                 235                 240

Val Glu Ile Lys Arg Ala Ala
            245

<210> SEQ ID NO 17
<211> LENGTH: 12
<212> TYPE: PRT
<213> ORGANISM: Artificial sequence
<220> FEATURE:
<223> OTHER INFORMATION: CDR3 of scFv SC02008

<400> SEQUENCE: 17

Asp Arg Tyr Ser Gln Val His Tyr Ala Leu Asp Tyr
1               5                   10

<210> SEQ ID NO 18
<211> LENGTH: 12
<212> TYPE: PRT
<213> ORGANISM: Artificial sequence
<220> FEATURE:
<223> OTHER INFORMATION: CDR3 of scFv SC02009

<400> SEQUENCE: 18

Asp Arg Tyr Val Asn Thr Ser Asn Ala Phe Asp Tyr
1               5                   10

<210> SEQ ID NO 19
<211> LENGTH: 10
<212> TYPE: PRT
<213> ORGANISM: Artificial sequence
<220> FEATURE:
<223> OTHER INFORMATION: CDR3 of scFv SC02010

<400> SEQUENCE: 19

Asp Met Ser Gly Phe His Glu Phe Asp Tyr
1               5                   10

<210> SEQ ID NO 20
<211> LENGTH: 12
<212> TYPE: PRT
<213> ORGANISM: Artificial sequence
<220> FEATURE:
<223> OTHER INFORMATION: CDR3 of scFv SC02011

<400> SEQUENCE: 20

Asp Arg Tyr Phe Arg Gln Gln Asn Ala Phe Asp Tyr
1               5                   10

<210> SEQ ID NO 21
<211> LENGTH: 10
<212> TYPE: PRT
<213> ORGANISM: Artificial sequence
<220> FEATURE:
<223> OTHER INFORMATION: CDR3 of scFv SC02012

<400> SEQUENCE: 21

Ala Arg Ala Ala Gly Thr Ile Phe Asp Tyr
1               5                   10

<210> SEQ ID NO 22
<211> LENGTH: 12
<212> TYPE: PRT
<213> ORGANISM: Artificial sequence
<220> FEATURE:
```

-continued

<223> OTHER INFORMATION: CDR3 of scFv SC02021

<400> SEQUENCE: 22

Asp Arg Tyr Ile Thr Leu Pro Asn Ala Leu Asp Tyr
1               5                   10

<210> SEQ ID NO 23
<211> LENGTH: 12
<212> TYPE: PRT
<213> ORGANISM: Artificial sequence
<220> FEATURE:
<223> OTHER INFORMATION: CDR3 of scFv SC02022

<400> SEQUENCE: 23

Tyr Asp Glu Pro Leu Thr Ile Tyr Trp Phe Asp Ser
1               5                   10

<210> SEQ ID NO 24
<211> LENGTH: 12
<212> TYPE: PRT
<213> ORGANISM: Artificial sequence
<220> FEATURE:
<223> OTHER INFORMATION: CDR3 of scFv SC02023

<400> SEQUENCE: 24

Tyr Asp Asn Val Met Gly Leu Tyr Trp Phe Asp Tyr
1               5                   10

<210> SEQ ID NO 25
<211> LENGTH: 451
<212> TYPE: PRT
<213> ORGANISM: Artificial sequence
<220> FEATURE:
<223> OTHER INFORMATION: Amino acid sequence of heavy chain of 008

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 26
<211> LENGTH: 449
<212> TYPE: PRT
<213> ORGANISM: Artificial sequence
<220> FEATURE:
<223> OTHER INFORMATION: Amino acid sequence of heavy chain of 011

<400> SEQUENCE: 26

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
                20                  25                  30

Thr Met Asn Trp Val Arg Gln Ala Pro Gly Lys Gly Leu Glu Trp Val
            35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Asp Thr Ala Val Tyr Tyr Cys Ala Arg
                85                  90                  95
```

Asp Arg Tyr Phe Arg Gln Gln Asn Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 27
<211> LENGTH: 451
<212> TYPE: PRT
<213> ORGANISM: Artificial sequence
<220> FEATURE:
<223> OTHER INFORMATION: Amino acid sequence of heavy chain 021

<400> SEQUENCE: 27

Glu Val Gln Leu Val Glu Ser Gly Gly Gly Leu Val Gln Pro Arg Gly

-continued

```
1               5                   10                  15
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
        435                 440                 445

Pro Gly Lys
    450

<210> SEQ ID NO 28
<211> LENGTH: 450
<212> TYPE: PRT
<213> ORGANISM: Artificial sequence
<220> FEATURE:
<223> OTHER INFORMATION: Amino acid sequence of heavy chain of 023

<400> SEQUENCE: 28

Glu Val Gln Leu Val Glu Ser Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 29
<211> LENGTH: 219
<212> TYPE: PRT
<213> ORGANISM: Artificial sequence
<220> FEATURE:
<223> OTHER INFORMATION: Amino acid sequence of light chain of 008

<400> SEQUENCE: 29

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 30
```

<211> LENGTH: 219
<212> TYPE: PRT
<213> ORGANISM: Artificial sequence
<220> FEATURE:
<223> OTHER INFORMATION: Amino acid sequence of light chain of 011

<400> SEQUENCE: 30

```
Asp Ile Val Met Thr Gln Ser Pro Asp Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 31
<211> LENGTH: 219
<212> TYPE: PRT
<213> ORGANISM: Artificial sequence
<220> FEATURE:
<223> OTHER INFORMATION: Amino acid sequence of light chain of 021

<400> SEQUENCE: 31

```
Asp Ile Gln Met Thr Gln Ser Pro Val Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys Val Glu Ile Lys
```

```
                100                 105                 110
Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
            130                 135             140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 32
<211> LENGTH: 214
<212> TYPE: PRT
<213> ORGANISM: Artificial sequence
<220> FEATURE:
<223> OTHER INFORMATION: Amino acid sequence of light chain of 023

<400> SEQUENCE: 32

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135             140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 33
<211> LENGTH: 55
<212> TYPE: DNA

<213> ORGANISM: Artificial sequence
<220> FEATURE:
<223> OTHER INFORMATION: 5' cloning site of pPicZalphaB
<220> FEATURE:
<221> NAME/KEY: CDS
<222> LOCATION: (1)..(54)
<223> OTHER INFORMATION: PCR primer

<400> SEQUENCE: 33

```
tct ctc gag aaa aga gag gct gaa gct gca gga att cac gtg gcc cag      48
Ser Leu Glu Lys Arg Glu Ala Glu Ala Ala Gly Ile His Val Ala Gln
1               5                   10                  15 ccg gcc g                                                            55
Pro Ala
```

<210> SEQ ID NO 34
<211> LENGTH: 18
<212> TYPE: PRT
<213> ORGANISM: Artificial sequence
<220> FEATURE:
<223> OTHER INFORMATION: 5' cloning site of pPicZalphaB

<400> SEQUENCE: 34

```
Ser Leu Glu Lys Arg Glu Ala Glu Ala Ala Gly Ile His Val Ala Gln
1               5                   10                  15

Pro Ala
```

<210> SEQ ID NO 35
<211> LENGTH: 55
<212> TYPE: DNA
<213> ORGANISM: Artificial sequence
<220> FEATURE:
<223> OTHER INFORMATION: 5' cloning site of pPicZFVH
<220> FEATURE:
<221> NAME/KEY: CDS
<222> LOCATION: (1)..(54)
<223> OTHER INFORMATION: PCR primer

<400> SEQUENCE: 35

```
tct ctc gag aaa aga gcc atg gaa gct gca gga att cac gtg gcc cag      48
Ser Leu Glu Lys Arg Ala Met Glu Ala Ala Gly Ile His Val Ala Gln
1               5                   10                  15 ccg gcc g                                                            55
Pro Ala
```

<210> SEQ ID NO 36
<211> LENGTH: 18
<212> TYPE: PRT
<213> ORGANISM: Artificial sequence
<220> FEATURE:
<223> OTHER INFORMATION: 5' cloning site of pPicZFVH

<400> SEQUENCE: 36

```
Ser Leu Glu Lys Arg Ala Met Glu Ala Ala Gly Ile His Val Ala Gln
1               5                   10                  15

Pro Ala
```

<210> SEQ ID NO 37
<211> LENGTH: 92
<212> TYPE: DNA
<213> ORGANISM: Artificial sequence
<220> FEATURE:
<223> OTHER INFORMATION: Synthetic hinge region
<220> FEATURE:
<221> NAME/KEY: CDS
<222> LOCATION: (1)..(90)
<223> OTHER INFORMATION: PCR primer

<400> SEQUENCE: 37

```
gcg gcc gcg cca aag cca agt acc cca cca ggt tct tca tgt cca cca        48
Ala Ala Ala Pro Lys Pro Ser Thr Pro Pro Gly Ser Ser Cys Pro Pro
1               5                   10                  15 tgt cca ggc tct ggc ggt gcg cca atc gat agc ggc ttt cta ga             92
Cys Pro Gly Ser Gly Gly Ala Pro Ile Asp Ser Gly Phe Leu
                20                  25                  30
```

<210> SEQ ID NO 38
<211> LENGTH: 30
<212> TYPE: PRT
<213> ORGANISM: Artificial sequence
<220> FEATURE:
<223> OTHER INFORMATION: Synthetic hinge region

<400> SEQUENCE: 38

```
Ala Ala Ala Pro Lys Pro Ser Thr Pro Pro Gly Ser Ser Cys Pro Pro
1               5                   10                  15

Cys Pro Gly Ser Gly Gly Ala Pro Ile Asp Ser Gly Phe Leu
                20                  25                  30
```

<210> SEQ ID NO 39
<211> LENGTH: 1416
<212> TYPE: DNA
<213> ORGANISM: Artificial sequence
<220> FEATURE:
<223> OTHER INFORMATION: Nucleotide sequence of heavy chain of 008

<400> SEQUENCE: 39

```
atggcatgcc ctggcttcct gtgggcactt gtgatctcca cctgtcttga attctccatg      60
gccgaggtgc agctggtgga gtctggggga ggcttggtcc agcctggagg gtccctgaga     120
ctctcctgtg cagcctctgg attcaccttt agcaactaca cgatgaactg ggtccgccag     180
gcgcccggga aggggctgga gtgggtctca gctattagtg gtagtggtgg tagcacatac     240
tacgcagact ccgtgaaggg ccggttcacc atctccagag acaattccaa gaacacgctg     300
tatctgcaaa tgaacagcct gagagccgag gacacggccg tgtattactg tgccaaagac     360
cgctactccc aggtgcacta cgcgttggat tactggggcc agggcaccct ggtgaccgtc     420
tcctcagcct ccaccaaggg cccatcggtc ttccccctgg caccctcctc caagagcacc     480
tctgggggca gcgcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagagagtt     720
gagcccaaat cttgtgacaa aactcacaca tgcccaccgt gcccagcacc tgaactcctg     780
gggggaccgt cagtcttcct cttccccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggg cagccggaga caactacaa gaccacgcct    1260
```

-continued

```
cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaa                              1416
```

<210> SEQ ID NO 40
<211> LENGTH: 1410
<212> TYPE: DNA
<213> ORGANISM: Artificial sequence
<220> FEATURE:
<223> OTHER INFORMATION: Nucleotide sequence of heavy chain of 011

<400> SEQUENCE: 40

```
atggcatgcc ctggcttcct gtgggcactt gtgatctcca cctgtcttga attctccatg      60
gccgaggtgc agctggtgga gtctggggga ggcgtggtcc agcctgggag gtccctgaga     120
ctctcctgtg cagcctctgg attcaccttc agcgactaca cgatgaactg ggtccgccag     180
gcgcccggga aggggctgga gtgggtctca tccattagtg gtggtagcac atactacgca     240
gactccagga agggcagatt caccatctcc agagacaatt ccaagaacac gctgtatctt     300
caaatgaaca acctgagagc tgaggacacg gccgtgtatt actgtgcaag agaccgctac     360
ttcaggcagc agaacgcgtt cgattactgg ggccagggca cctggtgac cgtctcctca      420 gcctccacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca ccgtgcccag cacctgaact cctggggga     780 ccgtcagtct tcctcttccc cccaaaaccc aaggacaccc tcatgatctc ccggaccct     840 gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa                                    1410
```

<210> SEQ ID NO 41
<211> LENGTH: 1416
<212> TYPE: DNA
<213> ORGANISM: Artificial sequence
<220> FEATURE:
<223> OTHER INFORMATION: Nucleotide sequence of heavy chain of 021

<400> SEQUENCE: 41

```
atggcatgcc ctggcttcct gtgggcactt gtgatctcca cctgtcttga attctccatg      60
gccgaggtgc agctggtgga gtctggggga ggcttggtac agcctagggg gtccctgaga     120
ctctcctgtg cagcctctgg attcaccttt agcagctacg cgatgaactg ggtccgccag     180
```

```
gcgcccggga agggctggga gtgggtggca gttatatcat atgatggaag caataaatac    240
tacgcagact ccgtgaaggg ccgattcacc atctccagag acaattccaa gaacacgctg    300
tatctgcaaa tgaacagcct gagagctgag gacacagccg tgtattactg tgccaaagac    360
cgctacatca cgttgccgaa cgcgttggat tactggggcc agggcaccct ggtgaccgtc    420
tcctcagcct ccaccaaggg cccatcggtc ttccccctgg cacccctcc caagagcacc     480 tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagagagtt    720
gagcccaaat cttgtgacaa aactcacaca tgcccaccgt gcccagcacc tgaactcctg    780
gggggaccgt cagtcttcct cttccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gaggagatga ccaagaacca ggtcagcctg acctgcctgg tcaaaggctt ctatcccagc   1200
gacatcgccg tggagtggga gagcaatggg cagccggaga caactacaa gaccacgcct    1260 cccgtgctgg actccgacgg ctccttcttc ctctatagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                              1416

<210> SEQ ID NO 42
<211> LENGTH: 1413
<212> TYPE: DNA
<213> ORGANISM: Artificial sequence
<220> FEATURE:
<223> OTHER INFORMATION: Nucleotide sequence of heavy chain of 023

<400> SEQUENCE: 42
atggcatgcc ctggcttcct gtgggcactt gtgatctcca cctgtcttga attctccatg     60
gccgaggtgc agctggtgga gtctgggga ggcttggtac atcctggggg gtccctgaga    120
ctctcctgtg caggctctgg attcaccttc agtagctatg ctatgcactg ggttcgccag    180
gctccaggaa aaggtctgga gtgggtatca gctattggta ctggtggtgg cacatactat    240
gcagactccg tgatgggccg gttcaccatc tccagagaca attccaagaa cacgctgtat   300
ctgcaaatga acagcctgag agccgaggac acggccgtgt attactgtgc aagatacgac    360
aatgtgatgg gtctttactg gtttgactac tggggccagg gcaccctggt gaccgtctcc    420
tcagcctcca ccaagggccc atcggtcttc ccctggcac cctcctccaa gagcacctct   480
gggggcacag cggccctggg ctgcctggtc aaggactact cccccgaacc ggtgacggtg    540
tcgtggaact caggcgccct gaccagcggc gtgcacacct tccggctgt cctacagtcc   600 tcaggactct actccctcag cagcgtggtg accgtgccca gcagcttggg cacccag     660 acctacatct gcaacgtgaa tcacaagccc agcaacacca aggtggacaa gagagttgag    720
cccaaatctt gtgacaaaac tcacacatgc ccaccgtgcc cagcacctga actcctgggg    780
```

| | |
|---|---|
| ggaccgtcag tcttcctctt cccccaaaa cccaaggaca ccctcatgat ctcccggacc | 840 |
| cctgaggtca catgcgtggt ggtggacgtg agccacgaag accctgaggt caagttcaac | 900 |
| tggtacgtgg acggcgtgga ggtgcataat gccaagacaa agccgcggga ggagcagtac | 960 |
| aacagcacgt accgtgtggt cagcgtcctc accgtcctgc accaggactg gctgaatggc | 1020 |
| aaggagtaca agtgcaaggt ctccaacaaa gccctcccag cccccatcga aaaaccatc | 1080 |
| tccaaagcca agggcagcc ccgagaacca caggtgtaca ccctgccccc atcccgggag | 1140 |
| gagatgacca gaaccaggt cagcctgacc tgcctggtca aaggcttcta tcccagcgac | 1200 |
| atcgccgtgg agtgggagag caatgggcag ccggagaaca actacaagac cacgcctccc | 1260 |
| gtgctggact ccgacggctc cttcttcctc tatagcaagc tcaccgtgga caagagcagg | 1320 |
| tggcagcagg ggaacgtctt ctcatgctcc gtgatgcatg aggctctgca caaccactac | 1380 |
| acgcagaaga gcctctccct gtctccgggt aaa | 1413 |

<210> SEQ ID NO 43
<211> LENGTH: 720
<212> TYPE: DNA
<213> ORGANISM: Artificial sequence
<220> FEATURE:
<223> OTHER INFORMATION: Nucleotide sequence of light chain of 008

<400> SEQUENCE: 43

| | |
|---|---|
| atggcatgcc ctggcttcct gtgggcactt gtgatctcca cctgtctcga gttttccatg | 60 |
| gctgacatcg tgatgacaca gtctccagac tcactgcccg tcaccctgg agagccggcc | 120 |
| tccatctcct gcaggtctag tcagagcctc ctgcatagta tggatacaa ctatttggat | 180 |
| tggtacctgc agaaggcagg gcagtctcca cagctcctga tctatttggg ttctaatcgg | 240 |
| gcctccgggg tccctgacag gttcagtggc agtggatcag gcacagattt tacactgaaa | 300 |
| atcagcagag tggaggctga ggatgttggg gtttattact gccagcagta ctacaaccac | 360 |
| ccgacgacct tcggccaggg caccaaactg gaaatcaaac gtactgtggc tgcaccatct | 420 |
| gtcttcatct tcccgccatc tgatgagcag ttgaaatctg gaactgcctc tgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga aacacaaagt ctacgcctgc | 660 |
| gaagtcaccc atcagggcct gagctcgccc gtcacaaaga gcttcaacag gggagagtgt | 720 |

<210> SEQ ID NO 44
<211> LENGTH: 720
<212> TYPE: DNA
<213> ORGANISM: Artificial sequence
<220> FEATURE:
<223> OTHER INFORMATION: Nucleotide sequence of light chain of 011

<400> SEQUENCE: 44

| | |
|---|---|
| atggcatgcc ctggcttcct gtgggcactt gtgatctcca cctgtctcga gttttccatg | 60 |
| gctgacatcg tgatgacaca gtctccagtc accctgcccg tcaccctgg agagccggcc | 120 |
| tccatctcct gcaggtctag tcagagcctc ctgcatagta tggatacaa ctatttggat | 180 |
| tggtacctgc agaagccagg gcagtctcca cagctcctga tctatttggg ttctaatcgg | 240 |
| gcctccgggg tccctgacag gttcagtggc agtggatcag gcacagattt tacactgaaa | 300 |
| atcagcagag tggaggctga ggatgttggg gtttattact gccagcagta cctcacggcc | 360 |
| ccgcccacct tcggccaggg caccaaactg gaaatcaaac gtactgtggc tgcaccatct | 420 |

```
gtcttcatct tcccgccatc tgatgagcag ttgaaatctg gaactgcctc tgttgtgtgc      480
ctgctgaata acttctatcc cagagaggcc aaagtacagt ggaaggtgga taacgccctc      540
caatcgggta actcccagga gagtgtcaca gagcaggaca gcaaggacag cacctacagc      600
ctcagcagca ccctgacgct gagcaaagca gactacgaga acacaaagt ctacgcctgc       660 gaagtcaccc atcagggcct gagctcgccc gtcacaaaga gcttcaacag gggagagtgt     720

<210> SEQ ID NO 45
<211> LENGTH: 720
<212> TYPE: DNA
<213> ORGANISM: Artificial sequence
<220> FEATURE:
<223> OTHER INFORMATION: Nucleotide sequence of light chain of 021

<400> SEQUENCE: 45
atggcatgcc ctggcttcct gtgggcactt gtgatctcca cctgtctcga gttttccatg       60
gctgacatcc agatgaccca gtctccagtc tcactgcccg tcaccctgg agagccggcc       120 tccatctcct gcaggtctag tcagagcctc ctgcatagta atggatacaa ctatttggat      180
tggtacctgc agaagccagg gcagtctcca cagctcctga tctatttggg ttctaatcgg      240
gcctccgggg tccctgacag gttcagtggc agtggatcag gcacagattt tacactgaaa      300
atcagcagag tggaggctga ggatgttggg gtttattact gccagcagta caagtcgaac      360
ccgcccacct cggccaggg caccaaagtg gaaatcaaac gtactgtggc tgcaccatct      420
gtcttcatct cccgccatc tgatgagcag ttgaaatctg gaactgcctc tgttgtgtgc       480
ctgctgaata acttctatcc cagagaggcc aaagtacagt ggaaggtgga taacgccctc      540
caatcgggta actcccagga gagtgtcaca gagcaggaca gcaaggacag cacctacagc      600
ctcagcagca ccctgacgct gagcaaagca gactacgaga acacaaagt ctacgcctgc       660 gaagtcaccc atcagggcct gagctcgccc gtcacaaaga gcttcaacag gggagagtgt     720

<210> SEQ ID NO 46
<211> LENGTH: 705
<212> TYPE: DNA
<213> ORGANISM: Artificial sequence
<220> FEATURE:
<223> OTHER INFORMATION: Nucleotide sequence of light chain of 023

<400> SEQUENCE: 46
atggcatgcc ctggcttcct gtgggcactt gtgatctcca cctgtctcga gttttccatg       60
gctgaaattg tgctcacaca gtctccagcc accctgtctt tgtctccagg ggaaagagcc      120
accctctcct gcagggccag tcagagtgtt agcagctact tagcctggta ccaacagaaa      180
cctggccagg ctcccaggct cctcatctat gatgcatcca cagggccac tggcatccca       240 gccaggttca gtggcagtgg gtctgggaca gacttcactc tcaccatcag cagcctagag      300
cctgaagatt ttgcagttta ttactgtcag cagcgtagca ctggcctcc ggctttcggc       360 ggagggacca aggtggagat caaacgtact gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcccctg      600 acgctgagca agcagacta cgagaaacac aaagtctacg cctgcgaagt cacccatcag      660
ggcctgagct cgcccgtcac aaagagcttc aacagggag agtgt                       705
```

<210> SEQ ID NO 47
<211> LENGTH: 46
<212> TYPE: DNA
<213> ORGANISM: Artificial sequence
<220> FEATURE:
<223> OTHER INFORMATION: Primer

<400> SEQUENCE: 47
acctgtcttg aattctccat ggccgaggtg cagctggtgg agtctg            46

<210> SEQ ID NO 48
<211> LENGTH: 51
<212> TYPE: DNA
<213> ORGANISM: Artificial sequence
<220> FEATURE:
<223> OTHER INFORMATION: Primer

<400> SEQUENCE: 48
gctcgcggat ccactcacct gaggagacgg tcaccagggt gccctggccc c       51

<210> SEQ ID NO 49
<211> LENGTH: 49
<212> TYPE: DNA
<213> ORGANISM: Artificial sequence
<220> FEATURE:
<223> OTHER INFORMATION: Primer

<400> SEQUENCE: 49
acctgtctcg agttttccat ggctgacatc gtgatgacac agtctccag          49

<210> SEQ ID NO 50
<211> LENGTH: 47
<212> TYPE: DNA
<213> ORGANISM: Artificial sequence
<220> FEATURE:
<223> OTHER INFORMATION: Primer

<400> SEQUENCE: 50
acctgtctcg agttttccat ggctgacatc gtgatgaccc agtctcc            47

<210> SEQ ID NO 51
<211> LENGTH: 54
<212> TYPE: DNA
<213> ORGANISM: Artificial sequence
<220> FEATURE:
<223> OTHER INFORMATION: Primer

<400> SEQUENCE: 51
acctgtctcg agttttccat ggctgaaatt gtgctcacac agtctccagc cacc    54

<210> SEQ ID NO 52
<211> LENGTH: 55
<212> TYPE: DNA
<213> ORGANISM: Artificial sequence
<220> FEATURE:
<223> OTHER INFORMATION: Primer

<400> SEQUENCE: 52
ttttccttag cggccgcaaa gtgcacttac gtttgatttc cagtttggtg ccctg   55

<210> SEQ ID NO 53
<211> LENGTH: 55
<212> TYPE: DNA
<213> ORGANISM: Artificial sequence
<220> FEATURE:
<223> OTHER INFORMATION: Primer

```
<400> SEQUENCE: 53
ttttccttag cggccgcaaa gtgcacttac gtttgatttc cactttggtg ccctg        55

<210> SEQ ID NO 54
<211> LENGTH: 55
<212> TYPE: DNA
<213> ORGANISM: Artificial sequence
<220> FEATURE:
<223> OTHER INFORMATION: Primer

<400> SEQUENCE: 54
ttttccttag cggccgcaaa gtgcacttac gtttgatctc caccttggtc cctcc        55
```

The invention claimed is:

1. A human antibody able to bind to the human OX40 receptor, wherein the antibody comprises
a heavy chain variable region comprising the variable region of amino acid sequence SEQ ID NO:27, or a sequence that is at least 97% homologous thereto, and
wherein the human antibody comprises a light chain variable region comprising the variable region of amino acid sequence of SEQ ID NO: 31, or a sequence that is at least 97% homologous thereto.

2. The human antibody of claim 1, wherein the human antibody comprises a complementary determining region that comprises the amino acid sequence SEQ ID NO:22.

3. An immunoconjugate comprising the antibody of claim 1 and at least one tag.

4. An antibody capable of binding to the human OX40 receptor, produced by a method comprising:

culturing under conditions conducive to the expression of the antibody in a host comprising at least one vector encoding an antibody thereof able to bind to the human OX40 receptor;
expressing the antibody; and
isolating the antibody,
wherein the antibody is an antibody according to claim 1.

5. A composition comprising the antibody of claim 1 and a stabilizing molecule.

6. A pharmaceutical composition comprising the human antibody of claim 1 and at least one pharmaceutically acceptable excipient.

7. The pharmaceutical composition of claim 6 further comprising at least one other therapeutic agent.

8. A human antibody capable of binding to the human OX40 receptor, comprising a heavy chain comprising amino acid sequence SEQ ID NO:27, and a light chain comprising amino acid sequence of SEQ ID NO: 31.

* * * * *

UNITED STATES PATENT AND TRADEMARK OFFICE
CERTIFICATE OF CORRECTION

PATENT NO. : 7,550,140 B2
APPLICATION NO. : 10/517941
DATED : June 23, 2009
INVENTOR(S) : Alexander Berthold Hendrik Bakker et al.

It is certified that error appears in the above-identified patent and that said Letters Patent is hereby corrected as shown below:

On the title page:
In ITEM (56) References Cited
OTHER PUBLICATIONS
Page 1, 2nd column, 2nd line of the
4th entry (line 22), change "an dBinding" to --and Binding--
Page 1, 2nd column, 1st line of the
5th entry (line 23), change "Reccombinant antibodies"
to --Recombinant antibodies by--

Signed and Sealed this
Twelfth Day of March, 2013

Teresa Stanek Rea
*Acting Director of the United States Patent and Trademark Office*